(12) United States Patent
Parker et al.

(10) Patent No.: US 9,669,141 B2
(45) Date of Patent: Jun. 6, 2017

(54) TISSUE-ENGINEERED PUMPS AND VALVES AND USES THEREOF

(71) Applicants: President and Fellows of Harvard College, Cambridge, MA (US); California Institute of Technology, Pasadena, CA (US)

(72) Inventors: Kevin Kit Parker, Cambridge, MA (US); Josue A. Goss, Cambridge, MA (US); Sung-Jin Park, Lexington, MA (US); Andrew K. Capulli, Billerica, MA (US); Holly M. Golecki, Acton, MA (US); Janna C. Nawroth, Boston, MA (US); John O. Dabiri, Pasadena, CA (US)

(73) Assignees: President and Fellows of Harvard College, Cambridge, MA (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 14/415,945

(22) PCT Filed: Jul. 19, 2013

(86) PCT No.: PCT/US2013/051267
§ 371 (c)(1),
(2) Date: Jan. 20, 2015

(87) PCT Pub. No.: WO2014/015251
PCT Pub. Date: Jan. 23, 2014

(65) Prior Publication Data
US 2015/0182679 A1    Jul. 2, 2015

Related U.S. Application Data

(60) Provisional application No. 61/674,234, filed on Jul. 20, 2012.

(51) Int. Cl.
*A61M 1/10* (2006.01)
*A61F 2/24* (2006.01)
(Continued)

(52) U.S. Cl.
CPC ......... *A61M 1/1003* (2014.02); *A61F 2/2415* (2013.01); *A61M 1/1037* (2013.01);
(Continued)

(58) Field of Classification Search
CPC   A61M 1/1001–1/1006; A61M 1/1096; A61M 1/122–1/127; A61M 1/1098;
(Continued)

(56) References Cited

U.S. PATENT DOCUMENTS

| 8,492,150 B2 | 7/2013 | Parker et al. |
| 9,012,172 B2 | 4/2015 | Parker et al. |

(Continued)

FOREIGN PATENT DOCUMENTS

| WO | WO-2008/051265 A2 | 5/2008 | |
| WO | WO 2010132636 A1 * | 11/2010 | ........... C12N 5/0068 |

(Continued)

OTHER PUBLICATIONS

Pilarek et al, "Biological cardio-micro-pumps for microbioreactors and analytical micro-systems", (Aug. 2011), Sensors and Actuators B: Chemical, vol. 156, Issue 2, pp. 517-526.*

(Continued)

*Primary Examiner* — Paul Prebilic
(74) *Attorney, Agent, or Firm* — McCarter & English, LLP; Deborah L. Nagle; Anita M. Bowles

(57) ABSTRACT

The present invention provides tissue-engineered pumps and valves, methods of fabricating such pumps and valves, and methods of use of such pumps and valves.

19 Claims, 34 Drawing Sheets

Optimal design

(51) Int. Cl.
*G01N 33/50* (2006.01)
*A61M 1/12* (2006.01)

(52) U.S. Cl.
CPC ........ *A61M 1/1053* (2013.01); *A61M 1/1098* (2014.02); *A61M 1/122* (2014.02); *A61M 1/127* (2013.01); *G01N 33/5061* (2013.01); *A61M 1/12* (2013.01); *G01N 2500/04* (2013.01); *G01N 2500/10* (2013.01); *Y10T 29/49405* (2015.01)

(58) Field of Classification Search
CPC .................. A61F 2/2415; A61F 2/2469; A61F 2230/0067; A61F 2240/001; A61F 2240/008; A61F 2250/0039; G01N 33/5061; G01N 2500/04; G01N 2500/10; G01N 1/1001
See application file for complete search history.

(56) References Cited

U.S. PATENT DOCUMENTS

| | | | |
|---|---|---|---|
| 9,068,168 B2 | 6/2015 | Feinberg et al. | |
| 2004/0009566 A1 | 1/2004 | Okano et al. | |
| 2004/0078090 A1 | 4/2004 | Binette et al. | |
| 2004/0101819 A1 | 5/2004 | Montemagno et al. | |
| 2005/0080402 A1 | 4/2005 | Santamore et al. | |
| 2005/0085847 A1 | 4/2005 | Galdonik et al. | |
| 2006/0003439 A1 | 1/2006 | Ismagilov et al. | |
| 2006/0253192 A1* | 11/2006 | Atala ................... | A61F 2/2415 623/2.13 |
| 2007/0164641 A1 | 7/2007 | Pelrine et al. | |
| 2007/0197857 A1* | 8/2007 | Palmer ................ | A61M 1/1037 600/16 |
| 2008/0031818 A1* | 2/2008 | Bush ..................... | A61K 31/00 424/9.2 |
| 2009/0317852 A1 | 12/2009 | Parker et al. | |
| 2010/0196432 A1 | 8/2010 | Feinberg et al. | |
| 2010/0330644 A1 | 12/2010 | Feinberg et al. | |
| 2011/0041935 A1 | 2/2011 | Zhou et al. | |
| 2011/0189719 A1 | 8/2011 | Kuo et al. | |
| 2012/0135448 A1* | 5/2012 | Parker ................... | C12N 5/0068 435/29 |
| 2012/0142556 A1 | 6/2012 | Parker et al. | |
| 2013/0046134 A1 | 2/2013 | Parker et al. | |
| 2013/0053625 A1* | 2/2013 | Merc Vives ........ | A61M 1/1037 600/16 |
| 2013/0312638 A1 | 11/2013 | Parker et al. | |
| 2013/0330378 A1 | 12/2013 | Parker et al. | |
| 2014/0322515 A1 | 10/2014 | Parker et al. | |
| 2014/0342394 A1 | 11/2014 | Parker et al. | |
| 2015/0253307 A1 | 9/2015 | Parker et al. | |

FOREIGN PATENT DOCUMENTS

| | | |
|---|---|---|
| WO | WO-2011/102991 A1 | 8/2011 |
| WO | WO-2012/006320 A1 | 1/2012 |
| WO | WO-2012/048242 A1 | 4/2012 |

OTHER PUBLICATIONS

Parker et al., "Ectracellular matrix, mechanotransduction and struction hierarchies in heart tissue engineering." *Phil Trans R. Soc B*, Epub Jun. 22, 2007, vol. 362, pp. 1267-1279.

Alford et al., "Biohybrid thin films for measuring contractility in engineered cardiovascular muscle" Biomaterials, Feb. 9, 2010, vol. 31: pp. 3613-3621.

Bray et al., "Sarcomere Alignment is Regulated by Myocyte Shape" Cell Motility and the Cytoskeleton, Aug. 2008, vol. 65(8): pp. 641-651.

Bursac et al., "Cardiomyocyte cultures with controlled macroscopic anisotropy." Circulation Rearch, Dec. 13, 2002, vol. 91(12): pp. e45-e54.

Grosberg et al., "Ensembles of engineered cardiac tissues for physiological and pharmacological study: Heart on a chip." Lab Chip, Nov. 10, 2011, vol. 11: pp. 4165-4173.

Lehnert et al., "Cell behavior on micropatterned substrata: limits of extracellular matrix geometry for spreading and adhesion." Journal of Cell Science, Jan. 1, 2004, vol. 117 (1): pp. 41-52.

Mao et al., "Capillary isoelectric focusing with whole column imaging detection for analysis of proteins and peptides," J. Biochem. Biophys. Methods, Feb. 25, 1999, vol. 39: pp. 93-110.

Park et al., "Real-Time Measurement of the Contractile Forces of Self-Organized Cardiomyoctes on Hybrid Biopolymer Microcantilevers," Anal. Chem., Oct. 15, 2005, 77(20): 6571-6580.

Pilarek et al. "Biological cardio-micro-pumps for microbioreactors and analytical micro-systems," Sensors and Actuators B: Chemical, Aug. 2011, vol. 156, Issue.2: pp. 517-526.

Xi et al., "Development of a Self-Assembled Muscle-Powered Piezoelectric Microgenerator", NSTI-Nanotech, 2004, vol. 1: pp. 3-6. (The month of publication is not available; however, the year of publication is sufficiently earlier than the effective U.S. filed and any foreign priority date so that the particular month of publication is not an ssue.).

Yang et al., "Fabrication of well-defined PLGA scaffolds using novel microembossing and carbon dioxide bonding," Biomaterials, May 2005, vol. 26: pp. 2585-2594.

* cited by examiner

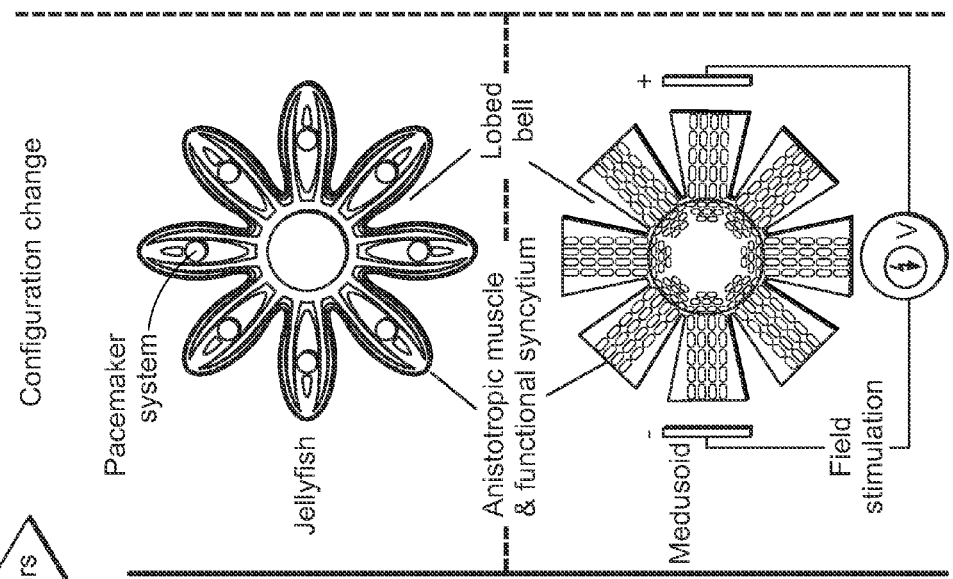
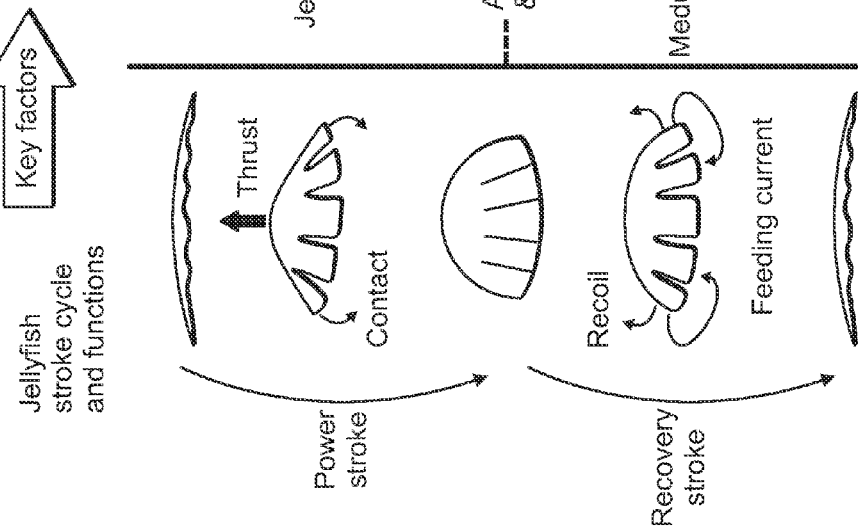
FIG. 1A
FIG. 1B

FIG. 1C
Stroke Kinematics
FIG. 1D
Fluid dynamics
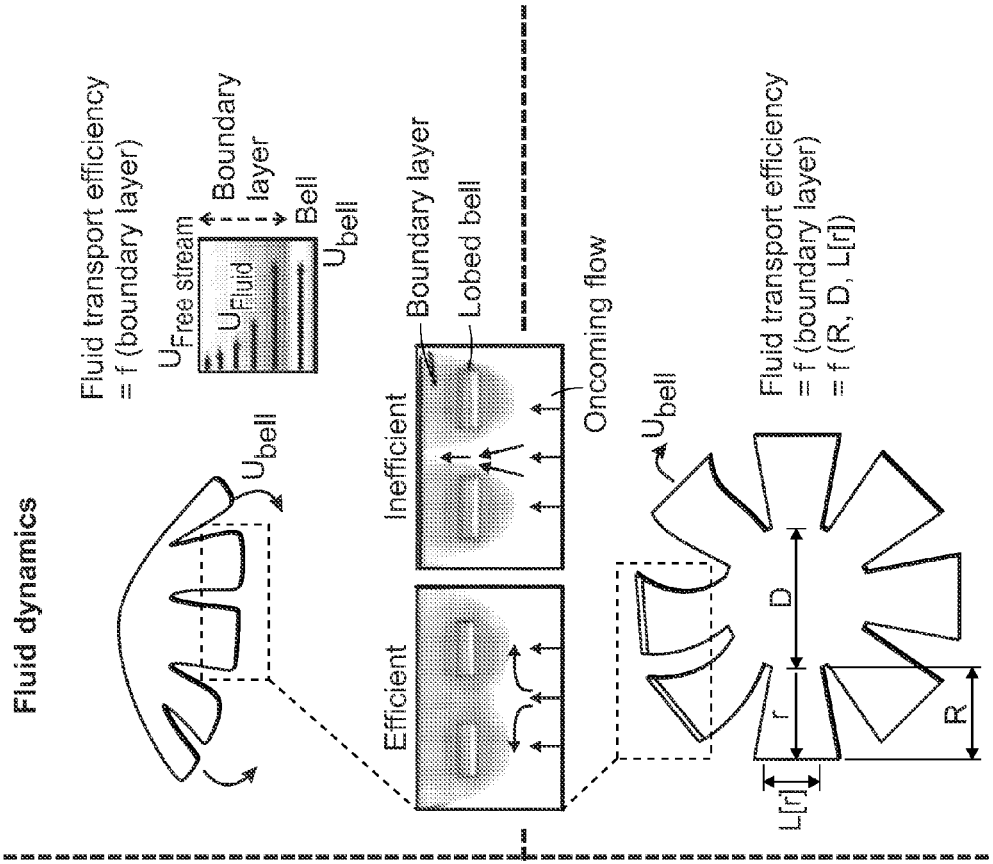
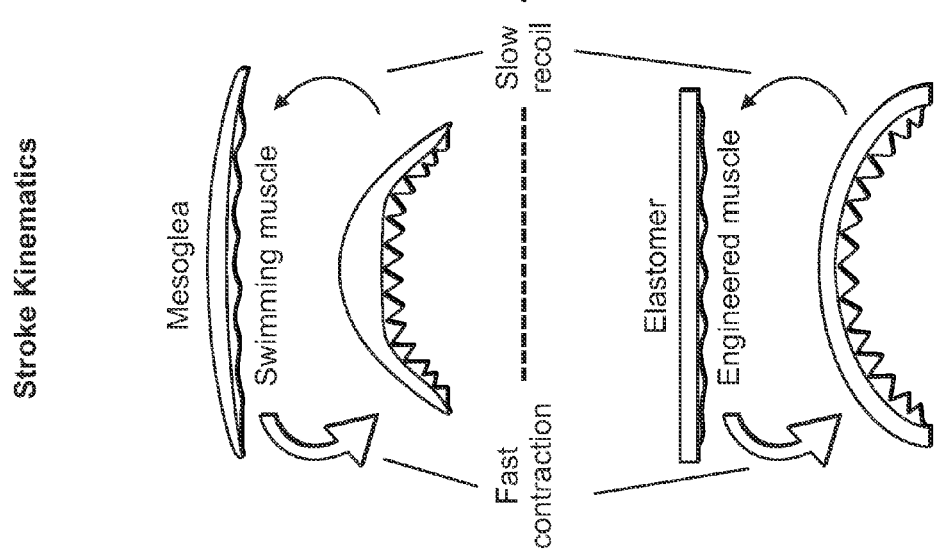

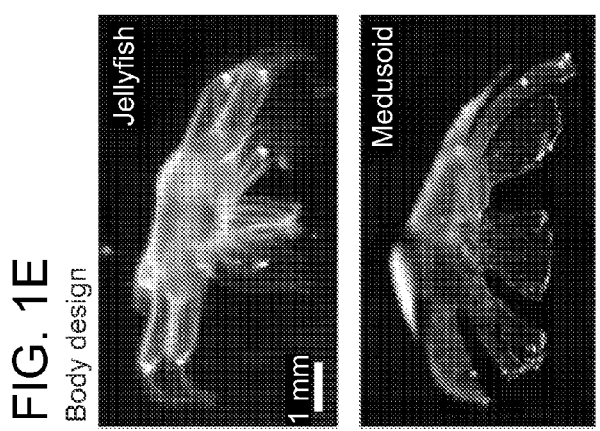
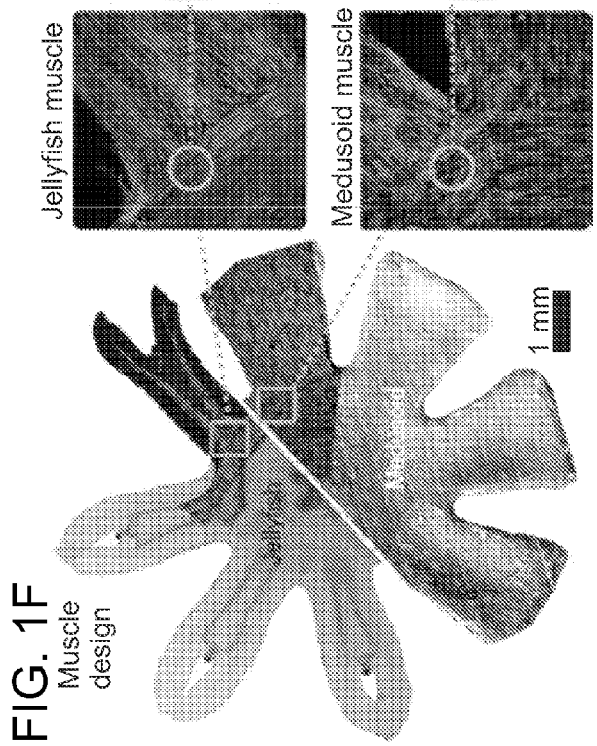
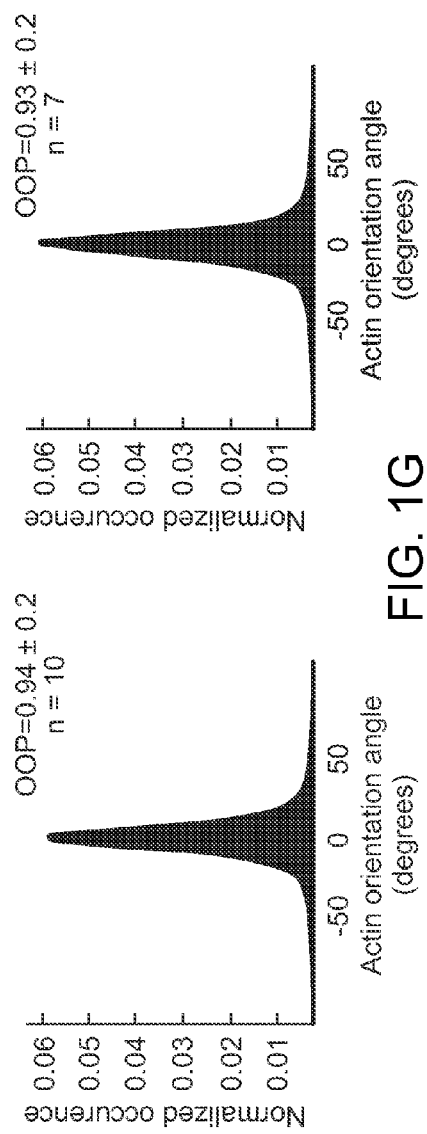
FIG. 1E Body design
FIG. 1F Muscle design
FIG. 1G

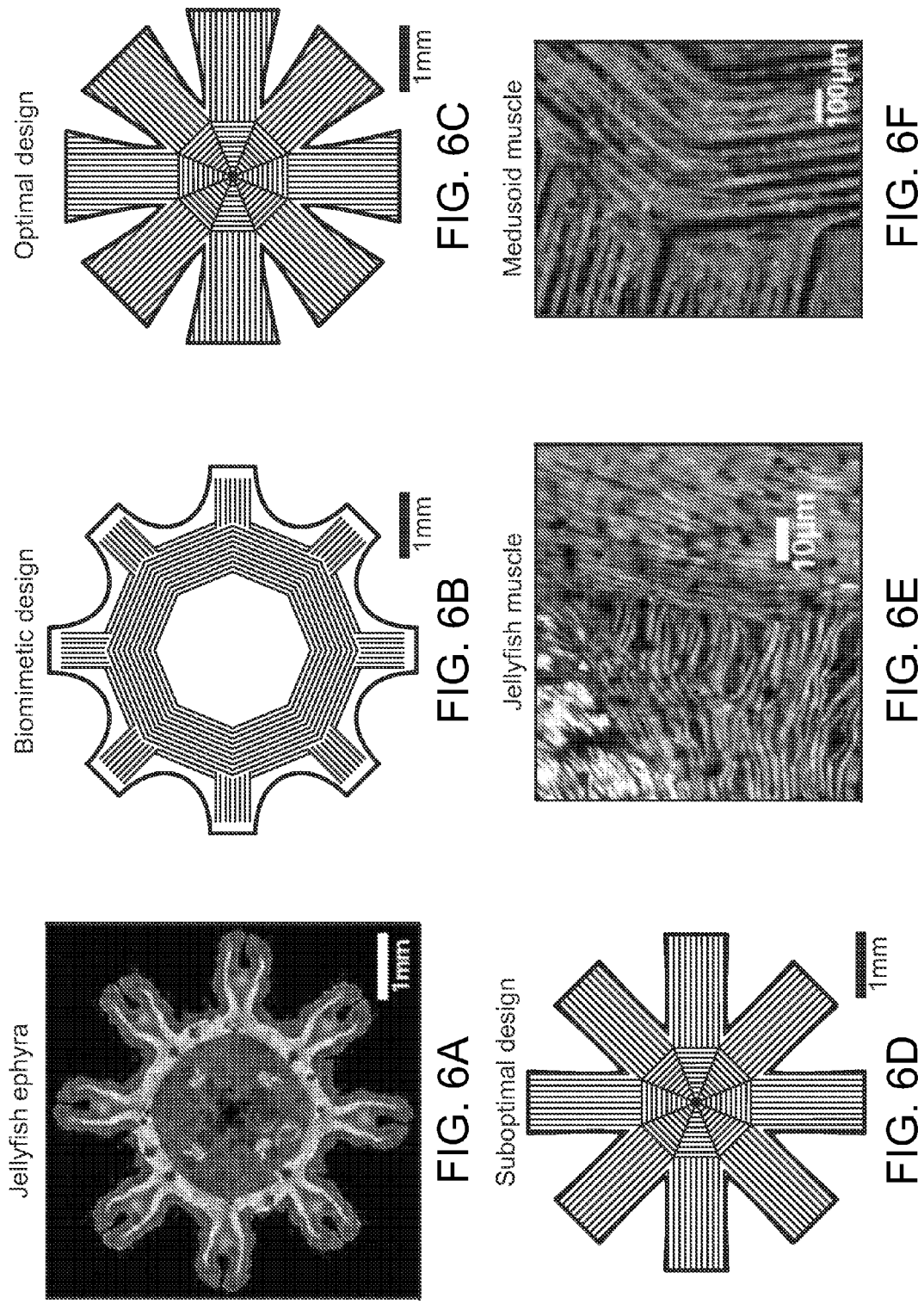

Jellyfish muscle physiology

Stimulating electrodes
Glass coverslip
Excess seawater
Jellyfish
Additional glass on top of jellyfish
Excitation filter
Light source
Dichroic mirror
Emission filter
Imaging diode array Radial Muscle, Lobe, Mesoglea, Pacemaker center Mesoglea, Muscle (RH237), Pacemaker, 50μm Channel array overlaid on field of view

Medusoid muscle physiology

Channel array overlaid on field of view

FIG. 8A
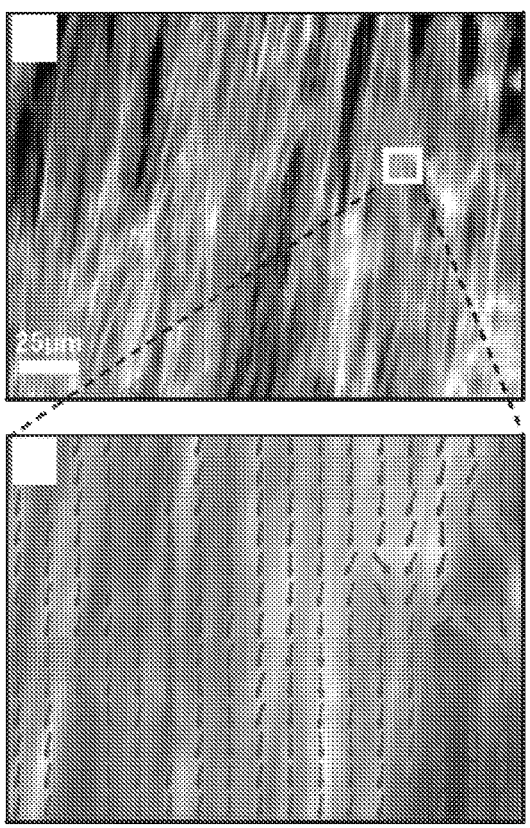
FIG. 8B
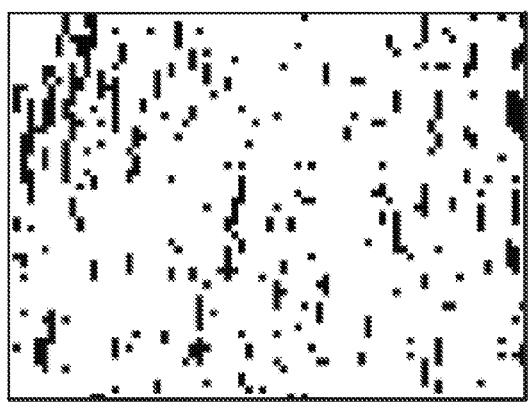
FIG. 8C
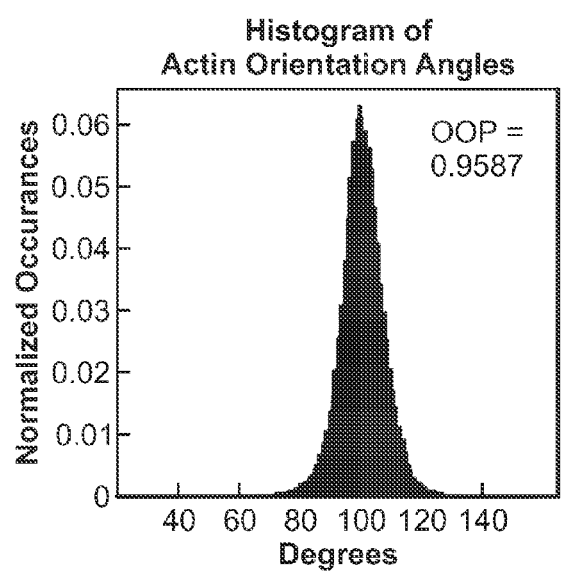
FIG. 8D

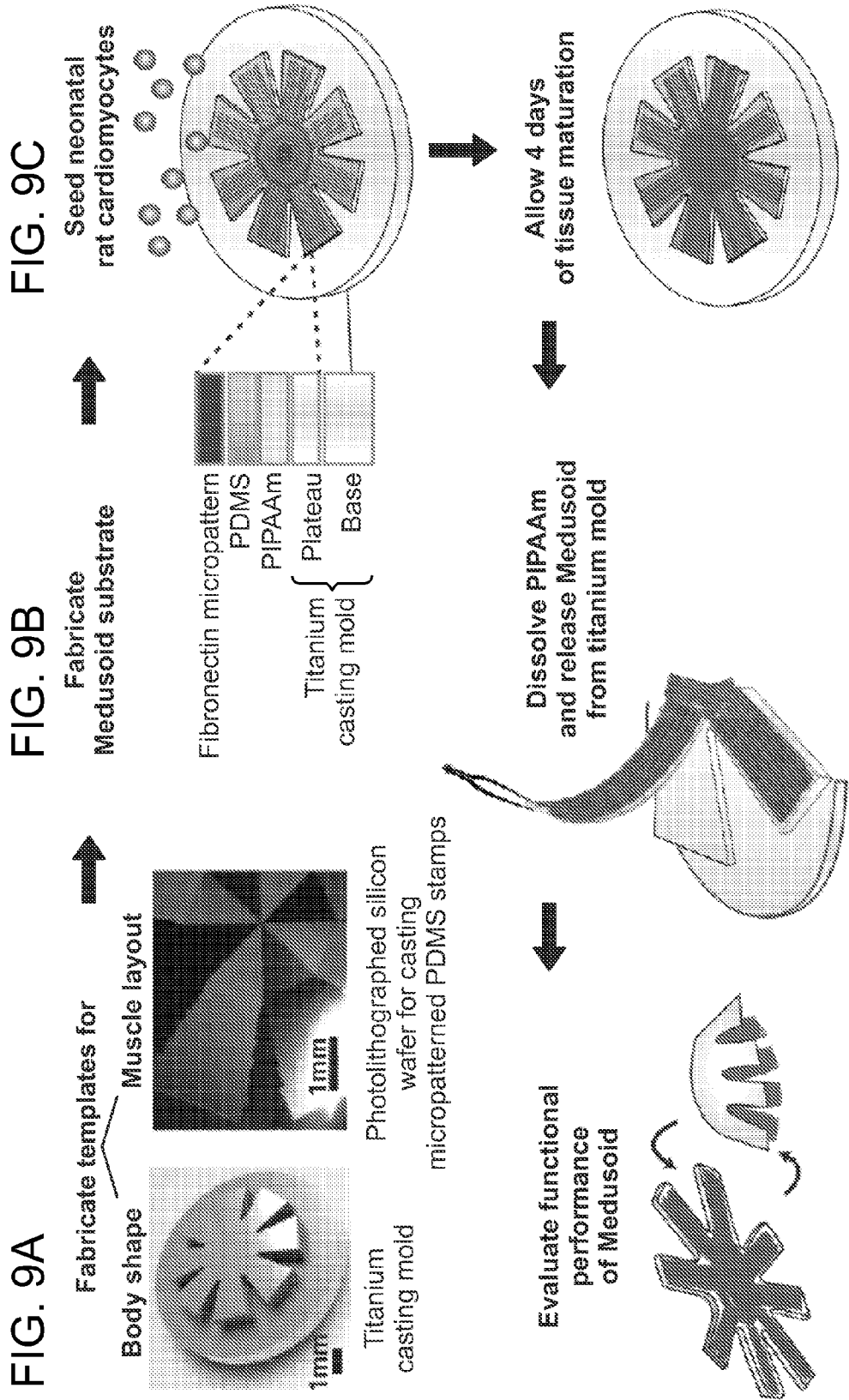

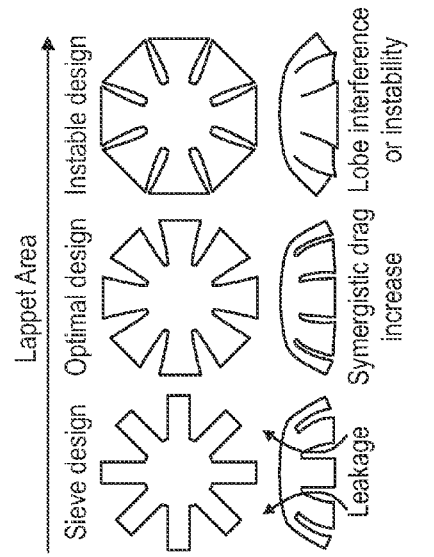
FIG. 11A
Design parameters
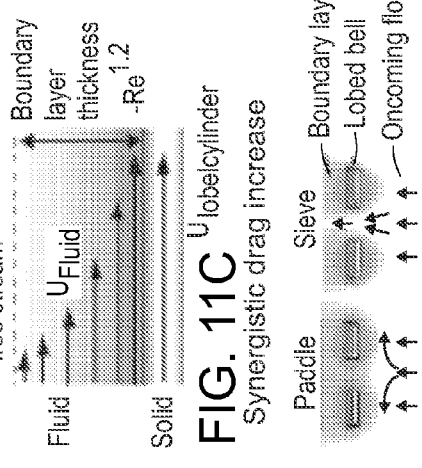
FIG. 11B
Boundary layer model
FIG. 11C
Synergistic drag increase
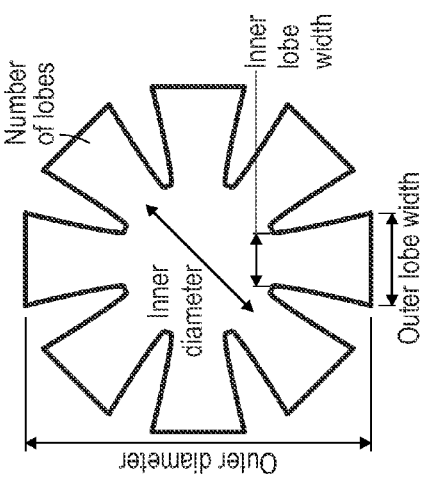
FIG. 11D
Design constraints
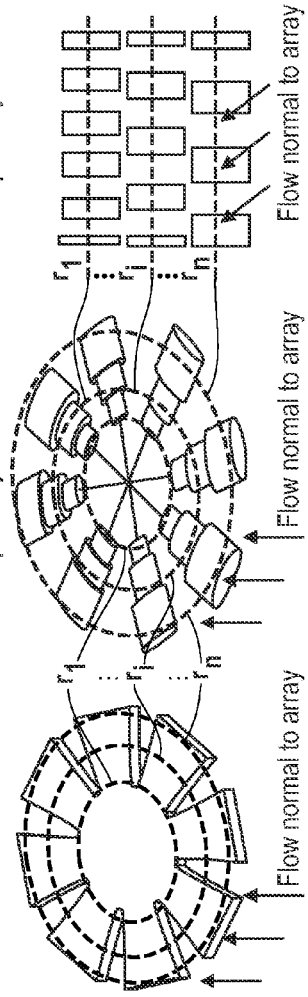
FIG. 11E
Simplified drag model
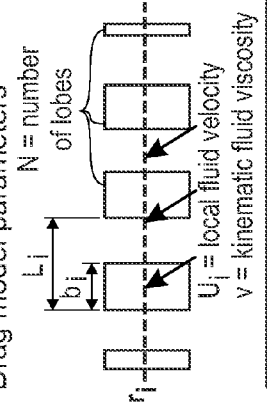
FIG. 11F
Drag model parameters
$N$ = number of lobes
$U_j$ = local fluid velocity
$v$ = kinematic fluid viscosity
Local porosity $P_j = (L_j - b_j) L_j^{-1}$
Local Reynolds number $Re_j = b_j U_j v^{-1}$
Local refrence area $A_j = (r_j + 1 - r_j) b_j N$

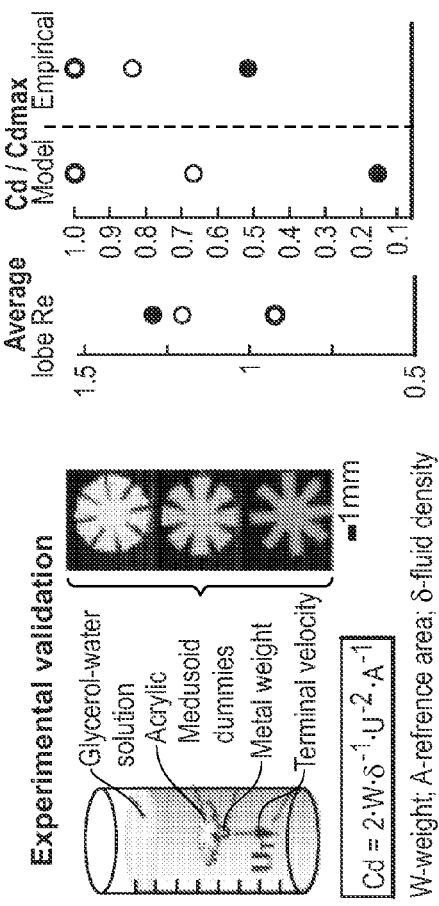
FIG. 11G  
FIG. 11H  
FIG. 11I
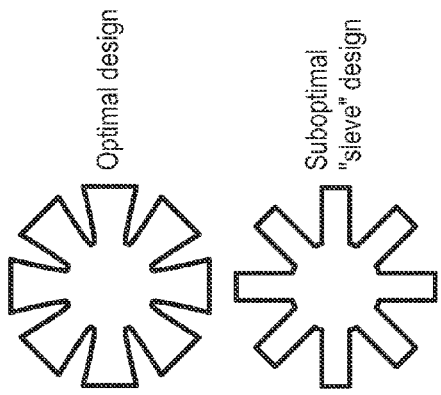
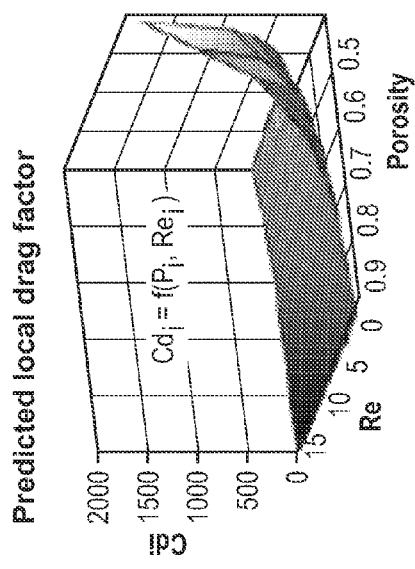
FIG. 11J
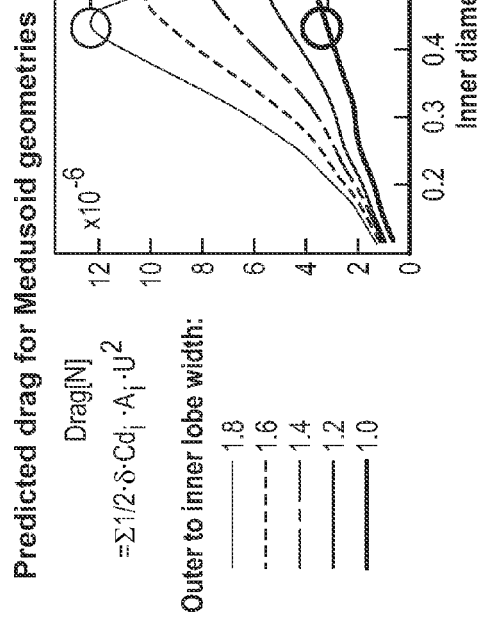

FIG. 12A
DPIV setup
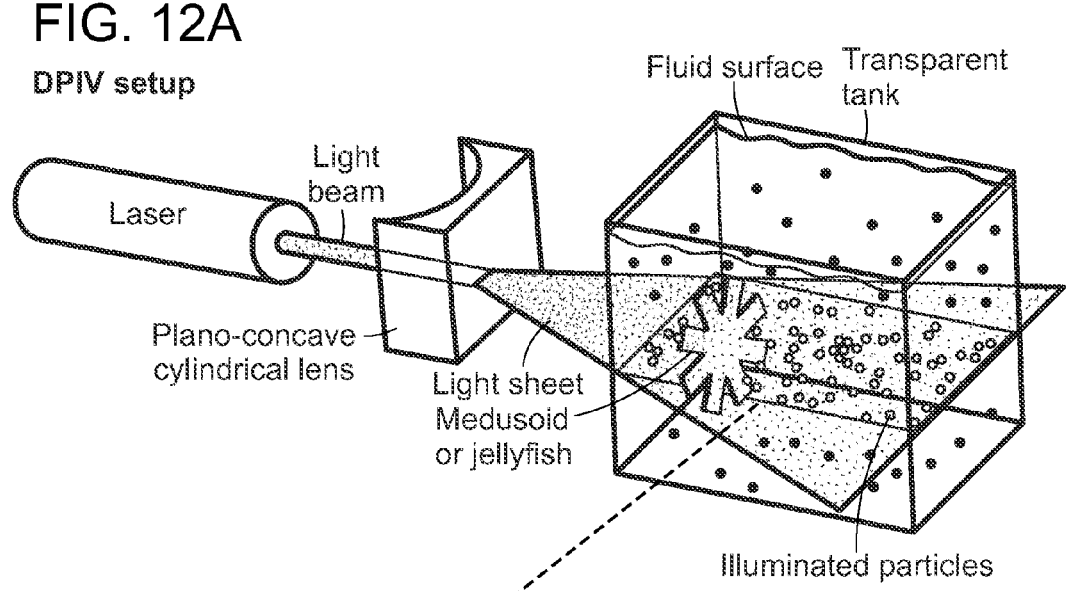
FIG. 12B
Camera field of view
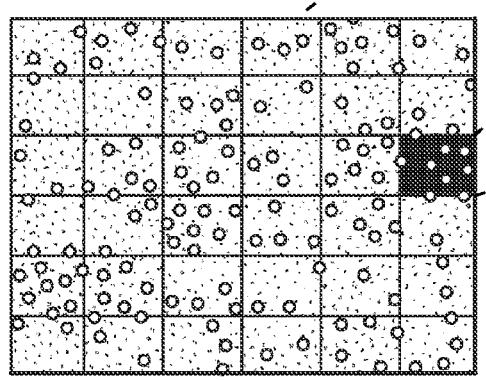
FIG. 12C
Interrogation window
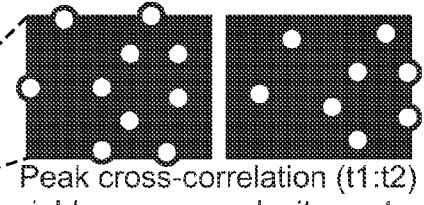
Peak cross-correlation (t1:t2) yields average velocity vector
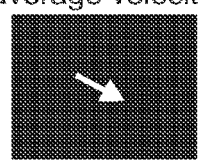

FIG. 12D
Flow field
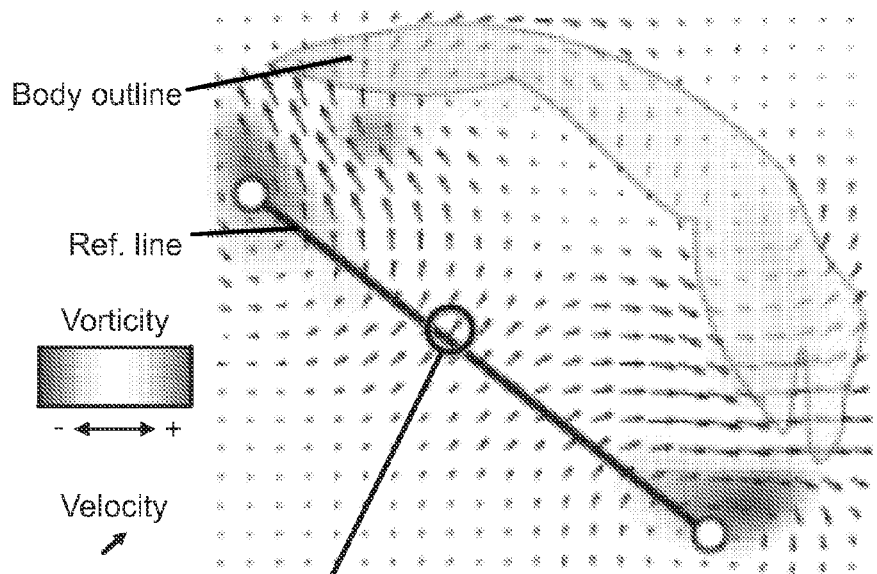
FIG. 12E
Velocity profile
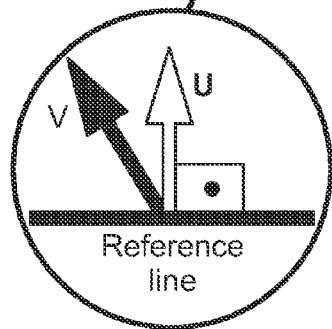
U = normal component of velocity vector V
Normalize U for bell radius R and stroke duration T
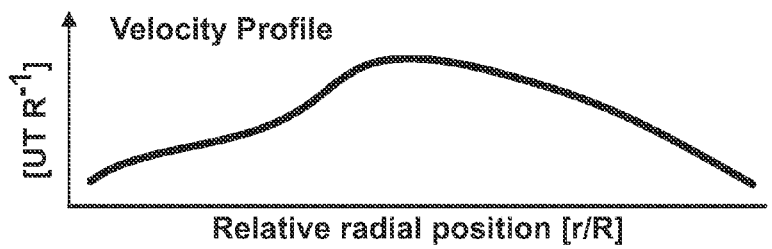

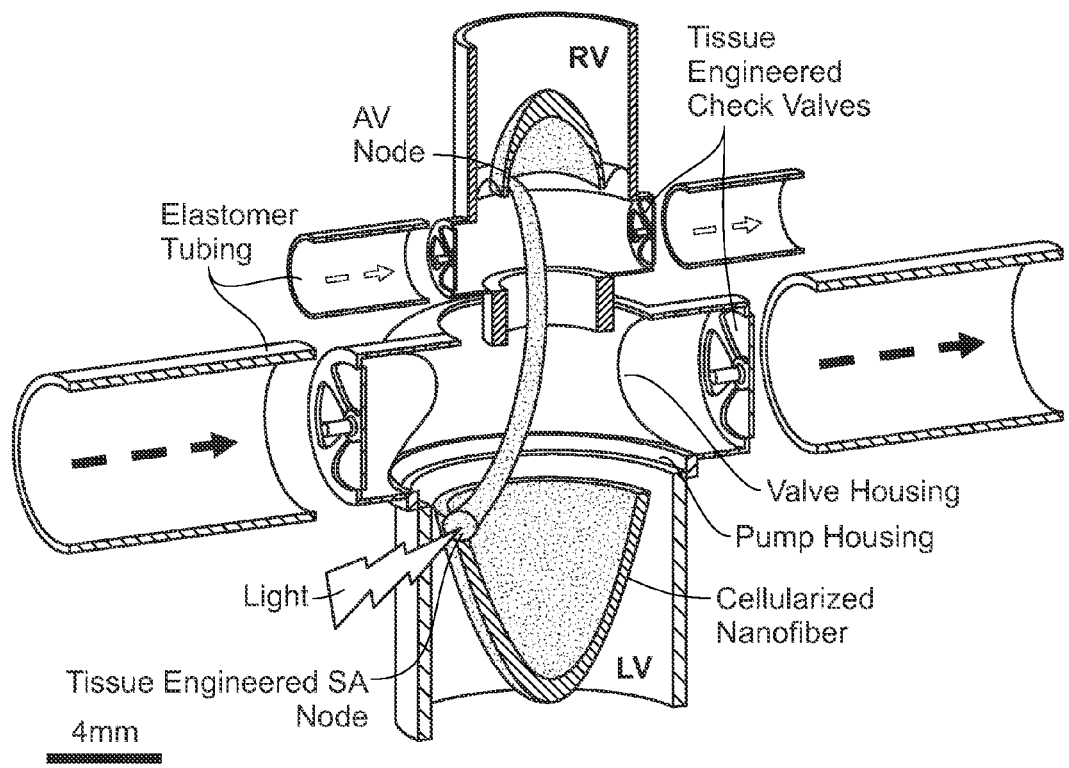
FIG. 16A
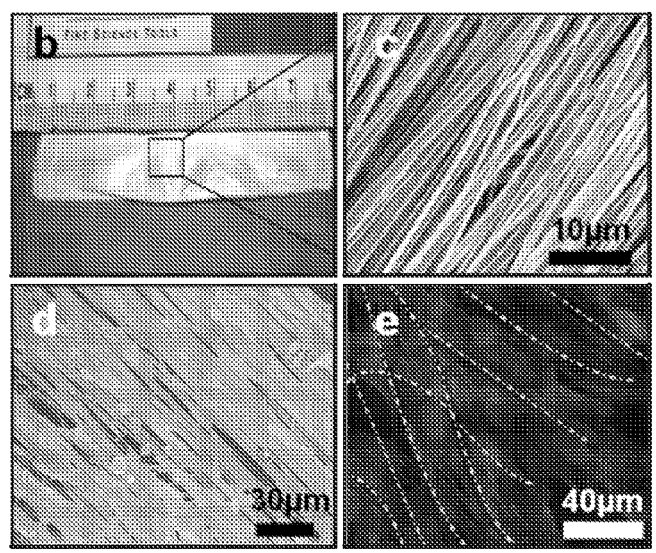
FIG. 16B   FIG. 16C
FIG. 16D   FIG. 16E

TISSUE-ENGINEERED PUMPS AND VALVES AND USES THEREOF

RELATED APPLICATIONS

This application is a 35 U.S.C. §371 national stage filling of International Application No. PCT/US2013/051267, filed on Jul. 19, 2013, which claims priority to U.S. Provisional Patent Application Ser. No. 61/674,234, filed Jul. 20, 2012, the entire contents of which are incorporated herein by reference.

GOVERNMENT SUPPORT

This invention was made with government support under grant number CBET 0931413, awarded by the NSF and with government support as a subcontract issued under Prime Contract Number DE-AC52-06NA25396 between Los Alamos National Laboratory and the United States Department of Energy (DOE) and the National Nuclear Science Administration (NNSA). The government has certain rights in the invention.

BACKGROUND

In some patients, heart disease may be so acute or severe that the patients may not survive the wait for a replacement valve and/or donor heart. Replacement valves and hearts and electronic devices such as ventricular assist devices, defibrillators, and pacemakers that can keep the patient alive until a heart becomes available have been developed. However, currently available devices are not durable and cannot work efficiently. In addition, the fluids and/or cells within such devices are subject to chemical and/or mechanical damage. For example, currently available devices result in mechanical or shear-induced cell lysis, material-dependent thrombogenesis, induction of coagulation, infection and endocarditis and patients must receive daily anticoagulant therapy. Replacement animal hearts and valves are also available. However, patients receiving such replacements must receive daily immunosuppressive therapy.

Accordingly, there is a need in the art for improved pumps and valves that are durable and can mimic the function of the human heart and do not have the side-effects associated with current devices.

SUMMARY OF THE INVENTION

The present invention is based, at least in part, on the assembly of synthetic muscular pumps and valves and provides tissue-engineered pumps and valves that more accurately mimic the function of a real heart without the need for a pump generated by a motor and which can be custom-sized based on the application.

Accordingly, in one aspect, the present invention provides tissue-engineered pumps.

In accordance with one exemplary embodiment, a tissue-engineered pump is provided. The tissue-engineered pump includes a housing, a tubular member comprising an engineered anisotropic muscle tissue and accommodated within the housing, the tubular member comprising an inlet portion, an outlet portion and a cavity disposed between the inlet portion and the outlet portion. The tissue-engineered pump also includes a first valve disposed at the inlet portion of the tubular member, the first valve configured to enable a fluid flow into the cavity of the tubular member through the inlet portion, and a second valve disposed at the outlet portion of the tubular member, the second valve configured to enable a fluid flow out of the cavity of the tubular member through the outlet portion. The tissue-engineered pump may include, in some embodiments, an energy source for stimulating a collection of cells within the engineered tissue to cause contraction of a volume of the cavity.

In accordance with another exemplary embodiment, a method is provided for forming a tissue-engineered pump. The method includes providing a housing, and providing a tubular member comprising an engineered anisotropic muscle tissue within the housing, the tubular member comprising an inlet portion, an outlet portion, and a cavity disposed between the inlet portion and the outlet portion. The method also includes disposing a first valve at the inlet portion of the tubular member, the first valve configured to enable a fluid flow into the cavity of the tubular member through the inlet portion, and disposing a second valve at the outlet portion of the tubular member, the second valve configured to enable a fluid flow out of the cavity of the tubular member through the outlet portion. The method may include, in some embodiments, coupling the tubular member to an energy source for stimulating a collection of cells within the engineered tissue to cause contraction of a volume of the cavity.

In accordance with another exemplary embodiment, a tissue-engineered pump is provided. The tissue-engineered pump includes a housing, and a conical member accommodated within the housing, the conical member comprising a rounded tip and a side wall cooperatively enclosing a cavity, wherein the rounded tip comprises an engineered circumferential muscle tissue, and wherein the side wall comprises an engineered anisotropic muscle tissue. The tissue-engineered pump includes a first valve coupled to the conical member for enabling a fluid flow into the cavity of the conical member, and a second valve coupled to the conical member for enabling a fluid flow out of the cavity of the conical member. The tissue-engineered pump may include, in some embodiments, an energy source for stimulating a collection of cells within the engineered tissue to cause contraction of a volume of the cavity.

In accordance with another exemplary embodiment, a method is provided for forming a tissue-engineered pump. The method includes providing a housing, and providing a conical member within the housing, the conical member comprising a rounded tip and a side wall cooperatively enclosing a cavity, wherein the rounded tip comprises an engineered circumferential muscle tissue, and wherein the side wall comprises an engineered anisotropic muscle tissue. The method also includes coupling a first valve to the conical member for enabling a fluid flow into the cavity of the conical member, and coupling a second valve to the conical member for enabling a fluid flow out of the cavity of the conical member. The method may include, in some embodiments, coupling the conical member to an energy source for electrically stimulating a collection of cells within the engineered tissue to cause contraction of a volume of the cavity.

In accordance with another exemplary embodiment, a tissue-engineered pump is provided. The tissue-engineered pump includes a housing, and a first fluid pumping member comprising an engineered anisotropic muscle tissue and accommodated within the housing, the first fluid pumping member comprising at least one side wall defining a first cavity therein for holding a fluid. The tissue-engineered pump also includes a first valve coupled to the first fluid pumping member and configured to enable a fluid flow into the first cavity, and a second valve coupled to the first fluid pumping member and configured to enable a fluid flow out of the first cavity.

In accordance with another exemplary embodiment, a tissue-engineered cardiac valve is provided. The tissue-engineered valve includes a polymeric fiber scaffold configured as a hollow tubular member including a plurality of leaflets, and a collection of cells, such as, umbilical endothelial cells seeded onto the leaflets of the polymeric fiber scaffold.

In accordance with another exemplary embodiment, a method is provided for forming a tissue-engineered cardiac valve. The method includes providing a cylindrical mandrel including sinuses for valve constructs. The method also includes rotating a reservoir containing a polymer in proximity to the mandrel, wherein rotation of the reservoir ejects the polymer from the reservoir to form micron, submicron or nanometer dimension polymeric fibers. The method also includes depositing the polymeric fibers on a surface of the mandrel, thereby forming a polymeric fiber scaffold, the polymeric fiber scaffold configured as a hollow tubular member including a plurality of valve constructs.

In accordance with another exemplary embodiment, a method is provided for forming a tissue-engineered cardiac valve. The method includes providing a cylindrical mandrel including sinuses for valve constructs. The method also includes rotating a rotating structure such that it contacts a surface of a liquid material (e.g., a polymer) on a platform to impart sufficient force or energy to create a meniscus at the location where the rotating structure contacts the surface. The force or energy imparted by the rotating structure overcomes the surface tension and decouples a portion of the liquid material at the meniscus and flings the portion away from the contact with the rotating structure and from the platform, thereby forming a micron, submicron and/or nanometer dimension fiber. The method also includes depositing the polymeric fibers on a surface of the mandrel, thereby forming a polymeric fiber scaffold, the polymeric fiber scaffold configured as a hollow tubular member including a plurality of valve constructs.

BRIEF DESCRIPTION OF THE DRAWINGS

FIGS. 1A-1G depict the key concepts of fluid transport in jellyfish and in vitro implementation. (a) Schematics of jellyfish stroke cycle generating thrust during the power stroke, and feeding currents during the recovery stroke. (b) Controlled configurational change. Symmetric, complete bell contraction is mediated by anisotropic striated muscle tissue, a functional syncytium synchronized by a system of distributed neuronal pacemaker centers (jellyfish, top). This mechanism can be approximated by electrical field stimulation of electromechanically coupled, anisotropic cardiac muscle (medusoid, bottom). In either case, lobed geometry facilitates circumferential constriction of the bell. (c) Stroke kinematics. In the bilayered design of jellyfish (top) and medusoid (bottom), a flexible elastomer opposes an actuator, which promotes asymmetric stroke patterns: active, fast contraction and passive, slow recoil. (d) Fluid dynamics. Fluid velocity gradients, so-called boundary layers, extend effective reach of lobes (top). Overlapping boundary layers close interlobate gaps to oncoming flow. This prevents leakage and inefficient fluid transport despite the presence of gaps (center). Optimized medusoid body geometry favors the formation of boundary layer overlap and thus efficient fluid transport (bottom). (e) Body design of jellyfish (top) and free-swimming medusoid construct (bottom). Comparison demonstrates similar geometry and dimensions but also illustrates that the medusoid constitutes a simplified version of a jellyfish, reduced to elements necessary for propulsive function. (f) Jellyfish 2D muscle architecture (top) was reverse-engineered in medusoids (bottom). Left: Composite brightfield image overlaid with F-actin stain (light gray) of muscle cell monolayer. Square inset: Close-up on muscle organization at lobe-body junction; F-actin stain (light gray). Note that jellyfish muscle tissue consists of a single layer of myofibrils, here in focus, whereas engineered medusoid muscle tissue contains a stack of myofibrils, most of them being out of focus and blurring the image at this resolution. Circular inset: microstructure of single myofibril layer; F-actin stain (light gray), sarcomeric α-actinin (gray). (g) Distribution of actin fiber orientation angles within single myofibril layer (centered on zero). Quantitative analysis of multiple fields of view revealed no significant difference in the orientation organization parameter (OOP) (P=0.61, n=10; two-sample t-test).

FIGS. 6A-6F depict the jellyfish-inspired Medusoid muscle and body design. a, Muscle architecture in juvenile jellyfish showing radial and circular fiber orientations. Note: Composite image generated from single stained lobe copied and rotated to eight positions around central axis to extrapolate musculature of "entire" animal. White: F-actin stain. b, Biomimetic Medusoid muscle layout based on late-stage ephyrae. c, Final optimized Medusoid body and muscle layout with radial and circular fiber orientations. d, Suboptimal Medusoid design promoting inefficient fluid interactions ("sieve design"). e, Close-up on junction of radial and circular muscle in jellyfish. f, Close-up on junction of radial and circular muscle in Medusoid. Note: This tissue was micropatterned using 20 μm wide lines spaced by 20 μm to emphasize longitudinal edges and improve pattern visibility. Final constructs were patterned with 22 μm wide lines separated by 4 μm gaps resulting in confluent anisotropic tissue (FIG. 1f).

FIGS. 8A-8D depict the processing steps of quantitative fiber alignment analysis. a, Original actin stain intensity image. b, Binary image mask with black regions indicating regions exempted from analysis. c, Detail of intensity image overlaid with local vector field showing tangential vector d, Histogram of all orientation vector angles, peaking at dominant fiber orientation. The corresponding orientational order parameter (OOP) is 0.9587.

FIGS. 9A-9F depict the medusoid fabrication process. a, Titanium casting molds and PDMS micropatterned stamps fabricated from photolithographed silicon wafers provided templates for Medusoid body shape and muscle layout, respectively. b, Medusoid substrates were fabricated by spin-coating the titanium casting mold with PIPAAm for temperature-sensitive adhesion to a PDMS top layer. Using PDMS stamps the PDMS layer was micropatterned with fibronectin to elicit cell adhesion and the formation of anisotropic Medusoid muscle tissue. c, Substrates were seeded with a suspension of freshly isolated neonatal rat cardiomyocytes. d, Medusoid substrates were cultured for four days to allow for maturation of the 2D myocardium. e, Lowering bath temperatures below 35° C. dissolved the layer of PIPAAm, allowing to gently peel off the Medusoid from the titanium mold. f, The free-floating Medusoid was assayed for bell contraction and fluid transfer mimicking jellyfish feeding and swimming.

FIGS. 11A-11J depict the fluid-solid interaction and optimal Medusoid geometry. a, Medusoid geometric parameters. Free parameters: relative lobe length=inner to outer diameter, and lobe divergence=outer to inner lobe width. Fixed parameters: Outer diameter=9 mm, number of lappets=8. b, Viscous boundary layer model describing velocity gradient at solid-fluid interfaces. Thickness of boundary layer is proportional to $Re^{-1/2}$, with Re=local Reynolds number. c, Given suitable Medusoid geometry and flow conditions, overlap of neighboring boundary layers may occur, blocking interlobal gaps to oncoming flow. This raises both viscous and pressure drag, leading to synergistic increase in lobe drag and paddling efficiency (right) compared to the case of insufficient boundary layer overlap with interlobal leakage (left). d, Optimal Medusoid geometries (center) promote sufficient boundary layer overlap, thereby minimizing leakage through interlobal gaps (left), and avoid instable or interfering lobe dimensions (right). e, Bell drag was estimated from simple fluid-solid interaction model. Medusoid lobes were represented as continuous arrays of elliptical cylinders perpendicular to flow. f, At each radial position, geometric and kinetic parameters are given from overall geometry and flow conditions, allowing to derive local porosity, Reynolds number and reference area. g, Local Reynolds number and porosity predict local drag coefficient. h, Empirical validation of the model was achieved by sinking acrylic Medusoid dummies of varying geometries in glycerol-water solutions. Drag factors were calculated from terminal sinking velocity. i, Empirical order of drag factors in Medusoid dummies was consistent with predicted order (right), and independent of the order of average lobe Reynolds numbers (left). Drag factors were normalized to respective maximal value. Color code relates dummy shapes depicted in (i) with plotted data. j, Total predicted drag as function of relative lobe length and divergence in live Medusoid tissue constructs. In general, higher lobe divergence resulted in higher maximal drag. For stability reasons lobe divergence did not exceed 1.8. Final optimal and suboptimal designs promoting paddling and sieving, respectively, are depicted to the left.

FIGS. 12A-12E depict the digital particle image velocimetry (DPIV) setup and analysis. a, Basic DPIV set-up for jellyfish and Medusoids. A laser light beam is directed through a plano-concave cylindrical lens and thereby diverges into a light sheet of about 1 mm in thickness. This light sheet illuminates a plane within the particle-seeded fluid, thereby visualizing fluid motion in a single plane. b, Top-view onto plane of illuminated particles as seen by video camera. For flow analysis the field is divided into subsample areas, so-called interrogation windows. c, Each interrogation window is compared at time 1 (t1) with the corresponding area at time 2 (t2) in the following video frame. The average velocity vector for the window corresponds to the shift of particle positions at t1 that results in matching most of the particle positions at t2, equal to peak cross-correlation between positions at t1 and t2. d, The flow field is derived by plotting the average velocity vector for all windows in the field of view. Further analysis on the flow yields metrics such as vorticity (light gray: clockwise; medium gray: anti-clockwise) or the velocity profile across a line of reference (Ref. line). e, The non-dimensionalized velocity profile as a function of position is derived from the normal component of the velocity vectors across the line of reference. Here, the line of reference was chosen to be the diameter of the stopping vortex ring, allowing the characterization of flow towards the subumbrella at a certain instant during the recovery stroke ("feeding currents").

FIG. 16A depicts an exemplary tissue-engineered pump.

FIG. 16B is a photograph of a super-aligned biodegradable polycaprolactone (PCL) nanofiber scaffold fabricated by RJS.

FIG. 16C is a scanning electron micrograph showing microscale alignment of nanofibers in the scaffold in panel FIG. 16D is a scanning electron micrograph of cardiac myocytes seeded onto aligned RJS nanofibers. Cardiac myocytes seeded onto RJS nanofibers align with microscale features of the fibers to build anisotropic cardiac tissue in vitro.

FIG. 16E is a confocal maximum projection immunostained image of engineered anisotropic cardiac muscle tissue on RJS fabricated biodegradable polylactic acid (PLA) nanofibers. Cell nuclei are stained in light gray and α-actinin at the sarcomeric Z-lines is stained medium gray.

DETAILED DESCRIPTION

The present invention is based, at least in part, on the production and assembly of synthetic muscular pumps. Accordingly, the present invention provides tissue-engineered pumps that more accurately mimic the function of a real heart without the need for a pump generated by a motor, or can be used to locally improve the circulation in a subject in need thereof, such as a diabetic subject having poor foot and/or leg circulation, methods of fabricating such pumps, and methods of use of such pumps. The present invention also provides tissue-engineered valves, methods of fabricating such valves, and methods of use of such valves.

I. Tissue Engineered Pumps and Valves

In one aspect, the present invention provides one or more tissue-engineered pumps for pumping a fluid. Certain exemplary embodiments are illustrated in and described in connection with FIGS. 13, 14 and 17. In some embodiments, a single pump may be fabricated and used to pump a fluid. In some other embodiments, a plurality of pumps (illustrated in FIG. 14, for example) may be configured and used in conjunction within a system to pump a fluid.

Figure 13:
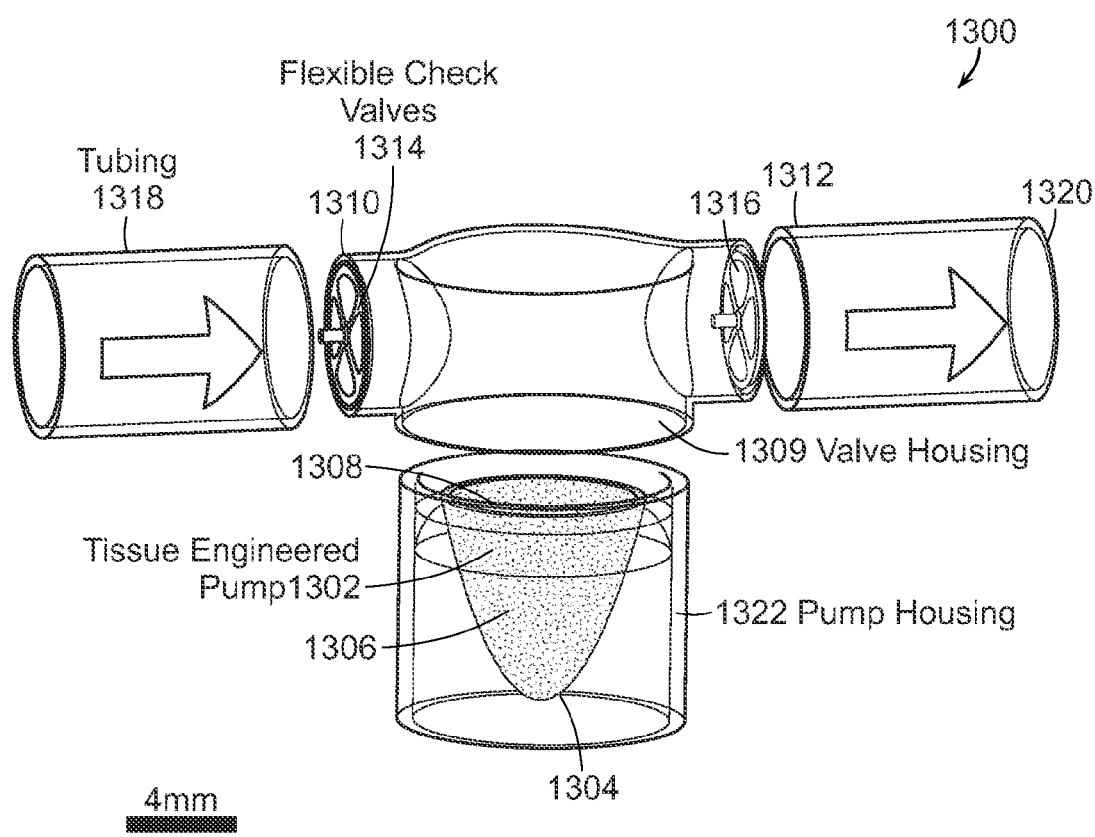
FIG. 13 depicts an exemplary tissue-engineered pump device of the invention.

FIG. 13 illustrates a tissue-engineered muscular pump system 1300 including a substantially hollow conical member 1302 having an internal cavity. The conical member 1302 may have a rounded closed tip 1304 at the bottom, a substantially conical side wall 1306 and an open top surface 1308. In some embodiments, the conical member 1302 may have the structure, size, operation and function of a chamber, such as a ventricle, of a mammalian heart (e.g., a human heart, a pig heart, and the like). The conical member 1302 may be configured to have any suitable dimensions and size. An exemplary conical member 1302 may have a length ranging from about 0.2 mm to about 200 mm, and a top surface diameter of about 0.2 mm to about 200 m, but is not limited to these exemplary ranges.

Figures 20B, 20C:
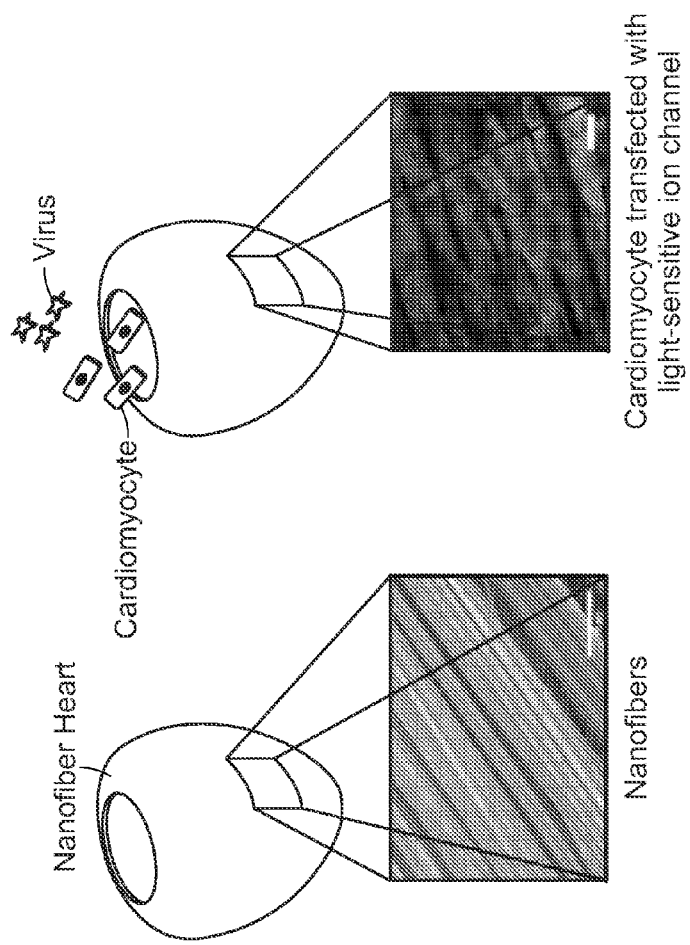
FIGS. 20A-20C depict an exemplary fabrication method of an optically stimulated tissue-engineered pump. A-B) An anisotropic scaffold with micron, submicron, or nanometer dimension polymeric fibers is fabricated on a spinning heart shaped mandrel using the RJS system. C) An anisotropic cardiac tissue is formed on the scaffold by seeding cardiac muscle cells. In addition, for optical stimulation, gene transfection methods (e.g. viral transfection, chemical-based transfection, electroporation, and so on) introduce light-sensitive ion channels into cardiac tissue with are optically activated to generate an action potential through the tissue.
Figure 20A:
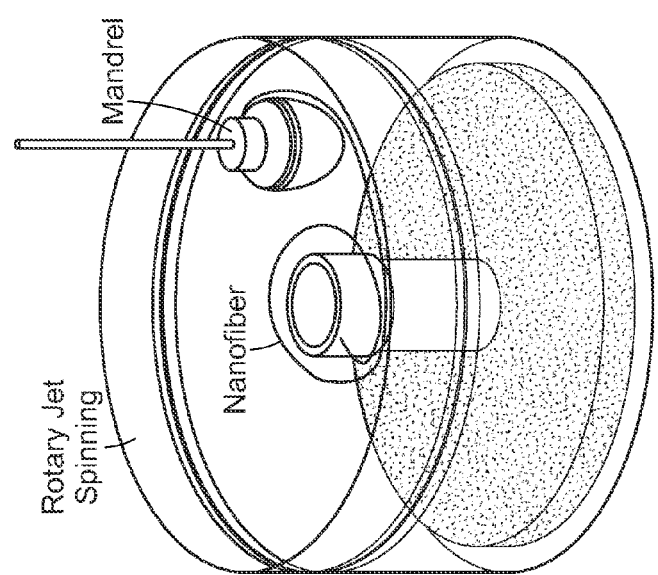

The engineered muscle tissue may be fabricated by forming a scaffold of micron, submicron or nanometer dimension polymeric fibers configured in a conical shape, seeding muscle cells onto the polymeric fibers, and culturing the muscle cells to form a functional muscle tissue. The polymeric fibers may be formed as described herein, for example, by ejecting a polymeric solution or liquid polymer out of a rotating reservoir and collecting the fibers onto the outside surface of a particularly configured collection device, e.g., a mandrel. An exemplary collection device illustrated in FIG. 20 may have a substantially conical structure for collecting polymeric fibers on its outside surface. Devices and methods to form micron, submicron or nanometer dimension polymeric fibers are described in more detail below.

The conical member 1302 may be a tissue-engineered structure that includes engineered muscle tissue. In an exemplary embodiment, the rounded trip 1304 of the conical member 1302 may include an engineered circumferential muscle tissue, and the side wall 1306 may include an engineered anisotropic muscle tissue, e.g., extending from the portion of the rounded tip to the open end in substantially straight lines. In this exemplary embodiment, the polymeric scaffold near the rounded tip may be formed by rotating the mandrel and moving it up and down. The polymeric scaffold for the side wall farther away from the rounded tip may be formed by depositing the fibers while moving the mandrel in an up and down motion to deposit a longitudinal layer of fibers, stopping the deposition, rotating the mandrel one time, start deposition while moving the mandrel in an up and down motion, and repeating this sequence until the entire outer surface of the mandrel is coated with the polymeric fibers to a desired thickness.

The conical member 1302 may be coupled to a valve housing 1309 including an inlet portion 1310 configured for fluid flow into the cavity and an outlet portion 1312 configured for fluid flow out of the cavity. A first valve 1314 may be disposed at or in the proximity of the inlet portion 1310 so that a fluid may flow into the cavity. A second valve 1316 may be disposed at or in the proximity of the outlet portion 1312 so that a fluid may flow out of the cavity. The first and/or second valves may be one-way check valves in some embodiments; two-way valves in certain other embodiments; leaky one-way valves in certain other embodiments; and the like. The first and second valves may be formed of any suitable material including, but not limited to, elastomer, biological tissue, and the like. In one embodiment, the valves may be tissue-engineered using a polymeric scaffold seeded with cells. In some embodiments, the polymeric scaffold may be formed by ejecting a polymeric solution or liquid polymer out of a rotating reservoir and collecting the fibers onto the outside surface of a particularly configured collection device, e.g., a mandrel.

In some embodiments, an inlet tubing 1318 may be provided at the first valve 1314 to enable a fluid flow into the first valve, and an outlet tubing 1320 may be provided the second valve 1316 to enable a fluid flow out of the second valve. The inlet and outlet tubings may be formed of any suitable material including, but not limited to, elastomer, biological tissue, and the like.

In some embodiments, the pump system 1300 may be provided in a housing 1322. The housing may be formed of any suitable rigid or semi-rigid material including, but not limited to, an elastomer, a plastic, a metal, a ceramic, or a combination thereof, and the like. In in vivo applications, the pump system 1300 may be provided in an animal body.

Figure 21:
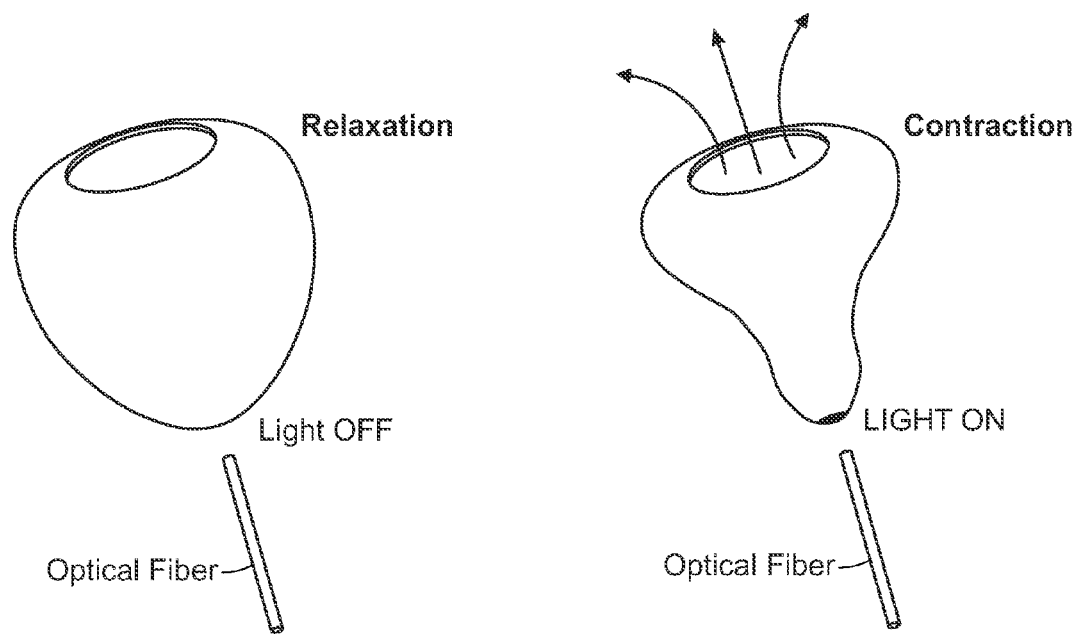
FIG. 21 depicts an exemplary optical stimulation method. The light pattern introduced by an optical fiber (or micromirror array) can stimulate portion of cardiac tissue that is transfected with light sensitive ion channels (e.g., Channelrhodopsin-2 (ChR2), Halorhodopsin(NpHR), C1V1, step function opsins (SFOs)). The induced action potential of the optical stimulated tissue can propagate and activate the remaining cells of the tissue through gap junctions.
Figure 22:
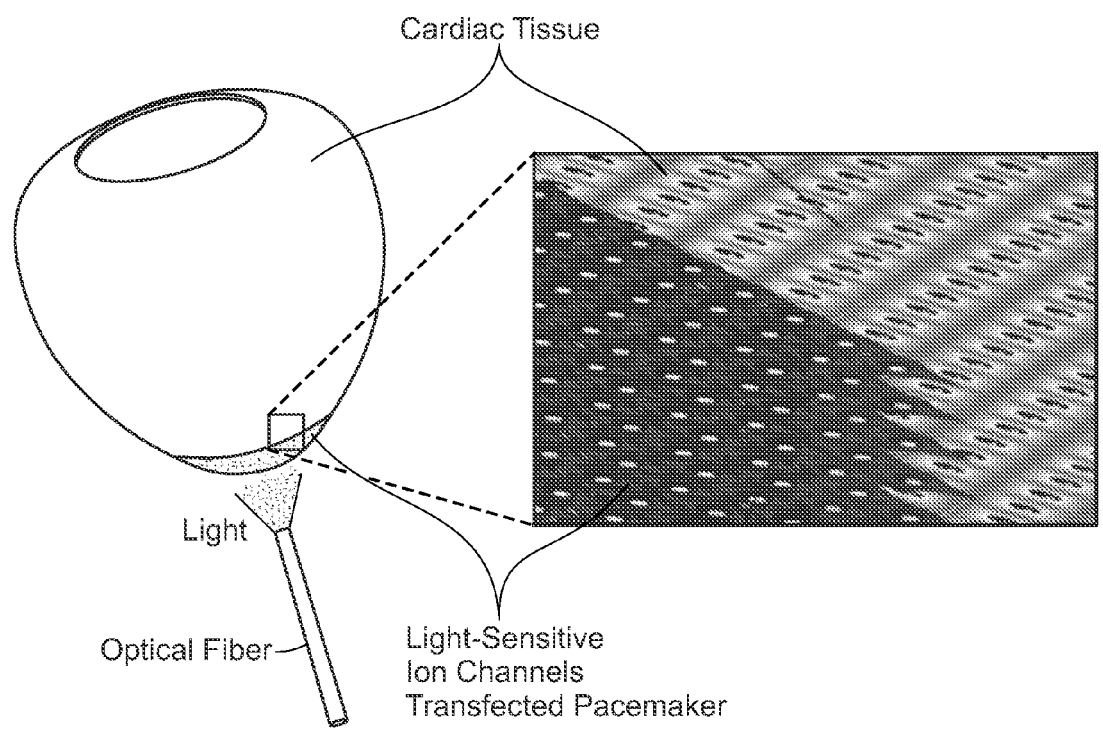
FIG. 22 depicts an exemplary optical stimulation method using a heterogeneous cell population. Light stimulates a tissue-engineered pacemaker that is transfected with light-sensitive ion channels. The induced action potential of the optical stimulated pacemaker propagates and activates the remaining non-transfected tissue through gap junctions. A light-sensitive ion channel transfected pacemaker can be partially created on a scaffold as described herein, using various patterning techniques (e.g. virus patterning techniques and cell patterning techniques).

In use, a fluid may be provided in the cavity of the conical member 1302 via the inlet tubing 1318 and the first valve 1314. An energy source (e.g., a source of light and/or electrical energy) may be used to stimulate a collection of cells in the muscle tissue in the conical member 1302 so that the cells propagate an action potential and the engineered tissue contracts. The contraction of the tissue may cause a peristaltic motion in the conical member 1302 and may contract the internal volume of the cavity of the conical member 1302. This contraction may cause the fluid to be pumped out of the cavity through the second valve 1316. FIG. 21 illustrates an exemplary conical member in a relaxed state and in a contracted state.

In some exemplary muscular pumping systems, a plurality of pumps as illustrated in FIG. 13 may be coupled together to enable their operation in series and/or in parallel. For example, in a serial configuration, an outlet portion of a first conical member may be coupled to an inlet portion of a second conical member so that fluid pumped by the first conical member flows into the second conical member and may, in turn, be pumped by the second conical member.

Figure 14:
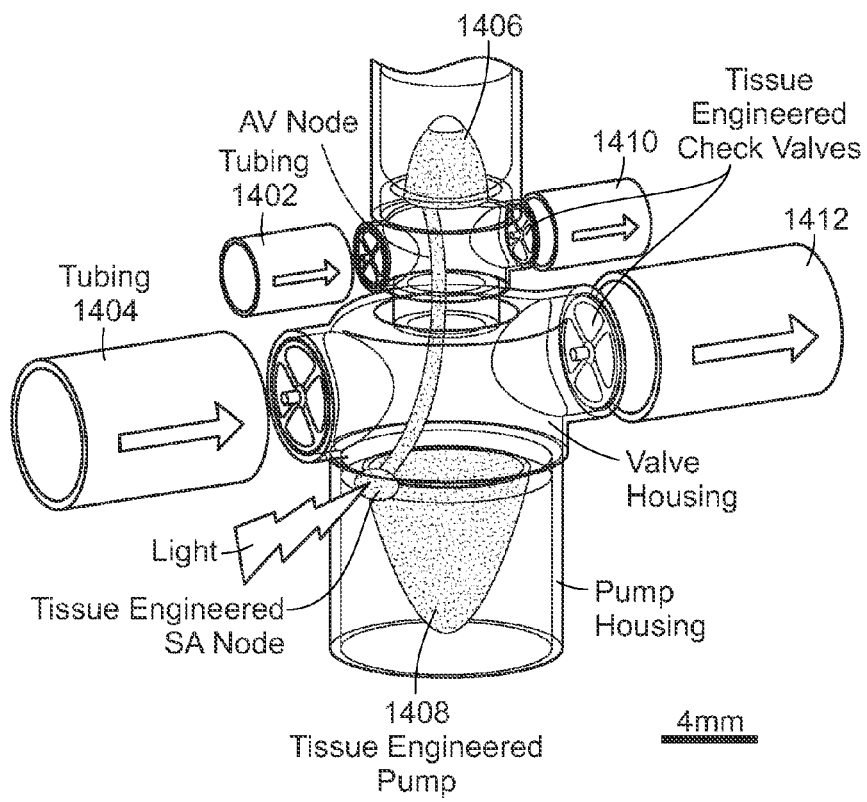
FIG. 14 depicts a CAD drawing of an exemplary tissue-engineered pump device including two pump assemblies in parallel.

In an exemplary parallel configuration illustrated in FIG. 14, inlet portions 1402, 1404 of first and second conical members 1406, 1408, may be coupled to a common inlet conduit so that fluid may be pumped into both conical members concurrently. Similarly, outlet portions 1410, 1412 of the first and second conical members 1406, 1408 may be coupled to a common outlet conduit so that fluid may be pumped out of both conical members concurrently. An energy source may be used to electrically and/or optically stimulate, for example, the SA/AV nodes of the conical members 1406, 1408. In some embodiments, the SA/AV of the conical members may be coupled so that excitation of one conical member automatically excites the other.

One of ordinary skill will recognize that more than two conical members may be coupled in other serial and/or parallel configurations.

Figure 17:
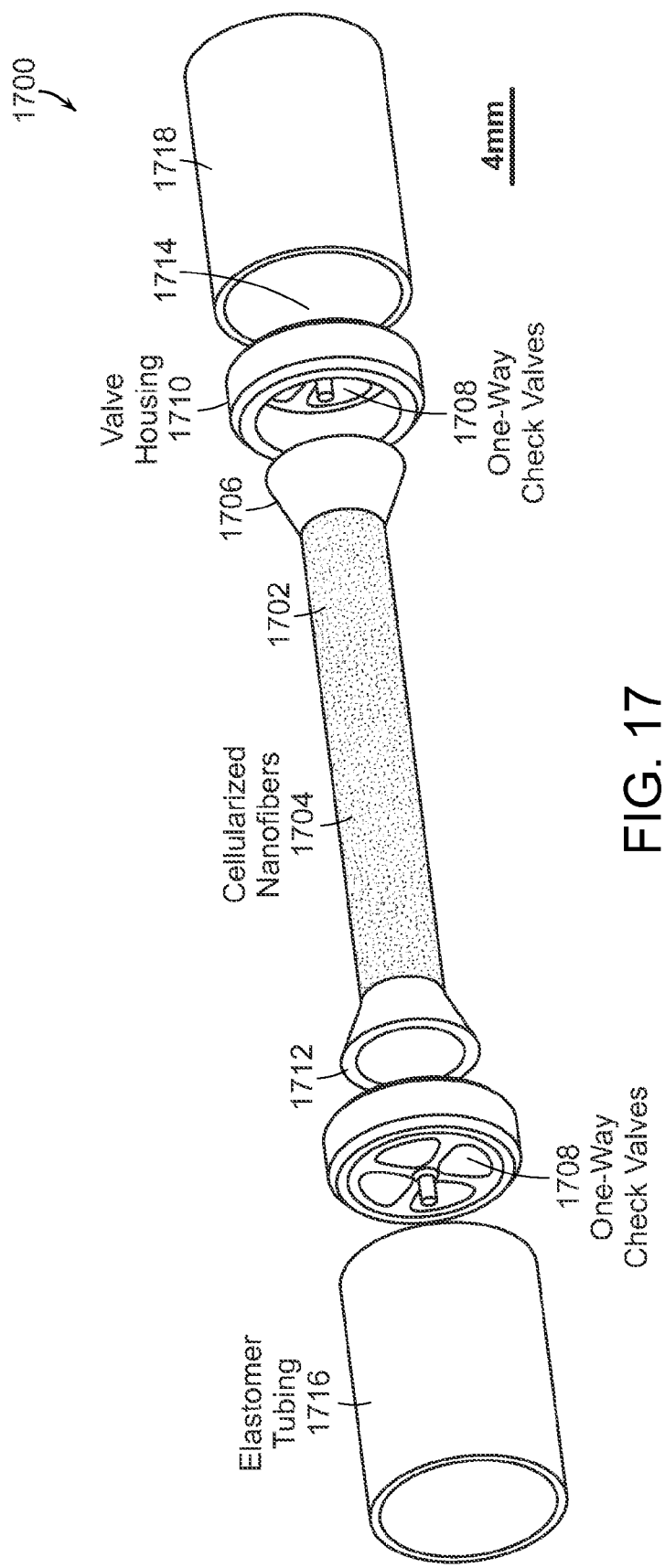
FIG. 17 depicts an exemplary tissue-engineered pump device of the invention.
Figure 18A:
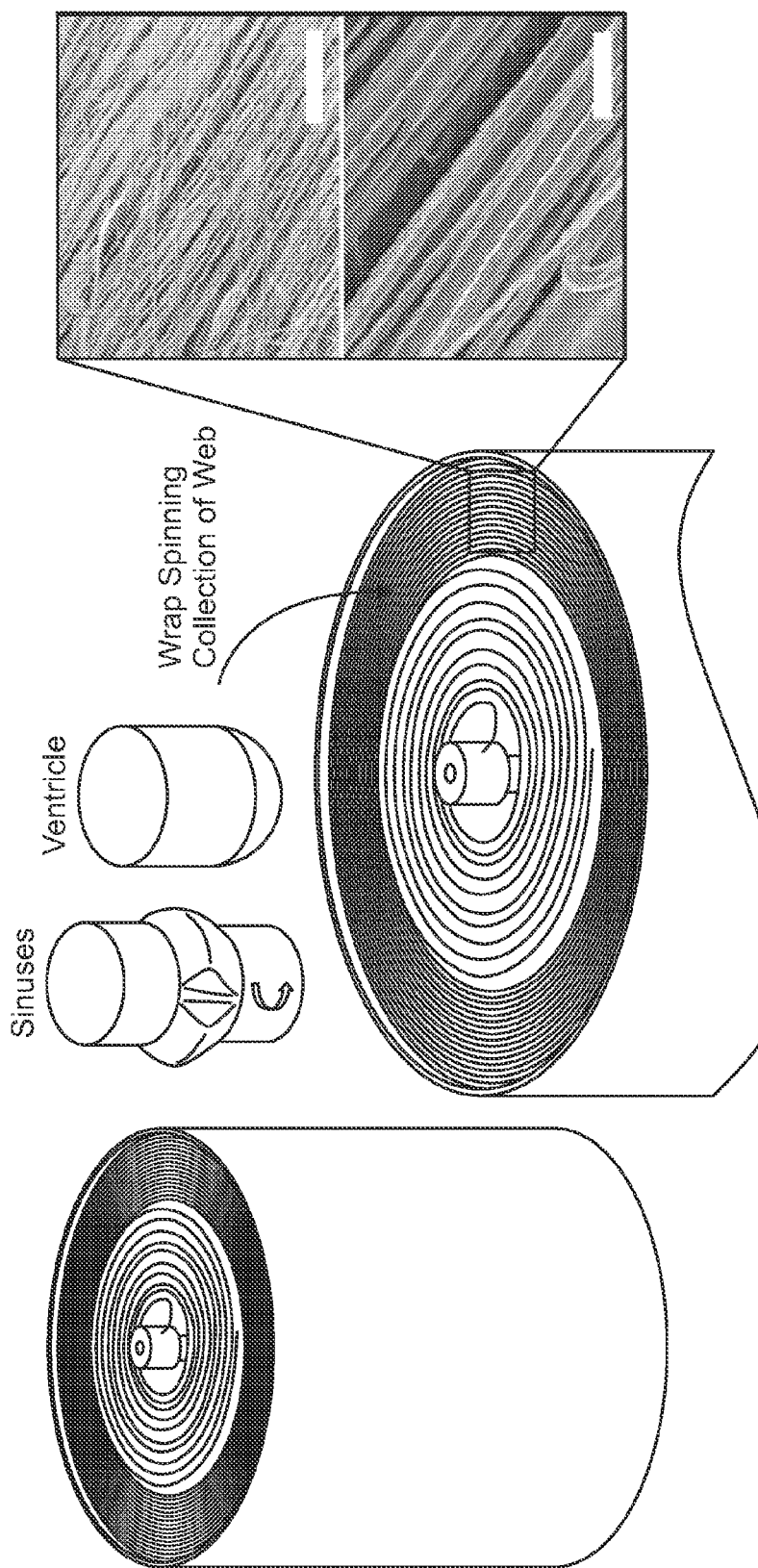
FIGS. 18A-18C depict the generation of scaffolds suitable for fabricating a tissue engineered pump using the Rotary Jet Spinning (RJS) system. Aligned polymer and/or protein fibers can be extruded and (A) collected onto custom made mandrels, for example a cylindrical mandrel with sinuses for semilunar valve constructs or dome shaped mandrels for ventricle constructs (scale bar 20 μm top inset, 2 μm bottom inset). Once spun onto mandrels and dried, (B) semilunar valve conduits can be made by suturing, gluing, or point melting scaffold leaflets within the sinus conduit and resealed to mimic native geometry (polycaprolactone nanofibers used to produce conduit and valve, native images from Manghat et al, Heart; 2005). (C) Nanofibers are similarly be spun onto dome shaped mandrels to produce tissue engineered ventricles or onto flat mandrels to produce sheets (pure gelatin nanofibers).
Figure 18C:
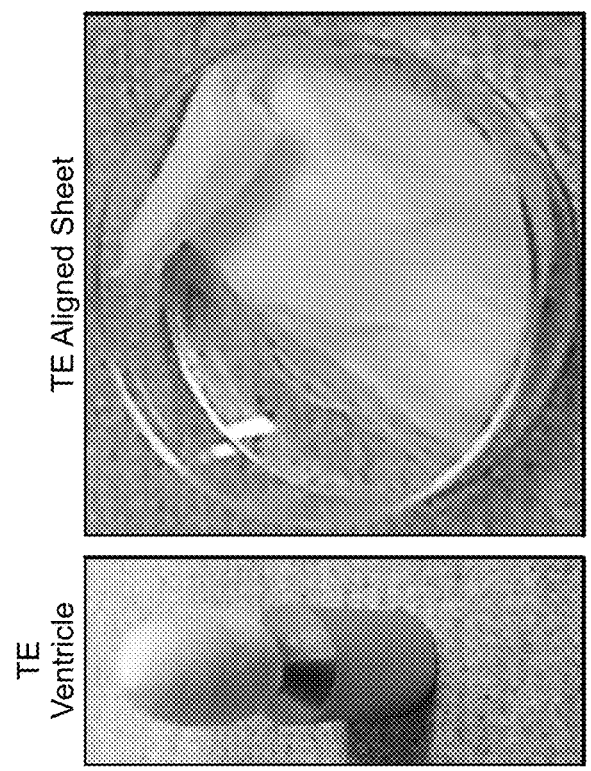
Figure 18B:
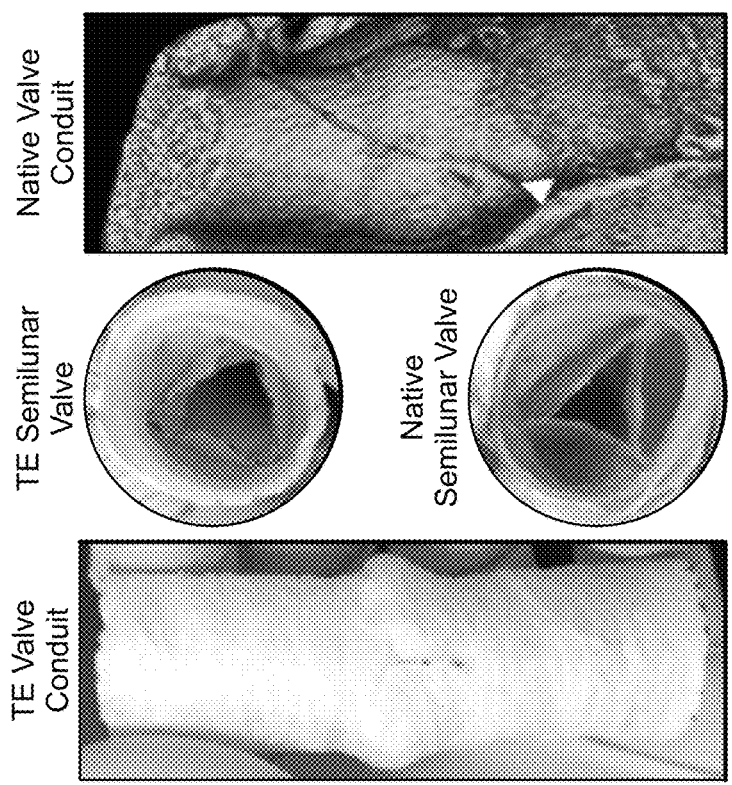
Figure 19A:
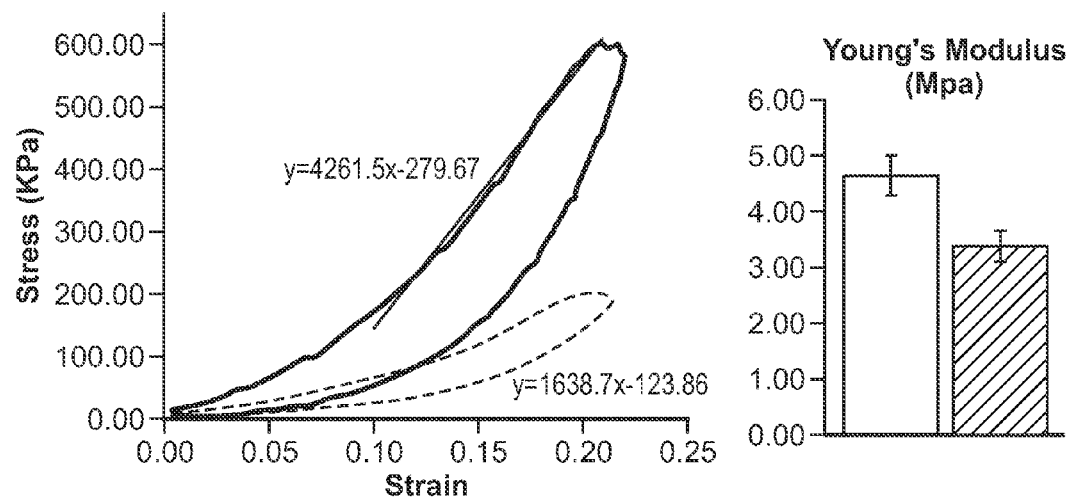
FIGS. 19A-19D depict the characterization of Cardiac Scaffolds. (A) representative equibiaxial stress versus strain plot of 4:1 polycaprolactone:collagen scaffold and average stiffness measured at the linear region of the stretch curves (parallel to fiber direction: black; perpendicular to fiber direction: dashed; n=9). (B) Valve interstitial cells align in the fiber direction of the scaffold (scale bar=25 μm; medium gray: nucleus, white: actin). Semilunar valve constructs can be functionally tested in a pulse duplicator system (C); after 24 hour of equilibration, flow through and pressures acting on the scaffold can be measured (one pulse cycle show). Pure protein or synthetic scaffolds can be produced; however, hybrid scaffolds may be advantageous for both biocompatibility and strength. (D) Imaging FTIR of polycaprolactone/collagen fiber bundles shows uniform composition of fiber bundles after 24 hours soaking in 37° C. water demonstrating that the hybrid composition eliminates the need to crosslink protein fibers which are normally water soluble (characteristic peak of PCL: Carbonyl Stretch, characteristic peak of collagen: Amides I and II; scale bar 30 μm).
Figure 19B:
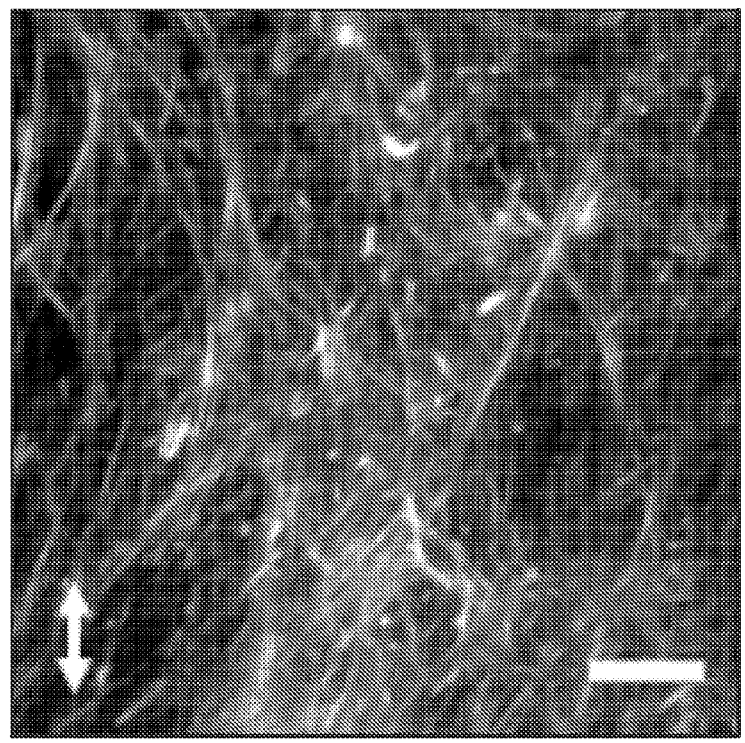
Figure 19C:
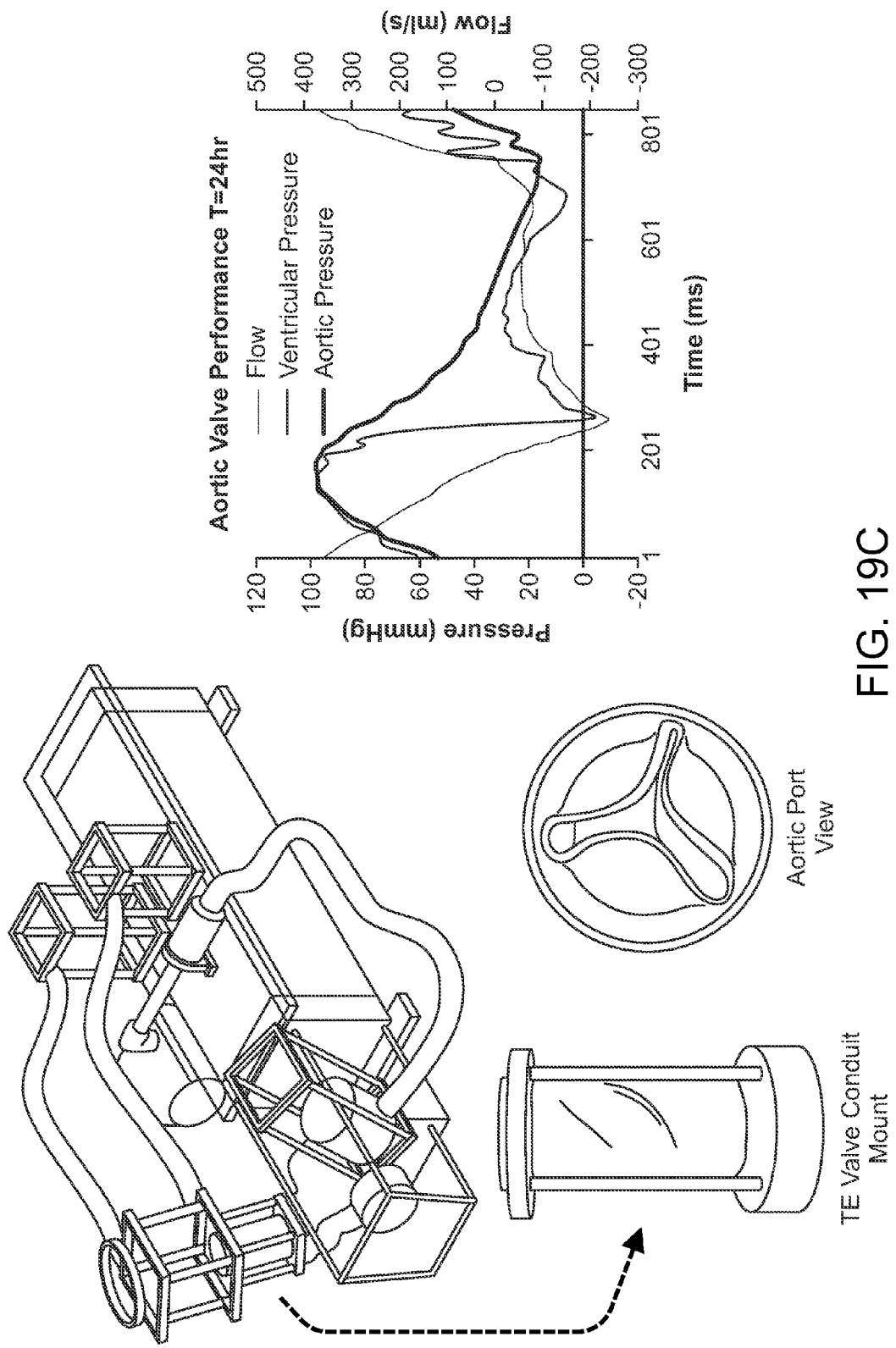
Figure 19D:
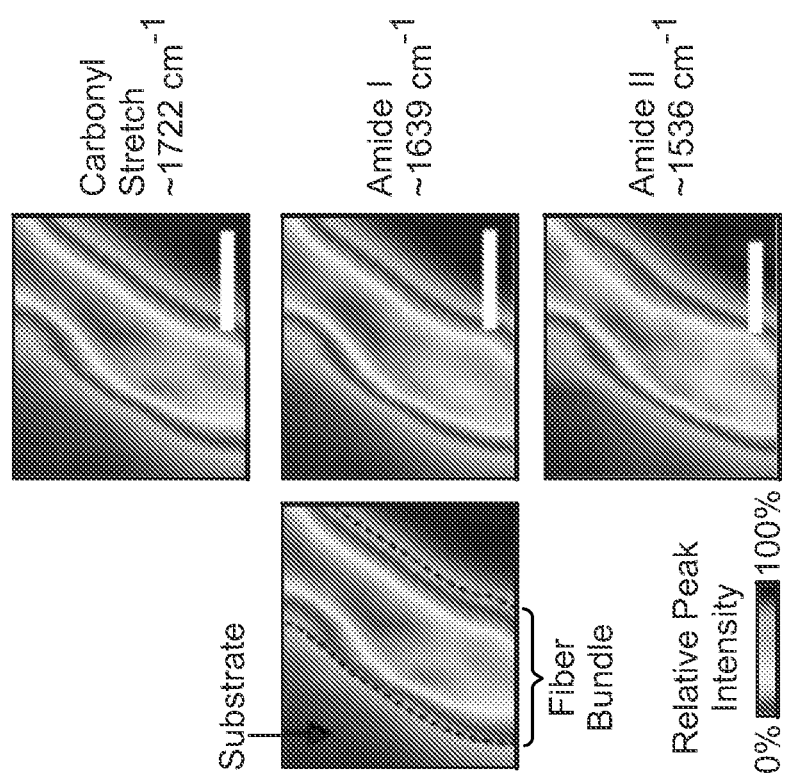

FIG. 17 illustrates a tissue-engineered muscular pump system 1700 including a substantially hollow tubular member 1702 having an internal cavity. In some embodiments, the tubular member 1702 may have the structure, size, operation and function of a component of a mammalian cardiovascular system (e.g., a pumping chamber or a conduit of a heart or a blood vessel). An exemplary tubular member 1702 may have a diameter ranging from about 0.2 mm to about 200 mm (e.g., about 0.2, 0.3, 0.4, 0.5, 0.6, 0.7, 0.8, 0.9, 1, 2, 3, 4, 5, 6, 7, 8, 9, 10, 20, 25, 30, 35, 40 4, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200 mm), and a length of about 0.2 mm to about 200 mm (e.g., about 0.2, 0.3, 0.4, 0.5, 0.6, 0.7, 0.8, 0.9, 1, 2, 3, 4, 5, 6, 7, 8, 9, 10, 20, 25, 30, 35, 40 4, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200 mm). Ranges, diameters, and lengths intermediate to the above recited ranges, lengths and diameters are also contemplated by the present invention.

The tubular member 1702 may be a tissue-engineered structure that includes engineered muscle tissue. The engineered muscle tissue may be fabricated by forming a polymeric scaffold of micron, submicron or nanometer dimension polymeric fibers configured in a tubular shape, seeding muscle cells onto the polymeric fibers, and culturing the cells to form a functional muscle tissue.

In exemplary embodiments, the polymeric fibers may be uniformly or helically wrapped onto the outside surface of a cylindrical collection device to form the tubular member 1702. The polymeric fibers may be formed as described herein, for example, by ejecting a polymeric solution or liquid polymer out of a rotating reservoir and collecting the fibers onto the outside surface of a particularly configured collection device, e.g., a mandrel, that is rotating and moving vertically up and down. In some cases, the collection device may aligned along or at an angle relative to its rotational axis. In an exemplary embodiment, the collection device, e.g., a mandrel, may be configured as a tubular structure that collects polymeric fibers on its outer surface. As the tubular collection device rotates, the polymeric fibers formed by ejection from the reservoir wraps around the collection device. As the tubular collection device moves linearly and vertically up and down, the wrapped polymeric fibers extend longitudinally along the collection device to form a tubular polymeric scaffold. In some cases, the collection device may be aligned so that its rotational axis (axis of symmetry) is at an angle to the vertical axis.

The tubular member 1702 includes an inlet portion 1704 configured for fluid flow into the cavity and an outlet portion 1706 configured for fluid flow out of the cavity. A first valve 1708 may be disposed at or in the proximity of the inlet portion 1704 so that a fluid may flow into the cavity. A second valve 1710 may be disposed at or in the proximity of the outlet portion 1706 so that a fluid may flow out of the cavity. The first and/or second valves may be one-way check valves in some embodiments; two-way valves in certain other embodiments; leaky one-way valves in certain other embodiments; and the like. In some embodiments, the first and second valves may each be provided in a valve housing 1712, 1714. The first and second valves may be formed of any suitable material including, but not limited to, elastomer, biological tissue, and the like. In one embodiment, the valves may be tissue-engineered using a polymeric scaffold seeded with cells. In some embodiments, the polymeric scaffold may be formed as described herein, for example, by ejecting a polymeric solution or liquid polymer out of a rotating reservoir and collecting the fibers onto the outside surface of a particularly configured collection device, e.g., a mandrel.

In some embodiments, an inlet tubing 1716 may be provided at the first valve 1708 to enable a fluid flow into the first valve, and an outlet tubing 1718 may be provided the second valve 1710 to enable a fluid flow out of the second valve. The inlet and outlet tubings may be formed of any suitable material including, but not limited to, elastomer, biological tissue, and the like.

In some embodiments, the pump system 1700 may be provided in a housing. The housing may be formed of any suitable rigid or semi-rigid material including, but not limited to, an elastomer, a plastic, a metal, a ceramic, or a combination thereof, and the like. In in vivo applications, the pump system 1700 may be provided in an animal body.

In use, a fluid may be provided in the cavity via the inlet tubing 1716 and the first valve 1708. An energy source (e.g., a source of light and/or electrical energy) may be used to stimulate a collection of cells in the muscle tissue in the tubular member 1702 so that the cells propagate an action potential and the engineered tissue contracts. The contraction of the tissue may cause a peristaltic motion in the tubular member 1702 and may contract the internal volume of the cavity of the tubular member 1702. This contraction may cause the fluid to be pumped out of the cavity through the second valve 1710.

In some exemplary muscular pumping systems, a plurality of pumps as illustrated in FIG. 17 may be coupled together to enable their operation in series and/or in parallel. For example, in a serial configuration, an outlet portion of a first tubular member may be coupled to an inlet portion of a second tubular member so that fluid pumped by the first tubular member flows into the second tubular member and may, in turn, be pumped by the second tubular member. In an exemplary parallel configuration, inlet portions of first and second tubular members may be coupled to a common inlet conduit so that fluid may be pumped into both tubular members concurrently. Similarly, outlet portions of the first and second tubular members may be coupled to a common outlet conduit so that fluid may be pumped out of both tubular members concurrently. One of ordinary skill will recognize that more than two tubular members may be coupled in other serial and/or parallel configurations.

Figure 15:
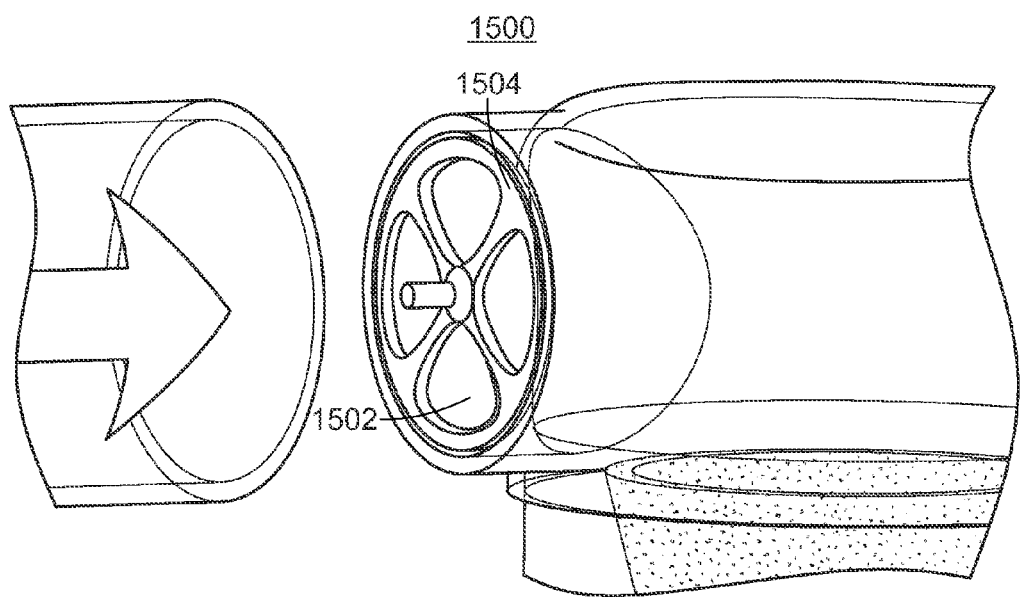
FIG. 15 depicts a CAD drawing of an exemplary valve assembly.

FIG. 15 is a schematic of an exemplary one-way valve assembly 1500 that may be used in a pump system provided in accordance with exemplary embodiments. The valve assembly 1500 may be disc-shaped and may be include a flexible material 1502, e.g., plastic. During use, the disc-shaped material of the valve deforms as fluid flows in one direction and is partially supported by an enclosure 1504 in the direction against fluid flow. As back-flow begins, the fluid presses the flexible material 1502 against the partially supported enclosure 1504, sealing the opening. In some embodiments, the valve assembly 1500 may have the structure, size, operation and function of a valve of a mammalian cardiovascular system (e.g., a bicuspid, a tricuspid, a semi-lunar, a venous valve). The valve assembly 1500 may be configured as a well-functioning valve or as a leaky valve.

In one embodiment, the present invention provides a tissue-engineered valve. In one embodiment, the tissue engineered valves of the present invention are configured as a hollow tubular member including a plurality of leaflets. The leaflets may be configured from a flat sheet of polymeric fibers and attached, e.g., glued, stitched. In another embodiment, the tissue engineered valves are configured on a cylindrical mandrel including sinuses for valve constructs (i.e., to form the leaflets). Umbilical endothelial cells, vascular endothelial cells, mesenchymal stem cells, primary valve harvest endothelial/interstitial cells, and the like, may be seeded on the scaffold including leaflets and cultured to form a functional valve tissue.

In one embodiment, the tissue-engineered valves of the invention comprise a scaffold of micron, submicron or nanometer dimension polymeric fibers configured in a tricuspid or mitral valve shape and engineered functional valve tissue. The engineered valve tissue may be fabricated by forming a scaffold of micron, submicron or nanometer dimension polymeric fibers configured in a valve shape, seeding cells onto the polymeric fibers, and culturing the cells to form a functional engineered valve tissue, i.e., induce unidirectional blood flow. The polymeric fibers may be formed as described herein, for example, by ejecting a polymeric solution or liquid polymer out of a rotating reservoir and collecting the fibers onto the outside surface of a particularly configured collection device, e.g., a mandrel.

As used herein, the term "engineered tissue" refers to a tissue generated in vitro which displays at least one physical characteristic typical of the type of the tissue in vivo; and/or at least one functional characteristic typical of the type of the tissue in vivo, i.e., is functionally active. For example, a physical characteristic of an engineered muscle tissue may comprise the presence of parallel myofibrils with or without sarcomeres aligned in z-lines (which may be determined based upon, for example, microscopic examination). A functional characteristic of an engineered muscle tissue may comprise an electrophysiological activity, such as an action potential, the ability to transmit an electrical signal to an adjacent cell, or biomechanical activity, such as contraction and/or the generation of force (which may be determined as described herein and in, for example, U.S. Pat. No. 8,492,150, U.S. Patent Publication Nos. 2011/0189719, 2012/0142556, and 2013/0046134, U.S. patent application Ser. No. 13/808,411, and PCT Publication No. WO 2013/086512, the entire contents of each of which are expressly incorporated herein by reference).

The term "anisotropic tissue", as used herein refers to tissues whose properties (e.g., electrical conductivity and/or elasticity) are dependent on the direction in which the properties are measured. Examples of tissues which are anisotropic (e.g., in vivo) include muscle, collagen, skin, white matter, dentin, nerve bundles, tendon, ligament, and bone. For example, large nerves are anisotropic, with all of the nerve fibers running parallel to one another. In addition, an anisotropic muscle tissue may exhibit high electrical conductivity when such a measurement is conducted in one particular direction but not another, or may exhibit a mechanical activity (e.g., contractility and/or elasticity) when such a measurement is conducted in one particular direction but not another.

The length of the tubular member may range from about 1 inch to about 24 inches, e.g., about 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 15.25, 15.5, 15.75, 16, 16.25, 16.5, 16.75, 17, 17.25, 17.5, 17.75, 18, 18.25, 18.5, 18.75, 19, 19.25, 19.5, 19.75, 20, 20.25, 20.5, 20.75, 21, 21.25, 21.5, 21.75, 22, 22.25, 22.5, 22.75, 23, 23.25, 23.5, 23.75, or about 24 inches. Lengths and ranges intermediate to the recited lengths and ranges are also contemplated by the present invention.

The outer diameter of the tubular member may range from about 0.5 mm to about 25 mm e.g., about 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 15.25, 15.5, 15.75, 16, 16.25, 16.5, 16.75, 17, 17.25, 17.5, 17.75, 18, 18.25, 18.5, 18.75, 19, 19.25, 19.5, 19.75, 20, 20.25, 20.5, 20.75, 21, 21.25, 21.5, 21.75, 22, 22.25, 22.5, 22.75, 23, 23.25, 23.5, 23.75, 24, 24, 25, 24.5, 24.75, or about 25 mm. Diameters and ranges intermediate to the recited diameters and ranges are also contemplated by the present invention.

The wall thickness of the tubular member may range from about 0.1 mm to about 2 mm, e.g., about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mm. Thicknesses and ranges intermediate to the recited thicknesses and ranges are also contemplated by the present invention.

The first valve may be a check valves, the second valve may be a check valve, or both the first and second valves may be check valves. In some embodiments, the valves are tissue engineered valves.

In another aspect, the present invention provides tissue-engineered pumps that include a housing, a conical member accommodated within the housing, the conical member comprising a rounded tip and a side wall cooperatively enclosing a cavity, wherein the rounded tip comprises an engineered circumferential muscle tissue, and wherein the side wall comprises an engineered anisotropic muscle tissue, a first valve coupled to the conical member for enabling a fluid flow into the cavity of the conical member, a second valve coupled to the conical member for enabling a fluid flow out of the cavity of the conical member; and an energy source for electrically a collection of cells within the engineered tissue to cause contraction of a volume of the cavity.

The tissue-engineered pump may further comprise a fluid provided in the cavity of the conical member and the contraction of the volume of the cavity pumps at least a portion of the fluid out of the cavity through the second valve.

In one embodiment, subsequent to the contraction, the volume of the cavity may expand to draw the fluid into the cavity through the first valve.

The height of the conical member may range from about 1 inch to about 6 inch, e.g., about 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, or about 6 inches. Heights and ranges intermediate to the recited heights and ranges are also contemplated by the present invention.

In one embodiment, the outer diameter of the conical member at its widest portion ranges from about 1 inch to about 4 inch, e.g., about 1, 1.25, 1.5, 1.75, 2, 2.25, 2.5, 2.75, 3, 3.25, 3.5, 3.75, or about 4 inches. Diameters and ranges intermediate to the recited diameters and ranges are also contemplated by the present invention.

In one embodiment, the wall thickness of the conical member ranges from about 0.1 mm to about 2 mm, e.g., about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mm. Thicknesses and ranges intermediate to the recited thicknesses and ranges are also contemplated by the present invention.

In another aspect, the present invention provides tissue-engineered pumps which include a housing, a first fluid pumping member comprising an engineered anisotropic muscle tissue and accommodated within the housing, the first fluid pumping member comprising at least one side wall defining a first cavity therein for holding a fluid, a first valve coupled to the first fluid pumping member and configured to enable a fluid flow into the first cavity, a second valve coupled to the first fluid pumping member and configured to enable a fluid flow out of the first cavity, and an energy source for stimulating a collection of cells within the engineered tissue of the first fluid pumping member to cause contraction of a volume of the first cavity.

The energy source may provide electrical or light energy to stimulate the collection of cells.

The tissue-engineered pump may further comprise a second fluid pumping member comprising an engineered anisotropic muscle tissue and accommodated within the housing, the second fluid pumping member comprising at least one side wall defining a second cavity therein for holding a fluid, a third valve coupled to the second fluid pumping member and configured to enable a fluid flow into the second cavity, a fourth valve coupled to the second fluid pumping member and configured to enable a fluid flow out of the second cavity; a fluid inlet mechanism coupled to the first and third valves and configured to introduce fluid flow to the first valve associated with the first fluid pumping member and to the third valve associated with the second fluid pumping member, and a fluid outlet mechanism coupled to the second and fourth valves and configured to receive fluid flow from the second valve associated with the first fluid pumping member and from the fourth valve associated with the second fluid pumping member, wherein the first and second fluid pumping members are coupled in a parallel configuration.

The tissue-engineered pump may further comprise a second fluid pumping member comprising an engineered anisotropic muscle tissue and accommodated within the housing, the second fluid pumping member comprising at least one side wall defining a second cavity therein for holding a fluid, wherein the second fluid pumping member is configured to receive fluid flow from the second valve associated with the first fluid pumping member, and a third valve coupled to the second fluid pumping member and configured to enable a fluid flow out of the second cavity, wherein the first and second fluid pumping members are coupled in a serial configuration.

II. Methods for Generating Engineered Tissue

A. Tissue Scaffolds

Engineered tissues and valves suitable for use in the devices and methods of use thereof of the present invention may be generated by forming a suitable scaffold of micron, submicron or nanometer dimension polymeric fibers configured in a desired shape, and seeding cells onto the polymeric fiber scaffold, and culturing the cells to form a functional tissue.

The micron, submicron or nanometer dimension polymeric fiber may have a diameter of about 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, 10, 20, 30, 40, or about 50 micrometers.

Suitable devices and methods for fabricating the micron, submicron or nanometer dimension polymeric fibers configured in a desired shape are described in U.S. Patent Publication No. 2012/0135448, U.S. patent application Ser. No. 13/988,088, and PCT Application No. PCT/US2012/65646, the contents of each of which are incorporated in their entirety by reference.

In some embodiments, suitable devices generally include a reservoir for holding a polymer, the reservoir including one or more orifices for ejecting the polymer during fiber formation, thereby forming a micron, submicron or nanometer dimension polymeric fiber and a collection device for accepting the formed micron, submicron or nanometer dimension polymeric fiber, wherein at least one of the reservoir and the collection device employs rotational motion during fiber formation, and the device is free of an electrical field, e.g., a high voltage electrical field.

The device may include a rotary motion generator for imparting a rotational motion to the reservoir and, in some exemplary embodiments, to the collection device.

Rotational speeds of the reservoir in exemplary embodiments may range from about 1,000 rpm-50,000 rpm, about 1,000 rpm to about 40,000 rpm, about 1,000 rpm to about 20,000 rpm, about 5,000 rpm-20,000 rpm, about 5,000 rpm to about 15,000 rpm, or about 50,000 rpm to about 400,000 rpm, e.g., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, or about 24,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000 rpm, about 200,000 rpm, 250,000 rpm, 300,000 rpm, 350,000 rpm, or 400,000 rpm. Ranges and values intermediate to the above recited ranges and values are also contemplated to be part of the invention.

In certain embodiments, rotating speeds of about 50,000 rpm-400,000 rpm are intended to be encompassed by the methods of the invention. In one embodiment, devices employing rotational motion may be rotated at a speed greater than about 50,000 rpm, greater than about 55,000 rpm, greater than about 60,000 rpm, greater than about 65,000 rpm, greater than about 70,000 rpm, greater than about 75,000 rpm, greater than about 80,000 rpm, greater than about 85,000 rpm, greater than about 90,000 rpm, greater than about 95,000 rpm, greater than about 100,000 rpm, greater than about 105,000 rpm, greater than about 110,000 rpm, greater than about 115,000 rpm, greater than about 120,000 rpm, greater than about 125,000 rpm, greater than about 130,000 rpm, greater than about 135,000 rpm, greater than about 140,000 rpm, greater than about 145,000 rpm, greater than about 150,000 rpm, greater than about 160,000 rpm, greater than about 165,000 rpm, greater than about 170,000 rpm, greater than about 175,000 rpm, greater than about 180,000 rpm, greater than about 185,000 rpm, greater than about 190,000 rpm, greater than about 195,000 rpm, greater than about 200,000 rpm, greater than about 250,000 rpm, greater than about 300,000 rpm, greater than about 350,000 rpm, or greater than about 400,000 rpm.

Exemplary devices employing rotational motion may be rotated for a time sufficient to form a desired polymeric fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

In some embodiments, the reservoir may not be rotated, but may be pressurized to eject the polymer material from the reservoir through one or more orifices. For example, a mechanical pressurizer may be applied to one or more surfaces of the reservoir to decrease the volume of the reservoir, and thereby eject the material from the reservoir. In another exemplary embodiment, a fluid pressure may be introduced into the reservoir to pressurize the internal volume of the reservoir, and thereby eject the material from the reservoir.

An exemplary reservoir may have a volume ranging from about one nanoliter to about 1 milliliter, about one nanoliter to about 5 milliliters, about 1 nanoliter to about 100 milliliters, or about one microliter to about 100 milliliters, for holding the liquid material. Some exemplary volumes include, but are not limited to, about one nanoliter o about 1 milliliter, about one nanoliter to about 5 milliliters, about 1 nanoliter to about 100 milliliters, one microliter to about 100 microliters, about 1 milliliter to about 20 milliliters, about 20 milliliters to about 40 milliliters, about 40 milliliters to about 60 milliliters, about 60 milliliters to about 80 milliliters, about 80 milliliters to about 100 milliliters, but are not limited to these exemplary ranges. Exemplary volumes intermediate to the recited volumes are also part of the invention. In certain embodiment, the volume of the reservoir is less than about 5, less than about 4, less than about 3, less than about 2, or less than about 1 milliliter. In other embodiments, the physical size of an unfolded polymer and the desired number of polymers that will form a fiber dictate the smallest volume of the reservoir.

The reservoir includes one or more orifices through which one or more jets of the material solution are forced to exit the reservoir by the motion of the reservoir during fiber formation. One or more exemplary orifices may be provided on any suitable side or surface of the reservoir including, but not limited to, a bottom surface of the reservoir that faces the collection device, a side surface of the reservoir, a top surface of the reservoir that faces in the opposite direction to the collection device, etc. Exemplary orifices may have any suitable cross-sectional geometry including, but not limited to, circular, oval, square, rectangular, etc. In an exemplary embodiment, one or more nozzles may be provided associated with an exemplary orifice to provide control over one or more characteristics of the material solution exiting the reservoir through the orifice including, but not limited to, the flow rate, speed, direction, mass, shape and/or pressure of the material solution. The locations, cross-sectional geometries and arrangements of the orifices on the reservoir, and/or the locations, cross-sectional geometries and arrangements of the nozzles on the orifices, may be configured based on the desired characteristics of the resulting fibers and/or based on one or more other factors including, but not limited to, viscosity of the material solution, the rate of solvent evaporation during fiber formation, etc.

Exemplary orifice lengths that may be used in some exemplary embodiments range between about 0.001 m and about 0.1 m, e.g., 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, or 0.1 m. Ranges and values intermediate to the above recited ranges and values are also contemplated to be part of the invention.

Exemplary orifice diameters that may be used in some exemplary embodiments range between about 0.1 μm and about 10 μm, e.g., 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 2, 3, 4, 5, 6, 7, 8, 9, or 10 μm. Ranges and values intermediate to the above recited ranges and values are also contemplated to be part of the invention.

In other embodiments, a suitable device for the formation of a micron, submicron or nanometer dimension polymeric fibers includes a reservoir for holding a polymer, the reservoir including one or more orifices for ejecting the polymer during fiber formation, thereby forming micron, submicron or nanometer dimension polymeric fibers, a collection device, and an air vessel for circulating a vortex of air around the formed fibers to wind the fibers into one or more threads.

In yet other embodiments, a suitable device for the formation of a micron, submicron or nanometer dimension polymeric fiber includes a reservoir for holding a polymer, the reservoir including one or more orifices for ejecting the polymer during fiber formation, thereby forming a micron, submicron or nanometer dimension polymeric fiber, a collection device, one or more mechanical members disposed or formed on or in the vicinity of the reservoir for increasing an air flow or an air turbulence experienced by the polymer ejected from the reservoir, and a collection device for accepting the formed micron, submicron or nanometer dimension polymeric fiber.

In other embodiments of the inventions, suitable devices for fabricating the micron, submicron or nanometer dimension polymeric fibers configured in a desired shape include a platform for supporting a stationary deposit of a polymer, a rotating structure disposed vertically above the platform and spaced from the platform along a vertical axis, and a collection device. The rotating structure includes a central core rotatable about a rotational axis, and one or more blades affixed to the rotating core. The rotating structure is configured and operable so that, upon rotation, the one or more blades contact a surface of the polymer to impart sufficient force in order to decouple a portion of the polymer from contact with the one or more blades of the rotating structure and to fling the portion of the polymer away from the contact with the one or more blades and from the deposit of the polymer, thereby forming a micron, submicron and/or nanometer dimension polymeric fiber.

Sufficient rotational speeds and times for operating the rotating structure to form a fiber may be dependent on the concentration of the material and the desired features of the formed fiber. Exemplary speeds of rotation of the rotating structure may range from about 100 rpm to about 500,000 rpm, although rotational speeds are not limited to this exemplary range. Certain exemplary devices employing rotational motion may be rotated at a speed of about 1,000 rpm-50,000 rpm, about 1,000 rpm to about 40,000 rpm, about 1,000 rpm to about 20,000 rpm, about 5,000 rpm-20,000 rpm, about 5,000 rpm to about 15,000 rpm, or about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, or about 24,000 rpm. Ranges and values intermediate to the above recited ranges and values are also contemplated to be part of the invention. For example, rotating speeds of about 10,000 rpm-15,000 rpm, or 8,000 rpm-12,000 rpm are intended to be encompassed by the methods of the invention. In one embodiment, devices employing rotational motion may be rotated at a speed greater than about 1,000 rpm, greater than about 1,500 rpm, greater than about 2,000 rpm, greater than about 2,500 rpm, greater than about 3,000 rpm, greater than about 3,050 rpm, greater than about 3,100 rpm, greater than about 3,150 rpm, greater than about 3,200 rpm, greater than about 3,250 rpm, greater than about 3,300 rpm, greater than about 3,350 rpm, greater than about 3,400 rpm, greater than about 3,450 rpm, greater than about 3,500 rpm, greater than about 3,550 rpm, greater than about 3,600 rpm, greater than about 3,650 rpm, greater than about 3,700 rpm, greater than about 3,750 rpm, greater than about 3,800 rpm, greater than about 3,850 rpm, greater than about 3,900 rpm, greater than about 3,950 rpm, or greater than about 4,000 rpm. Speeds intermediate to the above recited speeds are also contemplated to be part of the invention.

An exemplary rotating structure may be rotated to impact the liquid material for a time sufficient to form a desired fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

The one or more portions or components of the rotating structure may penetrate into the surface of the liquid material to a desired depth. Exemplary depths of penetration may range from about one nanometer to about one centimeter, but are not limited to this range. Some exemplary penetration depths include, but are not limited to, about one millimeter to about twenty milliliters, about twenty milliliters to about forty milliliters, about forty milliliters to about sixty milliliters, about sixty milliliters to about eighty milliliters, about eighty milliliters to about one hundred milliliters, about one centimeter, and the like. Exemplary penetration depths intermediate to the above-recited exemplary values are also intended to be part of this invention.

The rotating structure may be configured in any suitable manner so that, upon rotation, the rotating structure contacts a surface of the liquid material on platform to impart sufficient force or energy to create a meniscus at the location where the rotating structure contacts the surface. The force or energy imparted by the rotating structure overcomes the surface tension and decouples a portion of the liquid material at the meniscus and flings the portion away from the contact with the rotating structure and from the platform, thereby forming a micron, submicron and/or nanometer dimension fiber. The fiber may be collected on the collection device. In an exemplary embodiment, the direction in which the liquid material is flung may be substantially the same as the tangential direction of motion of the component of the rotating structure that contacts the liquid material. In an exemplary embodiment, the rotating structure may impart a force to the liquid material in a substantially parallel direction to the top surface of the liquid material.

In one embodiment, the rotating structure may have a central core rotatable in a clockwise and/or counter-clockwise manner about a central axis of rotation R. In an exemplary embodiment, the rotational axis R may be offset at substantially 90 degrees from the vertical axis V. The core may have a substantially cylindrical shape with a substantially circular cross-section having a center aligned along the axis of rotation R. The rotating structure may also include one or more protrusions, e.g., in the form of blades, brushes, bristles, etc., affixed to the outer surface of the rotating core so that part of the protrusions penetrate into the surface of the liquid material. Exemplary rotating structures may include any suitable number of protrusions affixed to the core including, but not limited to, one protrusion to 500 protrusions. Some exemplary numbers of protrusions include, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 50 to about 100, about 100 to about 200, about 200 to about 300, about 300 to about 400, about 400 to about 500, and the like. Exemplary numbers of protrusions intermediate to the recited exemplary numbers are also part of the invention. The protrusions may be configured on the core in any suitable arrangement including, but not limited to, a regular multi-row or multi-column arrangement, an array pattern, a circular arrangement, a random arrangement, and the like.

Each protrusion may have any suitable shape including, but not limited to, a substantially rectangular shaped protrusion, a saw shaped protrusion wherein the base of the protrusion at the core is wider than the tip farthest from the core, a cylindrical shaped protrusion, and the like. At high rotational speeds and/or in instances where broken protrusions would compromise the purity of the fibers, the saw shape may provide enhanced structural integrity to the protrusions and may prevent break-off of the protrusions during rotation.

In some exemplary embodiments, one or more aspects of the protrusions on the rotating structure may be varied to control the adherence of the liquid material to the protrusions when the liquid material comes into contact with the protrusions, thereby facilitating fiber formation. Exemplary aspects that may be control or configured include, but are not limited to, the surface chemistry of the protrusions, the surface topography of the protrusions (e.g., a rougher texture), a geometry of the protrusions (e.g., a cross-sectional shape of the protrusions), and the like. In addition, configuring these aspects of the protrusions may allow controlling the geometry of the fibers that are formed, fiber width, surface features on the fibers, and the like.

Exemplary protrusions may be formed of any suitable material including, but not limited to, titanium, stainless steel (e.g., 300 and 400 alloys), aluminum (e.g., 6061, 7075), polystyrene, polypropylene, (e.g., UHMW, HDPE, LDPE), ABS, acetal (copolymer and homopolymer), nylon, polycarbonate, polyether ether ketone, polymethyl methacrylate, polysulfone, polytetrafluoroethylene, polyvinylchloride, and the like.

In some embodiments, the collection device may be a mandrel configured in a desired shape and positioned in the path of the polymer ejected from the one or more orifices or in the path of the fibers flung from the rotating structure.

Any suitable size or geometrically shaped reservoir or collector may be used in the devices of the invention. For example, the reservoir may be tubular, conical, semilunar, bicuspid, round, rectangular, or oval. The collector (and/or the mandrel) may be round, oval, rectangular, or a half-heart shape. The collector may also be shaped in the form of any living organ, such as a heart, kidney, liver lobe(s), bladder, uterus, intestine, skeletal muscle, or lung shape, or portion thereof. The collector may further be shaped as any hollow cavity, organ or tissue, such as a circular muscle structure, e.g., a valve, sphincter or iris. In one embodiment, the mandrel is in a tubular shape. In another embodiment, the mandrel is in a conical shape (see, e.g., FIG. 20). In other embodiments, the mandrel is configured in the shape of a tricuspid or bicuspid valve.

In exemplary embodiments, the collection device, e.g., mandrel, may be disposed at a distance of about 1 inch to about 15 inches from the reservoir from which the polymer is ejected, but is not limited to this exemplary range. Certain exemplary distances may include, but are not limited to 1, 2, 3, 4, 5, 6, 7, 8, 9, 10, 11, 12, 13, 14, 15, and all intermediate numbers, and the like.

This distance is carefully configured to avoid formation of fibrous beads (which may occur if the collection device is too close to the reservoir) and to achieve sufficient fibrous mass (which may not occur if the collection device is too far from the reservoir).

An exemplary collection device, e.g., mandrel, may be coupled to one or more motion generators for imparting rotational and/or linear motion to the collection device. An exemplary collection device may be rotated about at speeds ranging from about 1,000 rpm to about 80,000 rpm, but is not limited to this exemplary range. Rotational speeds of the collection device in exemplary embodiments may range from about 1,000 rpm-50,000 rpm, about 1,000 rpm to about 40,000 rpm, about 1,000 rpm to about 20,000 rpm, about 5,000 rpm-20,000 rpm, about 5,000 rpm to about 15,000 rpm, or about 50,000 rpm to about 400,000 rpm, e.g., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, or about 24,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000 rpm, about 200,000 rpm, 250,000, 300,000 rpm, 350,000 rpm, or 400,000 rpm. Ranges and values intermediate to the above recited ranges and values are also contemplated to be part of the invention.

Increased rotational speeds may enable greater fiber alignment. An exemplary collection device, e.g., mandrel, may be moved vertically up and down (or moved up and down at an angle to the vertical axis) at linear speeds ranging from about 1 mm/s to about 300 mm/s, e.g., about 1, 2, 3, 4, 5, 6, 7, 8, 9, 10, 20, 25, 30, 35, 40 4, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300 mm/s. Ranges and speeds intermediate to he recited ranges and speeds are also contemplated by the present invention.

An exemplary tissue-engineered structure (e.g., a tubular member, a valve, a conical member) may be formed using a polymeric scaffold formed by any suitable number of overlapping layers of polymeric fibers. Exemplary numbers of layers of polymeric fibers of about 5 to about 100,000 may be disposed on the mandrel at a time to create a polymeric scaffold.

An exemplary polymeric scaffold may have any desired length and thickness. Exemplary thicknesses may range from about 50 microns to about 2 mm, but are not limited to this exemplary range. The thickness is carefully configured to be sufficient to provide mechanical and tensile strength to the scaffold and so that the scaffold allows diffusion of cells and nutrition to the inner layers of the polymeric fibers.

In order to fabricate the scaffold in a desired shape, the mandrel is positioned in the path of the fibers ejected from the reservoir or in the path of the fibers flung from the rotating structure and rotated, angled and/or vertically maneuvered such that the fibers are accepted on the mandrel at a desired thickness and pattern.

In one embodiment, in order to fabricate a pump, the apical portion of a conical mandrel is positioned in the path of the ejected fibers and rotated such that the fibers wrap circumferentially around the apex. In order to provide the fibers on the side walls of the conical mandrel, in one embodiment, the mandrel is held in one position (i.e., is not rotated) and moved vertically. Once the fibers have been configured on one side wall at a desired thickness, the mandrel is rotated (e.g., 30 degrees) to provide the fibers on another side wall, moved vertically, and so forth, until a suitable conical shape is prepared. In another embodiment, the mandrel may be continually rotated to facilitate collection of the fibers that are wrapped around the mandrel.

Figure 23:
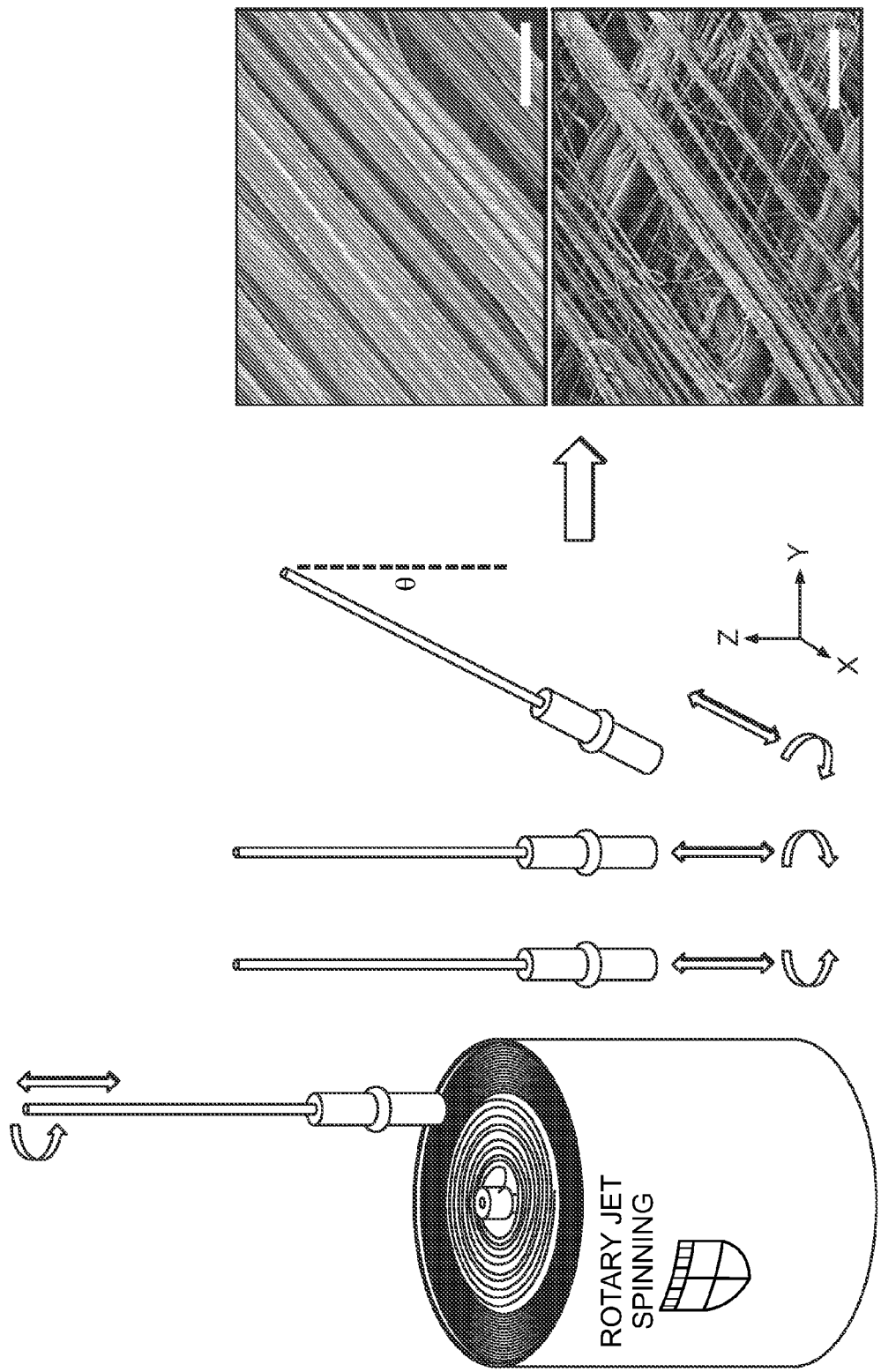
FIG. 23 depicts exemplary methods using a rotating mandrel to achieve different alignments or weaves of polymeric fibers to fabricate cell scaffolds for use in fabricating a tissue-engineered valve of the invention.

FIG. 23 provides exemplary methods for fabricating a scaffold of polymeric fibers for fabrication of a tissue engineered valve. Fibers ejected from a rotating reservoir of flung from a rotating structure are wrapped via mandrel rotation around the Z axis; by slowly moving the mandrel along the Z axis while rotating, complete aligned coverage of the mandrel can be achieved (top SEM image, scale bar 10 μm). By increasing speed of Z axis translation or rotating the mandrel a certain θ with respect to the X or Y axis, cross or "x" shaped weaves can be produced (bottom SEM image, scale bar 50 μm). The mandrel may be moved manually or mechanically.

In one embodiment, the devices of the invention further comprise a component suitable for continuously feeding the polymer into the rotating reservoir (or a platform), such as a spout or syringe pump.

An exemplary method to fabricate the micron, submicron or nanometer dimension polymeric fibers configured in a desired shape (e.g., a tubular shape, a valve shape, a conical shape) may include imparting rotational motion to a reservoir holding a polymer, the rotational motion causing the polymer to be ejected from one or more orifices in the reservoir and collecting the formed fibers on a mandrel having the desired shape, to form the micron, submicron or nanometer dimension polymeric fibers in the desired shape.

In one embodiment, the methods include feeding a polymer into a rotating reservoir of a device of the invention and providing motion at a speed and for a time sufficient to form a micron, submicron or nanometer dimension polymeric fiber, and collecting the formed fibers on a mandrel having the desired shape, to form the micron, submicron or nanometer dimension polymeric fibers in the desired shape.

In another embodiment, the methods include providing a polymer solution and imparting a sufficient amount of shear stress to the polymer solution for a time sufficient to form a micron, submicron or nanometer dimension polymeric fiber, and collecting the formed fibers on a mandrel having the desired shape, to form the micron, submicron or nanometer dimension polymeric fibers in the desired shape. In one embodiment, a sufficient amount of shear stress in about 3,000 Pascals.

In another embodiment, the methods include feeding a polymer solution into a rotating reservoir of a device of the invention and providing an amount of shear stress to the rotating polymer solution for a time sufficient to form a micron, submicron or nanometer dimension polymeric fiber, and collecting the formed fibers on a mandrel having the desired shape, to form the micron, submicron or nanometer dimension polymeric fibers in the desired shape.

In one embodiment, the scaffold is generated by forming the micron, submicron or nanometer dimension polymeric fibers in a tubular shape by imparting rotational motion to a reservoir holding a polymer, the rotational motion causing the polymer to be ejected from one or more orifices in the reservoir to form the micron, submicron or nanometer dimension polymeric fibers, and collecting the formed fibers on a mandrel having a tubular shape, to form the micron, submicron or nanometer dimension polymeric fibers in the desired shape.

In another embodiment, the scaffold is generated by forming the micron, submicron or nanometer dimension polymeric fibers in a conical shape by imparting rotational motion to a reservoir holding a polymer, the rotational motion causing the polymer to be ejected from one or more orifices in the reservoir to form the micron, submicron or nanometer dimension polymeric fibers, and collecting the formed fibers on a mandrel having a conical shape, to form the micron, submicron or nanometer dimension polymeric fibers in the desired shape.

In another embodiment, the scaffold is generated by forming the micron, submicron or nanometer dimension polymeric fibers in a valve shape (e.g., tricuspid or mitral valve shape) by imparting rotational motion to a reservoir holding a polymer, the rotational motion causing the polymer to be ejected from one or more orifices in the reservoir to form the micron, submicron or nanometer dimension polymeric fibers, and collecting the formed fibers on a mandrel having a valve shape, to form the micron, submicron or nanometer dimension polymeric fibers in the desired shape.

Exemplary materials used to make fibers include synthetic polymers, such as polyethylene, polypropylene, poly(lactic acid), etc. In some exemplary embodiments, the synthetic polymers may be specifically synthesized to possess domains along the backbone that may be activated for specific purposes including, but not limited to, specific binding, folding, unfolding, etc. Exemplary materials may also include biogenic polymers, e.g., natural polymers, such as chitosan, alginate, gelatin, etc. Exemplary biogenic polymers may also include protein materials, such as collagen, fibronectin, laminin, etc. Exemplary materials may also include other suitable materials, e.g., metallic or ceramic materials.

Exemplary polymers for use in the devices and methods of the invention may be biocompatible or nonbiocompatible, synthetic or natural, such as, for example, synthetic or natural polymers having shear induced unfolding. Exemplary polymers include, for example, poly(urethanes), poly (siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, polyorthoesters, polyesters, polyamides, polyolefins, polycarbonates, polyaramides, polyimides, polycaprolactone (PCL), and copolymers and derivatives thereof.

Exemplary polymers for use in the devices and methods of the invention may also be naturally occurring polymers e.g., biogenic polymers, e.g., proteins, polysaccharides, lipids, nucleic acids or combinations thereof.

Exemplary biogenic polymers, e.g., polymers made in a living organism, e.g., fibrous proteins, for use in the devices and methods of exemplary embodiments include, but are not limited to, silk (e.g., fibroin, sericin, etc.), keratins (e.g., alpha-keratin which is the main protein component of hair, horns and nails, beta-keratin which is the main protein component of scales and claws, etc.), elastins (e.g., tropoelastin, etc.), fibrillin (e.g., fibrillin-1 which is the main component of microfibrils, fibrillin-2 which is a component in elastogenesis, fibrillin-3 which is found in the brain, fibrillin-4 which is a component in elastogenesis, etc.), fibrinogen/fibrins/thrombin (e.g., fibrinogen which is converted to fibrin by thrombin during wound healing), fibronectin, laminin, collagens (e.g., collagen I which is found in skin, tendons and bones, collagen II which is found in cartilage, collagen III which is found in connective tissue, collagen IV which is found in extracellular matrix protein, collagen V which is found in hair, etc.), vimentin, neurofilaments (e.g., light chain neurofilaments NF-L, medium chain neurofilaments NF-M, heavy chain neurofilaments NF-H, etc.), amyloids (e.g., alpha-amyloid, beta-amyloid, etc.), actin, myosins (e.g., myosin I-XVII, etc.), titin which is the largest known protein (also known as connectin), gelatin, etc.

Exemplary biogenic polymers, e.g., fibrous polysaccharides, for use in the devices and methods of exemplary embodiments include, but are not limited to, chitin which is a major component of arthropod exoskeletons, hyaluronic acid which is found in extracellular space and cartilage (e.g., D-glucuronic acid which is a component of hyaluronic acid, D-N-acetylglucosamine which is a component of hyaluronic acid, etc.), etc.

Exemplary biogenic polymers, e.g., glycosaminoglycans (GAGs) (carbohydrate polymers found in the body), for use in the devices and methods of exemplary embodiments include, but are not limited to, heparan sulfate founding extracelluar matrix, chondroitin sulfate which contributes to tendon and ligament strength, keratin sulfate which is found in extracellular matrix, etc.

In one embodiment the polymers for use in the devices and methods of the invention may be mixtures of two or more polymers and/or two or more copolymers. In one embodiment the polymers for use in the devices and methods of the invention may be a mixture of one or more polymers and or more copolymers. In another embodiment, the polymers for use in the devices and methods of the invention may be a mixture of one or more synthetic polymers and one or more naturally occurring polymers. For example, in one embodiment, the polymers are a mixture of collagen and polycarpolactone.

In one embodiment, the polymer is fed into the reservoir as a polymer solution, i.e., a polymer dissolved in an appropriate solution. In this embodiment, the methods may further comprise dissolving the polymer in a solvent prior to feeding the polymer into the reservoir. In other embodiments, the polymer is fed into the reservoir as a polymer melt. In such embodiment, the reservoir is heated at a temperature suitable for melting the polymer, e.g., is heated at a temperature of about 100° C. to about 300° C., 100-200° C., about 150-300° C., about 150-250° C., or about 150-200° C., or about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300° C.

In some embodiments of the invention, engineered tissues suitable for use in the devices and methods of use thereof of the present invention may be generated using a flexible polymer layer, e.g., PDMS, comprising a spatially micro-patterned engineered surface chemistry (e.g., as described in the appended Examples and in, for example, U.S. Pat. No. 8,492,150, U.S. Patent Application Publication Nos. 2012/0142556 and 2013/0046134, and U.S. patent application Ser. No. 13/808,411, the entire contents of each of which are incorporated herein by reference), seeding cells on the scaffold, culturing the cells to form a functional tissue, and cutting a desired shape into the tissue formed.

Briefly, a rigid base material is coated with a sacrificial polymer layer; a flexible polymer layer is temporarily bonded to the rigid base material via the sacrificial polymer layer, and an engineered surface chemistry is provided on the flexible polymer layer to enhance or inhibit cell and/or protein adhesion. Cells are seeded onto the flexible polymer layer, and cultured to form a tissue comprising, for example, patterned anisotropic myocardium. A desired shape of the to flexible polymer layer can then be cut (e.g., using a scalpel, razor blade, punch, die or laser) to configure the scaffold in a desired shape; and the flexible film, including the polymer layer and tissue, can be peeled off with a pair of tweezers as the sacrificial polymer layer dissolves to release the flexible polymer layer, to produce a free-standing film.

The base layer may be formed of a rigid or semi-rigid material, such as a plastic, metal, ceramic, or a combination thereof. The base layer is ideally biologically inert, has low friction with the tissues and does not interact (e.g., chemically) with the tissues. Examples of materials that can be used to form the base layer include polystyrene, polycarbonate, polytetrafluoroethylene (PTFE), polyethylene terephthalate, quartz, silicon, and glass.

The sacrificial polymer layer is deposited on the base layer, i.e., is placed or applied onto the base layer. Depositing may include, but is not limited to, spraying, dip casting, and spin-coating. The sacrificial polymer layer may be deposited on substantially the entire surface or only a portion of the surface of the base layer.

In one embodiment, spin-coating is used to deposit the sacrificial polymer layer on the base material. "Spin-coating" is a process wherein the base layer is mounted to a chuck under vacuum and is rotated to spin the base layer about its axis of symmetry while a liquid or semi-liquid substance, e.g. a polymer, is dripped onto the base layer. Centrifugal force generated by the spin causes the liquid or semi-liquid substance to spread substantially evenly across the surface of the base layer.

In one embodiment, the sacrificial polymer is a thermally sensitive polymer that can be melted or dissolved to release the flexible polymer layer. For example, linear non-cross-linked poly(N-Isopropylacrylamide) (PIPAAM), which is a solid when dehydrated or at about 37° C., wherein the polymer is hydrated, but relatively hydrophobic. When the temperature of the polymer is dropped to about 35° C. or less, wherein the polymer is hydrated, but relatively hydrophilic, the polymer liquefies, thereby releasing the patterned flexible polymer layer (Feinberg et al., *Science* 317:1366-1370, 2007).

In another embodiment, the sacrificial polymer becomes hydrophilic when the temperature is lowered, thereby releasing hydrophobic coatings. For example, the sacrificial polymer can be hydrated, cross-linked PIPAAM, which is hydrophobic at about 37° C. and hydrophilic at about 35° C. or less (e.g., about 35° C. to about 32° C.). In yet another embodiment, the sacrificial polymer is an electrically actuated polymer that becomes hydrophilic upon application of an electric potential and releases a hydrophobic structure coated thereon. Examples of such a polymer include poly (pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s. In another embodiment, the sacrificial polymer is a degradable biopolymer that can be dissolved to release a structure coated thereon. For example, the polymer (e.g., polylactic acid, polyglycolic acid, poly(lactic-glycolic) acid copolymers, or nylons) undergoes time-dependent degradation by hydrolysis or by enzymatic action (e.g., fibrin degradation by plasmin, collagen degradation by collagenase, fibronectin degradation by matrix metalloproteinase).

In one embodiment, the sacrificial polymer is an ultra-hydrophobic polymer with a surface energy lower than the flexible polymer layer adhered to it. In this case, mild mechanical agitation will "pop" the patterned flexible polymer layer off of sacrificial polymer layer. Examples of such a polymer include but are not limited to alkylsilanes (octadecyltrichlorosilane and isobutyltrimethoxysilane), fluoroalkylsilanes (tridecafluorotetrahydrooctyltrichlorosilane, trifluoropropyltrichlorosilane and heptadecafluorotetrahydrodecyltrichlorosilane), silicones (methylhydrosiloxane-dimethylsiloxane copolymer, hydride terminated polydimethylsiloxane, trimethylsiloxy terminated polydimethylsiloxane and diacetoxymethyl terminated polydimethylsiloxane), fluorinated polymers (polytetrafluoroethylene, perfluoroalkoxy and fluorinated ethylene propylene). For example, the base material can be a glass cover slip coated with a sacrificial polymer layer of PIPAAM.

Examples of the elastomers that can be used to form the flexible polymer layer include polydimethylsiloxane (PDMS) and polyurethane. In one embodiment, the PDMS, once cured is opaque (e.g., light-absorbing). In other embodiments, thermoplastic or thermosetting polymers are used to form the flexible polymer layer. Alternative non-degradable polymers include polyurethanes, silicone-urethane copolymers, carbonate-urethane copolymers, polyisoprene, polybutadiene, copolymer of polystyrene and polybutadiene, chloroprene rubber, Polyacrylic rubber (ACM, ABR), Fluorosilicone Rubber (FVMQ), Fluoroelastomers, Perfluoroelastomers, Tetrafluoro ethylene/propylene rubbers (FEPM) and Ethylene vinyl acetate (EVA).

In still other embodiments, biopolymers, such as collagens, elastins, polysaccharides, and other extracellular matrix proteins, are used. Suitable biodegradable elastomers include hydrogels, e.g., alginate and gelatin, elastin-like peptides, polyhydroxyalkanoates and poly(glycerol-sebecate). Suitable non-elastomer, biodegradable polymers include polylactic acid, polyglycolic acid, poly lactic glycolic acid copolymers.

In one embodiment, the flexible polymer layer comprises polydimethylsiloxane (PDMS). The thickness of the PDMS layer can be controlled by the viscosity of the prepolymer and by the spin-coating speed, ranging from 14 to 60 μm thick after cure. The viscosity of the prepolymer increases as the cross-link density increases. This change in viscosity between mixing and gelation can be utilized to spin-coat different thicknesses of flexible polymer layers. Alternatively the spin-coating speed can be increased to create thinner polymer layers. After spin-coating, the resulting polymer scaffolds are either fully cured at room temperature (generally, about 22° C.) or at 65° C.

In some embodiments, once formed, the scaffolds, e.g., the plurality of micron, submicron or nanometer dimension polymeric fibers scaffolds and the scaffolds comprising a flexible polymer layer, are seeded with cells and cultured in an incubator under physiologic conditions (e.g., at 37° C.) until the cells form an engineered muscle tissue.

Any appropriate cell culture method may be used. The seeding density of the cells will vary depending on the cell size and cell type, but can easily be determined by methods known in the art. In one embodiment, cardiac myocytes are seeded at a density of between about $1\times10^5$ to about $6\times10^5$ cells/cm$^2$, or at a density of about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $1.5\times10^5$, about $2\times10^5$, about $2.5\times10^5$, about $3\times10^5$, about $3.5\times10^5$, about $4\times10^5$, about $4.5\times10^5$, about $5\times10^5$, about $5.5\times10^5$, about $6\times10^5$, about $6.5\times10^5$, about $7\times10^5$, about $7.5\times10^5$, about $8\times10^5$, about $8.5\times10^5$, about $9\times10^5$, about $9.5\times10^5$, about $1\times10^6$, about $1.5\times10^6$, about $2\times10^6$, about $2.5\times10^6$, about $3\times10^6$, about $3.5\times10^6$, about $4\times10^6$, about $4.5\times10^6$, about $5\times10^6$, about $5.5\times10^6$, about $6\times10^6$, about $6.5\times10^6$, about $7\times10^6$, about $7.5\times10^6$, about $8\times10^6$, about $8.5\times10^6$, about $9\times10^6$, or about $9.5\times10^6$. Values and ranges intermediate to the above-recited values and ranges are also contemplated by the present invention.

In some embodiments, the scaffold is contacted with living cells during the fabrication process such that scaffolds populated with cells or fibers surrounded (partially or totally) with cells are produced. The scaffolds may also be contacted with additional agents, such as proteins, nucleotides, lipids, drugs, pharmaceutically active agents, biocidal and antimicrobial agents during the fabrication process such that functional micron, submicron or nanometer dimension polymeric fibers are produced which contain these agents. For example, fibers comprising living cells may be fabricated by providing a polymer and living cells in a solution of cell media at a concentration that maintains cell viability.

B. Cells Suitable for Use in the Claimed Devices

Suitable cells for use in the claimed devices may be normal cells, abnormal cells (e.g., those derived from a diseased tissue, or those that are physically or genetically altered to achieve an abnormal or pathological phenotype or function), normal or diseased muscle cells derived from embryonic stem cells or induced pluripotent stem cells. Preferably, the cells for the fabrication of a tissue-engineered pump are muscle cells, e.g., cardiomyocytes. In other embodiments for the fabrication of a tissue-engineered valve, the cells are umbilical endothelial cells, vascular endothelial cells, mesenchymal stem cells, primary valve harvest endothelial/interstitial cells.

Cells for seeding can be cultured in vitro, derived from a natural source, genetically engineered, or produced by any other means. Any natural source of prokaryotic or eukaryotic cells may be used. Embodiments in which the claimed pumps and/or valves are implanted in an organism can use cells from the recipient, cells from a conspecific donor or a donor from a different species, or bacteria or microbial cells.

In some embodiments of the invention, an engineered tissue, or portion thereof, may comprise a population of pacing, e.g., cardiac, e.g., pacemaker cells, expressing a photosensitive membrane transport mechanism, such as a light-gated ion channel or a light-driven ion pump (see, e.g., FIGS. 23 and 24). As used herein, the term "photosensitive membrane transport mechanism" refers to an ion channel or ion transporter protein that is sensitive to a specific wavelength(s) of light and can be used to generate or silence action potentials in cells expressing these proteins. As a result, the engineered tissue, or portions thereof, become photosensitive and can be regulated by light stimulation. Through the use of specific ion channel or ion transporter proteins, action potentials may be stimulated (to restore regular beating) or silenced (to inhibit defibrillation).

The photosensitive membrane transport mechanism is responsive to photostimulation, e.g., responsive to light of a particular wavelength(s). Thus, photostimulation of the membrane transport mechanism affects the membrane potential of the pacing cells, e.g., pacemaker cells, e.g., the engineered tissue may be selectively and controllably depolarized or hyperpolarized in response to photostimulation.

The engineered tissues (or portions thereof) comprising a photosensitive cardiac rhythm modulation mechanism may comprise any suitable electrically excitable cell including, but not limited to, cells derived from a sinoatrial or an atrioventricular node, cells derived from the cardiac conduction system, and cardiac progenitor cells for the nodes and conduction system. Any genetically engineered cells that possess the required electrical excitation or pacemaker properties are also appropriate. These include, but are not limited to, embryonic stem cells, induced pluripotent stem (iPS) cells, adult mesenchymal stem cells, adult cardiac resident stem cells, and other adult stem cells (e.g., hematopoietic cells, fat cells).

In one embodiment, suitable cells are pacing cells from a stable cell line, e.g., an iPS cell line, generated by transfecting pacing cells with a photosensitive membrane transport mechanism. The cells may advantageously be suitable for excitation-contraction (EC) coupling relative to endogenous cardiac muscle tissue.

Heterologously expressed microbial opsins can be used to control membrane potential. These include channelrhodopsins, halorhodopsins, bacteriorhodopsins (reviewed in J. P. Klare, et al., *Result. Probl. Cell. Differ.* 45: 73-122, 2008), step-function opsins (Diester, et al. (2011) *Nature Neuroscience* 14:387; Yizhar et al. (2011) *Nature* 477:171-178) and engineered chimeric opsin variants (C1V1) composed of ChR1 and VChR1 fragments, that implement fast and potent optical excitation at red-shifted wavelengths (about 450-600 nm) (see, e.g., Yizhar, et al. (2011) *Nature* 477:171-178; Mattis et al. (2011) *Nature Methods* 9:159-172). For example, channel rhodopsin-1 (ChR1), a light-gated proton channel, and channelrhodopsin-2 (ChR2), a light-activated cation channel naturally expressed by *Chlamydomonas reinhardtii*, may be used.

The N-terminal 315 amino acids of ChR2 compose an ion channel with light-gated conductance. ChR2 has been expressed stably in mammalian neurons, where it is capable of driving neuronal depolarization. Upon exposure to blue light, ChR2 expressed in genetically engineered neurons rapidly stimulates neuronal spiking and creates action potentials. (ES Boyden, et al., *Nat. Neurosci.* 8: 1263-1268, 2005). VChR1 from Volvox carteri, exhibits an action spectrum with two maxima, 531 nm and 589 nm, which are red-shifted with respect to the absorption maximum of ChR2 (approximately 470 nm) (F. Zhang, et al., *Nat. Neurosci.* 11: 631-633, 2008). Halorhodopsins include NpHR, which is naturally expressed by Natronomonas pharaonic. NpHR is a high-speed hyperpolarizing chloride ion pump responsive to yellow light. When expressed in genetically engineered neurons, NpHR inhibits action potentials in response to yellow light. (F. Zhang, et al., *Nature* 446: 633-639, 2007). Bacteriorhodopsin is stimulated by green light, wavelength of 500-650 nm, with absorption maximum at 568 nm. Step-function opsins, described in, for example, PCT publication WO 2012/061744, the entire contents of which is incorporated herein by reference, exhibit rapid step-like activation in response to a single pulse of light having a first wavelength (blue light, about 470 nm) and deactivation in response to a pulse of light having a second wavelength (red light, about 540-590 nm).

When expressed in cells, bacterial opsins such as ChR2, VChR1 and NpHR provide complementary tools for regulating the frequency and rhythm of heartbeat. For example, in one embodiment of the invention, cells are genetically engineered to express ChR2 to stimulate action potentials in response to blue light. These cells function as a pacemaker. In another embodiment, cells are genetically engineered to express NpHR, to inhibit action potentials and propagation of action potentials. These cells function as a defibrillator.

The gene sequences for ChR1, VChR1, ChR2, NpHR, stabilized step-function opsins (SSFO) and CIV1 opsins are known in the art and may be found in, for example, GenBank Reference Nos. GI:159481916, GI:159487988, GI:159481998, GI:167650745, GI:167650741, GI:342356708 and 342356710 (the contents of each of which are incorporated herein in their entirety), and heterologous expression has been reported for each of these opsin genes (ES Boyden, et al., *Nat. Neurosci.* 8: 1263-1268, 2005; F. Zhang, et al., *Nat. Neurosci.* 11: 631-633, 2008; F. Zhang, et al., *Nature* 446: 633-639, 2007).

In one embodiment, the cells for use in the engineered muscle tissues (or portions thereof) are transfected with the photosensitive membrane transport mechanism, e.g., an opsin gene, prior to formation of engineered muscle tissues. In another embodiment, the cells for use in an engineered muscle tissue are transfected with the photosensitive membrane transport mechanism, e.g., an opsin gene, after growth to form the engineered muscle tissue.

In other embodiments, cells comprising the photosensitive membrane transport mechanism configured in a desired shape to form a SA and/or AV node are grafted onto an engineered muscle tissue, e.g., an engineered muscle tissue pump. In these embodiments of the invention, the cells configured in a desired shape to form a SA and/or AV node are constructed in an appropriate size, shape and architecture so that they will functionally (e.g., mechanically and electrically connect) with the engineered muscle tissue. Functional attachment can be demonstrated by the formation of adherens and gap junctions between the cells of the engineered SA and/or AV node and the cells of pump.

Tissue comprising a photosensitive membrane transport mechanism can also be specifically configured to generate an electrical impulse that induces an action potential through the attached cardiac tissue. Optical mapping can be used to assess whether the photosensitive cardiac rhythm modulation tissue structure is functionally attached to the epicardium or endocardium.

In one embodiment, cardiac myocytes are co-cultured with neurons to prepare innervated engineered tissue described in U.S. application Ser. No. 13/580,191, filed Aug. 21, 2012, the entire contents of which are incorporated herein by reference.

In another embodiment, cardiac myocytes are co-cultured with photosensitive tissues and/or cells, such as those derived from retina or the chromatophores of invertebrates and lower vertebrates, e.g., cephalopods, amphibians, fish, reptiles, and crustaceans.

Cells and tissue comprising a photosensitive membrane transport mechanism can be actuated by photostimulation from an integrated fiber optic microelectromechanical systems (MEMS) device. The sensor analyzes rate and rhythm of muscle cell contractions in the engineered muscle tissue and signals the generator when a correction in rate or rhythm is necessary. The generator provides power for the sensor and the light source. Only very small amounts of light are required, reducing power consumption and allowing the use of very small generators, e.g., batteries. The light source produces light of a specific wavelength(s) for selective stimulation or silencing of action potentials within the biological cardiac rhythm modulation structure. For example, blue light wavelengths (approximately 445-490 nm, preferably 470-475 nm) can be used to activate ChR2 and stimulate action potentials and yellow light wavelengths (approximately 573-613 nm, preferably 575 to 625 nm) can be used to activate NpHR and silence action potentials. The light source can comprise high intensity light-emitting diodes (LED), a diode laser, or other light source coupled to an optical fiber. In exemplary embodiments, a low-power or ultra-low-power sensor array may be adapted to function as a light source, e.g., in conjunction with a fiber optic delivery scheme. In further exemplary embodiments, a chemiluminescent light source such as bioengineered light source may be utilized. Thus, e.g., photocytes may be integrated with optical relay and/or optical switching element to provide photostimulation.

The light source may be tethered to an external power source or powered by an implanted battery pack. Commercially available ultra-compact fiber-coupled diode laser modules, such as the FIBERTEC$^{II}$™ (Blue Sky Research, Milpitas, Calif.) modules, are suitable light sources. The light source may advantageously be controlled using a microelectromechanical system (MEMS) system and associated fiber optics. MEMS systems may include, e.g., MEMS-driven optical switches or digital micromirror devices (DMD) (for digital light processing). In exemplary embodiments, the light source may provide programmable high spatial and temporal resolution multipoint photostimulation of the photosensitive tissue, e.g., using a guided laser. Spatial resolution may be, e.g., on the micron level and temporal resolution may be e.g., on the millisecond level. Thus, a guided laser could readily focus on and independently stimulate, e.g., either of two neighboring muscular actuators (gaps in tissue continuity may be used to establish discrete regions for photostimulation). In exemplary embodiments, an external light source may be used to provide photostimulation. Thus, in on embodiment, the light source may comprise a tissue-penetrating infrared light for transthoracic photostimulation.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness."Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. WO 2010/042856, entitled "Tissue Engineered Myocardium and Methods of Productions and Uses Thereof", filed Oct. 9, 2009, the entire contents of which are incorporated herein by reference.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

Any appropriate method known in the art may be used to transfect cells with a photosensitive membrane transport mechanism. Standard methods include transfection with viral or nonviral vector systems, electroporation, and microinjection. For example, in one embodiment, substrate-mediated transfection as described in, for example, Ziauddin and Sabatini (*Nature* (2001) 3:411), Houchin-Ray, et al. (*Mol Thera* (2007) 15(4):705-12), Jang, et al. (*J Biomed Mater Res A*. (200) 77(1):50-8, and WO/2006/031800, the entire contents of which are incorporated herein by reference, may be used to transfect cells. In another embodiment, patterned surface-mediated transfection as described in, for example, Hu, et al. (*Gene Ther*. (2007)14(11):891-901), Lei, et al. (*Biomaterials*. (2009) 30(22):3790-9), and Stachelek, et al. (*Gene Ther*. (2004) 11(1):15-24), the entire contents of which are incorporated herein by reference, may be used to transfect cells.

Viral and nonviral vector systems can be designed using known methods to combine the elements necessary for directing transcription, translation, or both, of the nucleic acid encoding a photosensitive membrane transport mechanism in a cell. Methods known in the art can be used to construct expression constructs having the protein coding sequence operably linked with appropriate transcriptional/translational control signals. These methods are fully described in a number of laboratory manuals including *Current Protocols in Molecular Biology*, Online ISSN: 1934-3647, John Wiley & Sons, NY, 2010; *Gene Transfer: Delivery and Expression of DNA And RNA, A Laboratory Manual*, Theodore Friedmann and John Rossi, Cold Spring Harbor Laboratory Press, 2006; *Molecular Cloning: A Laboratory Manual*, 3rd Ed., J. Sambrook and D. Russell, Cold Spring Harbor Laboratory Press, 2001; Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401(1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems particularly suitable for use in the in vivo transfection of cardiac muscle cells with a photosensitive membrane transport system, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used for the in vivo transfection of cardiac muscle cells with a photosensitive membrane transport system. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283). An AAV2/5 or AAV2/8 vector, as described in, for example, U.S. Pat. No. 7,056,502, (the entire contents of which are incorporated herein by reference) may also be used.

For in situ transfection of cardiac cells, a vector system targeting cardiac cells, such as an adeno-associated viral (AAV) system as described in, for example, U.S. Patent Applications 20090209631 and 20080263691, or a non-viral vector system as described in, for example, U.S. Pat. No. 6,436,907, U.S. Patent Application 20060199778, or U.S. Pat. No. 6,379,966 may also be used. The entire contents of all of the patents and application are incorporated herein by reference.

In another embodiment, cells are transfected with a lentivirus as described in T. Sakoda, et al., *J Mol Cell Cardiol* 31: 2037-47, 1999, and in *Lentivirus Gene Engineering Protocols 2nd Ed.*, Maurizio Federico, *Methods in Molecular Biology* Series, Humana Press, 2009.

The vector may include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan. In one embodiment, a suitable promoter is a cardiac-specific promoter, such as, but not limited to, the myosin light chain-2 promoter (Franz et al., 1994; Kelly et al., 1995), the alpha actin promoter (Moss et al., 1996), the troponin 1 promoter (Bhaysar et al, 1996); the Na+/Ca2+ exchanger promoter (Barnes et al., 1997), the dystrophin promoter (Kimura et al., 1997), the creatine kinase promoter (Ritchie, M. E., 1996), the alpha7 integrin promoter (Ziober & Kramer, 1996), the brain natriuretic peptide promoter (LaPointe et al, 1996) and the alpha B-crystallin/small heat shock protein promoter (Gopal-Srivastava, R., 1995), alpha myosin heavy chain promoter (Yamauchi-Takihara et al., 1989) and the ANF promoter (LaPointe et al., 1988).

Guidance in the construction of vectors and the introduction thereof into a subject for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

In one embodiment, a tissue-engineered pump is fabricated as described herein and a population of cells within the pump is transfected with a photosensitive membrane transport mechanism to generate a heterogeneous population of cells in the pump. When stimulated with the appropriate wavelength of light, the induced action potential of the optical stimulated cell propagates and activates the remaining non-transfected tissue through gap junctions. A light-sensitive ion channel transfected pacemaker can be partially created on a scaffold as described herein, using various patterning techniques (e.g. virus patterning techniques and cell patterning techniques). For virus patterning techniques, virus can be localized with Poly(ethylenimine)-catechol (PEI-C) which partially transfects tissue to express a light sensitive ion channel. (PEI-C is easily bound to virus through charge interactions between PEI and virus and improves adhesive property of virus due to adhesive property of catechol.)

Following DNA transfer, the cells are screened to confirm expression and function of the exogenous gene encoding a photosensitive membrane transport mechanism using methods routine to one of ordinary skill in the art. For example, screening may include patch-clamp analysis to confirm the generation of action potentials, that such action potentials are induced by an opsin, and/or to quantify the transmembrane current, e.g., conduction velocity, duration, action potential morphology, generated by the opsin, optical mapping of cells, which when stained with a voltage-sensitive membrane dye, e.g., R11237, can be used to interpret subtle changes in fluorescence corresponding directly to changes in transmembrane potential, thus maintaining both spatial and temporal information about the cells, and ion channel expression by staining with e.g., β-tubulin III, atrial naturitic peptide, Sca-1, myosin, adrenergic receptors and/or muscarinic receptors III. Uses of the Devices of the Invention The devices of the invention may be used in vitro or in vivo. For example, the devices of the invention are useful for, among other things, measuring muscle activities or functions, investigating muscle developmental biology and disease pathology, as well as in drug discovery and toxicity testing in vitro.

Accordingly, the present invention also provides methods for identifying a compound that modulates a muscle tissue function. The methods include providing a device of the invention; contacting the engineered muscle tissue with a test compound; and determining the effect of the test compound on a contractile function in the presence and absence of the test compound, wherein a modulation of the contractile function in the presence of the test compound as compared to the muscle tissue function in the absence of the test compound indicates that the test compound modulates a muscle tissue function, thereby identifying a compound that modulates a muscle tissue function.

In another aspect, the present invention also provides methods for identifying a compound useful for treating or preventing a muscle disease. The methods include providing a device of the invention; contacting the engineered muscle tissue with a test compound; and determining the effect of the test compound on a muscle tissue function in the presence and absence of the test compound, wherein a modulation of the muscle tissue function in the presence of the test compound as compared to the muscle tissue function in the absence of the test compound indicates that the test compound modulates a muscle tissue function, thereby identifying a compound useful for treating or preventing a muscle disease.

The methods of the invention generally comprise determining the effect of a test compound on engineered muscle tissues as a whole, however, the methods of the invention may comprise further evaluating the effect of a test compound on an individual cell type(s) of the muscle tissue.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a plurality of muscle tissues with a test compound) is intended to include any form of interaction (e.g., direct or indirect interaction) of a test compound and a muscle tissue or a plurality of muscle tissues. The term contacting includes incubating a compound and a muscle tissue or plurality of muscle tissues together (e.g., adding the test compound to a muscle tissue or plurality of muscle tissues in culture).

Test compounds, may be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to a muscle tissue by any suitable means. For example, the test compound may be added drop-wise onto the surface of a device of the invention and allowed to diffuse into or otherwise enter the device, or it can be added to the nutrient medium and allowed to diffuse through the medium. In one embodiment, a solution comprising the test compound may also comprise fluorescent particles, and a muscle cell function may be monitored using Particle Image Velocimetry (PIV).

Numerous physiologically relevant parameters, e.g., muscle activities, e.g., biomechanical and electrophysiological activities, can be evaluated using the methods and devices of the invention. For example, in one embodiment, the devices of the present invention can be used in contractility assays for contractile cells, such as muscular cells or tissues, such as chemically and/or electrically stimulated contraction of muscle tissue. In addition, the differential contractility of different muscle cell types to the same stimulus (e.g., pharmacological and/or electrical) can be studied.

In another embodiment, the devices of the present invention can be used for measurements of solid stress due to osmotic swelling of cells. For example, as the cells swell the muscle tissue will bend and as a result, volume changes, force and points of rupture due to cell swelling can be measured.

In another embodiment, the devices of the present invention can be used for pre-stress or residual stress measurements in cells. For example, vascular smooth muscle cell remodeling due to long term contraction in the presence of endothelin-1 can be studied.

Further still, the devices of the present invention can be used to study the loss of rigidity in tissue structure after traumatic injury. Traumatic stress can be applied to vascular smooth muscle thin films as a model of vasospasm. These devices can be used to determine what forces are necessary to cause vascular smooth muscle to enter a hyper-contracted state. These devices can also be used to test drugs suitable for minimizing vasospasm response or improving post-injury response and returning vascular smooth muscle contractility to normal levels more rapidly.

In other embodiments, the devices of the present invention can be used to study biomechanical responses to paracrine released factors (e.g., vascular smooth muscle dilation due to release of nitric oxide from vascular endothelial cells, or cardiac myocyte dilation due to release of nitric oxide).

In other embodiments, the devices of the invention can be used to evaluate the effects of a test compound on an electrophysiological parameter, e.g., an electrophysiological profile comprising a voltage parameter selected from the group consisting of action potential, action potential morphology, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release, and wave propagation velocity. For example, a decrease in a voltage or calcium flux parameter of a muscle tissue comprising cardiomyocytes upon contacting the tissue with a test compound, would be an indication that the test compound is cardiotoxic.

In yet another embodiment, the devices of the present invention can be used in pharmacological assays for measuring the effect of a test compound on the stress state of a tissue. For example, the assays may involve determining the effect of a drug on tissue stress and structural remodeling of the muscle tissue. In addition, the assays may involve determining the effect of a drug on cytoskeletal structure (e.g., sarcomere alignment) and, thus, the contractility of the muscle tissue.

In still other embodiments, the devices of the present invention can be used to measure the influence of biomaterials on a biomechanical response. For example, differential contraction of vascular smooth muscle remodeling due to variation in material properties (e.g., stiffness, surface topography, surface chemistry or geometric patterning) of the scaffold can be studied.

In further embodiments, the devices of the present invention can be used to study functional differentiation of stem cells (e.g., pluripotent stem cells, multipotent stem cells, induced pluripotent stem cells, and progenitor cells of embryonic, fetal, neonatal, juvenile and adult origin) into contractile phenotypes. For example, undifferentiated cells, e.g., stem cells, are coated on the thin films and differentiation into a contractile phenotype is observed by thin film bending. Differentiation into an anisotropic tissue may also be observed by quantifying the degree of alignment of sarcomeres and/or quantifying the orientational order parameter (OOP). Differentiation can be observed as a function of: co-culture (e.g., co-culture with differentiated cells), paracrine signaling, pharmacology, electrical stimulation, magnetic stimulation, thermal fluctuation, transfection with specific genes, chemical and/or biomechanical perturbation (e.g., cyclic and/or static strains).

In one embodiment a biomechanical perturbation is stretching of, e.g., the scaffold during tissue formation. In one embodiment, the stretching is cyclic stretching. In another embodiment, the stretching is sustained stretching.

In one embodiment, the scaffold is stretched at an appropriate time after cell seeding that is based on the type(s) of cells seeded. In one embodiment, the scaffold is stretched at about minutes, hours, or days after cell seeding onto a scaffold. In one embodiment, the scaffold is stretched at about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 hours after cell seeding onto a scaffold.

In another embodiment, the devices of the invention may be used to determine the toxicity of a test compound by evaluating, e.g., the effect of the compound on an electrophysiological response of a muscle tissue. For example, opening of calcium channels results in influx of calcium ions into the cell, which plays an important role in excitation-contraction coupling in cardiac and skeletal muscle fibers. The reversal potential for calcium is positive, so calcium current is almost always inward, resulting in an action potential plateau in many excitable cells. These channels are the target of therapeutic intervention, e.g., calcium channel blocker sub-type of anti-hypertensive drugs. Candidate drugs may be tested in the electrophysiological characterization assays described herein to identify those compounds that may potentially cause adverse clinical effects, e.g., unacceptable changes in cardiac excitation, that may lead to arrhythmia.

For example, unacceptable changes in cardiac excitation that may lead to arrhythmia include, e.g., blockage of ion channel requisite for normal action potential conduction, e.g., a drug that blocks $Na^+$ channel would block the action potential and no upstroke would be visible; a drug that blocks $Ca^{2+}$ channels would prolong repolarization and increase the refractory period; blockage of $K^+$ channels would block rapid repolarization, and, thus, would be dominated by slower $Ca^{2+}$ channel mediated repolarization.

In addition, metabolic changes may be assessed to determine whether a test compound is toxic by determining, e.g., whether contacting with a test compound results in a decrease in metabolic activity and/or cell death. For example, detection of metabolic changes may be measured using a variety of detectable label systems such as fluormetric/chrmogenic detection or detection of bioluminescence using, e.g., AlamarBlue fluorescent/chromogenic determination of REDOX activity (Invitrogen), REDOX indicator changes from oxidized (non-fluorescent, blue) state to reduced state (fluorescent, red) in metabolically active cells; Vybrant MTT chromogenic determination of metabolic activity (Invitrogen), water soluble MTT reduced to insoluble formazan in metabolically active cells; and Cyquant NF fluorescent measurement of cellular DNA content (Invitrogen), fluorescent DNA dye enters cell with assistance from permeation agent and binds nuclear chromatin. For bioluminescent assays, the following exemplary reagents may be used: Cell-Titer Glo luciferase-based ATP measurement (Promega), a thermally stable firefly luciferase glows in the presence of soluble ATP released from metabolically active cells.

The devices of the invention are also useful for evaluating the effects of particular delivery vehicles for therapeutic agents e.g., to compare the effects of the same agent administered via different delivery systems, or simply to assess whether a delivery vehicle itself (e.g., a viral vector or a liposome) is capable of affecting the biological activity of the muscle tissue. These delivery vehicles may be of any form, from conventional pharmaceutical formulations, to gene delivery vehicles. For example, the devices of the invention may be used to compare the therapeutic effect of the same agent administered by two or more different delivery systems (e.g., a depot formulation and a controlled release formulation). The devices and methods of the invention may also be used to investigate whether a particular vehicle may have effects of itself on the tissue. As the use of gene-based therapeutics increases, the safety issues associated with the various possible delivery systems become increasingly important. Thus, the devices of the present invention may be used to investigate the properties of delivery systems for nucleic acid therapeutics, such as naked DNA or RNA, viral vectors (e.g., retroviral or adenoviral vectors), liposomes and the like. Thus, the test compound may be a delivery vehicle of any appropriate type with or without any associated therapeutic agent.

Furthermore, the devices of the present invention are a suitable in vitro model for evaluation of test compounds for therapeutic activity with respect to, e.g., a muscular and/or neuromuscular disease or disorder. For example, the devices of the present invention (e.g., comprising muscle cells) may be contacted with a candidate compound by, e.g., diffusion of the test compound added drop-wise on the surface of a muscle tissue, diffusion of a test compound through the culture medium, or immersion in a bath of media containing the test compound, and the effect of the test compound on muscle activity (e.g., a biomechanical and/or electrophysiological activity) may be measured as described herein, as compared to an appropriate control, e.g., an untreated muscle tissue. Alternatively, a device of the invention may be bathed in a medium containing a candidate compound, and then the cells are washed, prior to measuring a muscle activity (e.g., a biomechanical and/or electrophysiological activity) as described herein. Any alteration to an activity determined using the device in the presence of the test agent (as compared to the same activity using the device in the absence of the test compound) is an indication that the test compound may be useful for treating or preventing a muscle disease, e.g., a neuromuscular disease.

For use in the methods of the invention, the cells seeded onto the muscle tissue may be normal muscle cells (cardiac, smooth, or skeletal muscle cells), abnormal muscle cells (e.g., those derived from a diseased tissue, or those that are physically or genetically altered to achieve a abnormal or pathological phenotype or function), normal or diseased muscle cells derived from embryonic stem cells or induced pluripotent stem cells, or normal cells that are seeded/printed onto the film in an abnormal or aberrant configuration. In some cases, both muscle cells and neuronal cells are present on the film.

Evaluation of muscle activity includes determining the degree of contraction, the rate or frequency of contraction/rate of relaxation compared to a normal control or control tissue in the absence of the test compound. An increase in the degree of contraction or rate of contraction indicates that the compound is useful in treatment or amelioration of pathologies associated with myopathies such as muscle weakness or muscular wasting. Such a profile also indicates that the test compound is useful as a vasocontractor. A decrease in the degree of contraction or rate of contraction is an indication that the compound is useful as a vasodilator and as a therapeutic agent for muscle or neuromuscular disorders characterized by excessive contraction or muscle thickening that impairs contractile function.

Compounds evaluated in this manner are useful in treatment or amelioration of the symptoms of muscular and neuromuscular pathologies such as those described below. Muscular Dystrophies include Duchenne Muscular Dystrophy (DMD) (also known as Pseudohypertrophic), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD). Motor Neuron Diseases include Amyotrophic Lateral Sclerosis (ALS) (Also known as Lou Gehrig's Disease), Infantile Progressive Spinal Muscular Atrophy (SMA, SMA1 or WH) (also known as SMA Type 1, Werdnig-Hoffman), Intermediate Spinal Muscular Atrophy (SMA or SMA2) (also known as SMA Type 2), Juvenile Spinal Muscular Atrophy (SMA, SMA3 or KW) (also known as SMA Type 3, Kugelberg-Welander), Spinal Bulbar Muscular Atrophy (SBMA) (also known as Kennedy's Disease and X-Linked SBMA), Adult Spinal Muscular Atrophy (SMA). Inflammatory Myopathies include Dermatomyositis (PM/DM), Polymyositis (PM/DM), Inclusion Body Myositis (IBM). Neuromuscular junction pathologies include Myasthenia Gravis (MG), Lambert-Eaton Syndrome (LES), and Congenital Myasthenic Syndrome (CMS). Myopathies due to endocrine abnormalities include Hyperthyroid Myopathy (HYPTM), and Hypothyroid Myopathy (HYPOTM). Diseases of peripheral nerves include Charcot-Marie-Tooth Disease (CMT) (Also known as Hereditary Motor and Sensory Neuropathy (HMSN) or Peroneal Muscular Atrophy (PMA)), Dejerine-Sottas Disease (DS) (Also known as CMT Type 3 or Progressive Hypertrophic Interstitial Neuropathy), and Friedreich's Ataxia (FA). Other Myopathies include Myotonia Congenita (MC) (Two forms: Thomsen's and Becker's Disease), Paramyotonia Congenita (PC), Central Core Disease (CCD), Nemaline Myopathy (NM), Myotubular Myopathy (MTM or MM), Periodic Paralysis (PP) (Two forms: Hypokalemic-HYPOP- and Hyperkalemic-HYPP) as well as myopathies associated with HIV/AIDS.

The methods and devices of the present invention are also useful for identifying therapeutic agents suitable for treating or ameliorating the symptoms of metabolic muscle disorders such as Phosphorylase Deficiency (MPD or PYGM) (Also known as McArdle's Disease), Acid Maltase Deficiency (AMD) (Also known as Pompe's Disease), Phosphofructokinase Deficiency (PFKM) (Also known as Tarui's Disease), Debrancher Enzyme Deficiency (DBD) (Also known as Cori's or Forbes' Disease), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD).

In addition to the disorders listed above, the screening methods described herein are useful for identifying agents suitable for reducing vasospasms, heart arrhythmias, and cardiomyopathies.

Vasodilators identified as described above are used to reduce hypertension and compromised muscular function associated with atherosclerotic plaques. Smooth muscle cells associated with atherosclerotic plaques are characterized by an altered cell shape and aberrant contractile function. Such cells are used to populate a tissue, exposed to candidate compounds as described above, and muscular function evaluated as described above. Those agents that improve cell shape and function are useful for treating or reducing the symptoms of such disorders.

In vivo uses of the devices of the invention include, for example, use as implantable medical devices. For example, a subject having a chronic heart condition would benefit from the implantation of a device of the invention as a ventricular assist device since current devices are purely mechanical in design and suffer from unique failure modes and cause thrombosis while the devices of the present invention can be powered by readily delivered chemical energy, rather than relying on percutaneous (undesirable and infection prone) lines to external power supplies and controllers.

Additionally, exemplary tissue-engineered pump assemblies and valve assemblies may be implanted at any suitable location within an animal body to improve poor cardiovascular circulation. An exemplary assembly may be placed, for example, in a mammalian heart. An exemplary assembly may be placed, as another example, near or in the feet of a diabetic person as a local pump to improve circulation near the feet.

The devices of the invention may be used as transient treatment medical devices, e.g., in "bridge to recovery" applications and blood pumping in coronary artery bypass graft ("bypass") or other surgeries in which heart contractility must be temporarily stopped during repair.

Furthermore, the devices of the invention may simulate cyclical cardiomyocyte contraction against a fluid load, which in turn may re-constitute some organ-level effects important in the translational medicine pipeline.

The tissue-engineered valves of the invention may be used as replacement valves in subjects having defective tricuspid valves, mitral valves, semilunar valves and/or venous valve (for example in subjects having poor peripheral circulation, such as diabetic subjects).

For in vivo applications, the exact size and shape of the devices of the present invention are species and patient specific. For example, pediatric patients may require smaller devices than adult patients. Pediatric aortic diameters can range from about 10 mm-20 mm (i.e., the diameter of the aortic annuls). Adults can have an aortic annulus ranging from 20-35 mm in diameter.

One benefit of the valves and devices of the present invention is that they can be fabricated and custom-sized to fit the subject. Additionally, the tissue-engineered valves of the present invention that have been fabricated using autologous cells do not require the subject to undergo immunosuppressive therapy. Moreover, the engineered tissues will be integrated into the natural tissue as cells from the subject will integrate into the scaffold and remodel the scaffold.

Any suitable means for accessing the subject's heart and attaching the devices may be used, such as thoracic surgery or transmyocardial catheter delivery.

The present invention is next described by means of the following examples. However, the use of these and other examples anywhere in the specification is illustrative only, and in no way limits the scope and meaning of the invention or of any exemplified form. The invention is not limited to any particular preferred embodiments described herein. Many modifications and variations of the invention may be apparent to those skilled in the art and can be made without departing from its spirit and scope. The contents of all references, patents and published patent applications cited throughout this application, including the figures, are incorporated herein by reference.

EXAMPLES

Example 1

A Tissue Engineered Jellyfish with Biomimetic Propulsion

Materials and Methods

Design of Medusoid Muscle Architecture.

Initial medusoid muscle architecture mimicked the comparatively sparse muscle layout of jellyfish ephyrae (FIGS. 6a and 6b) but was found to generate insufficient stresses for robust bell contraction. A medusoid muscle layout featuring extensive radial components designed for maximal lobe bending was therefore implemented whereas the central ring muscle facilitated lobe synchronization by providing a rapid pathway for circumferential action potential propagation (FIGS. 6c and d). This design exploited the fact that both maximal force generation and maximal conduction velocity occurs along the longitudinal axis of anisotropic myocardium.

Figure 7A:
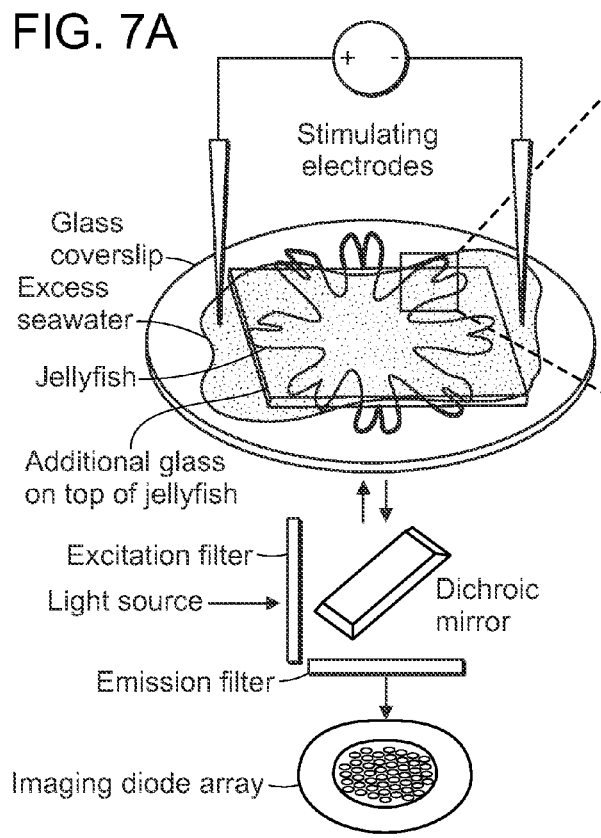
FIGS. 7A-7O depict the confirmation of continuous action potential propagation in Medusoid and Jellyfish striated muscle byptical mapping. a, Set-up of optical mapping system (OMS) for membrane voltage recording in jellyfish muscle stained with RH237. b, Close-up on jellyfish lobe with typical field of view (FOV) on RH237-stained radial muscle. c, FOV overlaid with LED recording array. The two labeled channels are representative for channels recording from muscle tissue (channel 1, light gray) or from mesoglea (channel 2, medium gray). d, Recording traces from the two channels marked in (c) illustrate that only muscle recordings contain voltage signals. e, Filtered data set only contains channels recording from muscle. f-h, Activation times and velocity vectors calculated from filtered data set in (e) illustrate spread of continuous wave front activating the jellyfish muscle. Mean conduction velocity: 1±0.35 cm/s; n=13 FOVs (from 3 animals). i, OMS setup for membrane voltage recording in Medusoid muscle (anisotropic monolayer of cardiomycoytes). j, Close-up on Medusoid micropatterned muscle. k, Typical FOV of RH237-stained muscle tissue overlaid with LED recording array. l, Filtered voltage signal and exemplary trace recorded by single channel. m-o, Activation times and velocity vectors calculated from filtered data set in (l) illustrate spread of continuous wave front activating the Medusoid muscle. Mean conduction velocity: longitudinal, 27±4 cm/s, transverse, 9±1 cm/s; n=4 FOVs (from 2 Medusoid constructs).
Figure 7B:
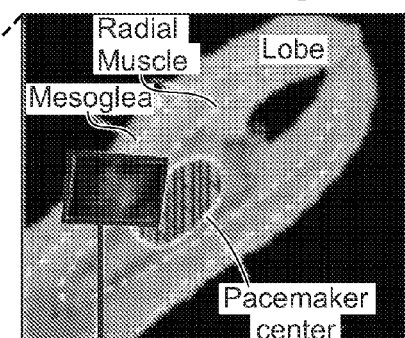
Figure 7C:
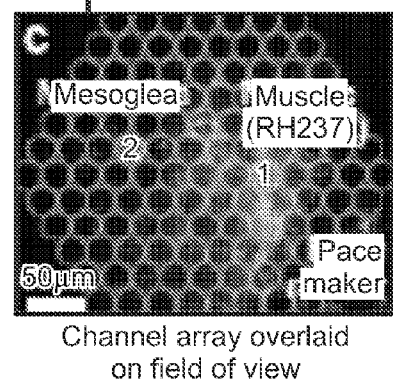
Figure 7D:
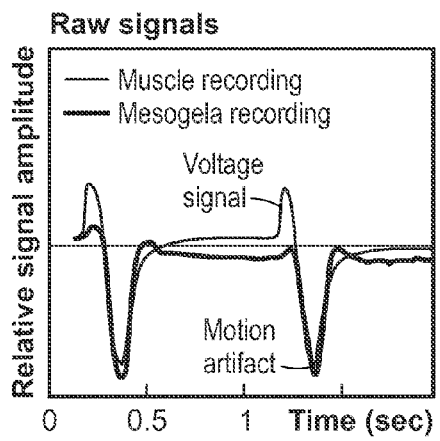
Figure 7E:
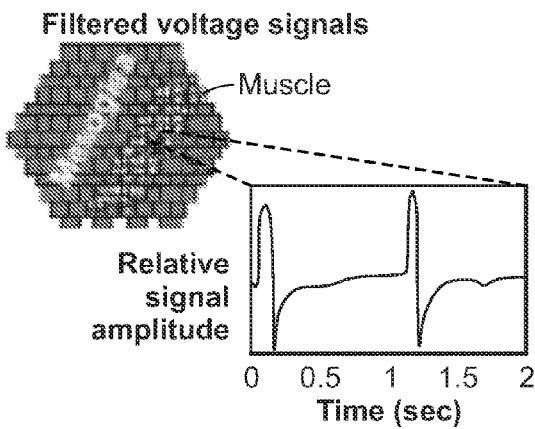
Figure 7F:
Figure 7G:
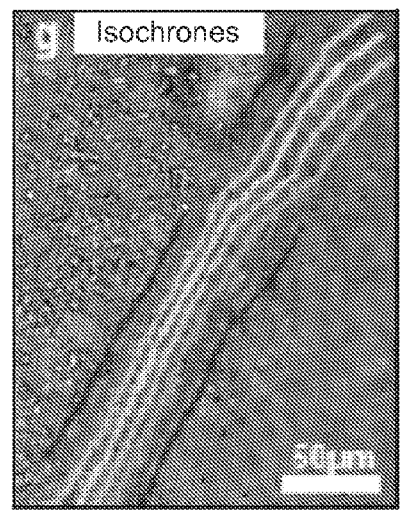
Figure 7H:
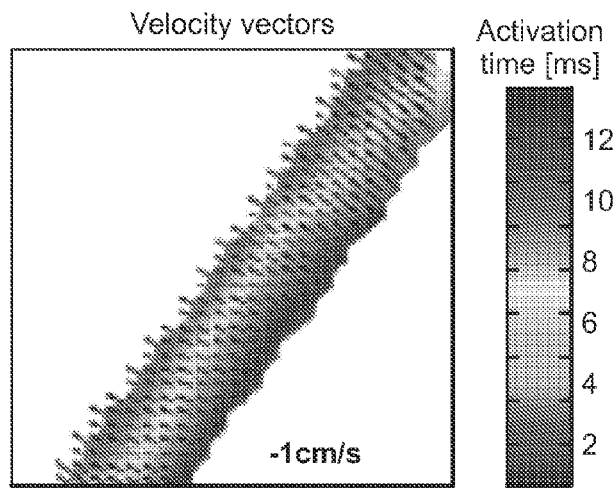
Figure 7I:
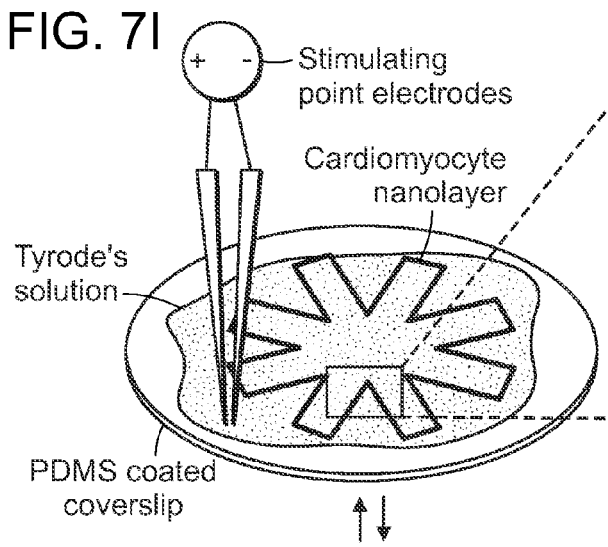
Figure 7J:
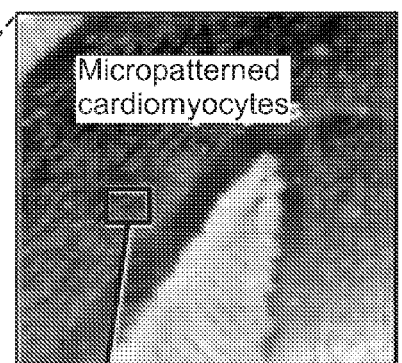
Figure 7K:
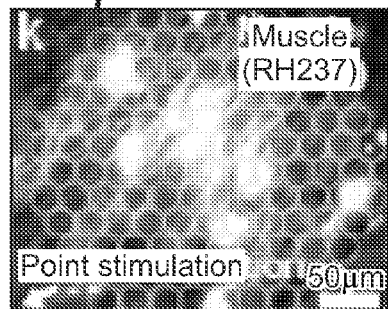
Figure 7L:
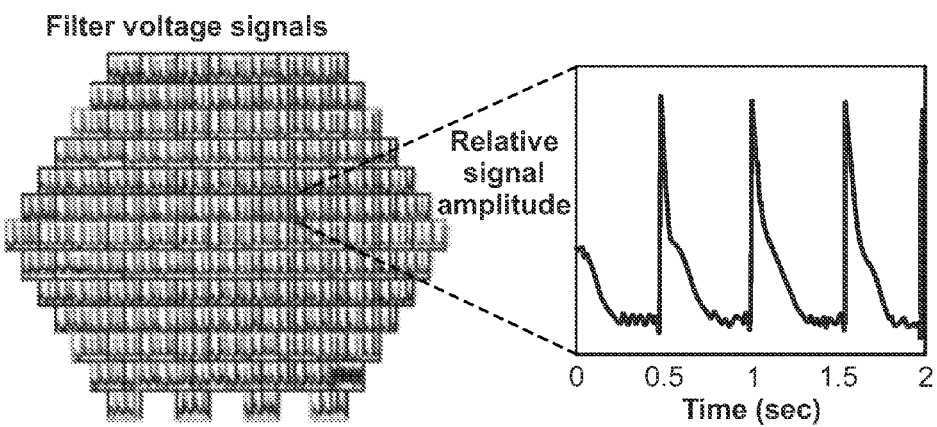
Figure 7M:
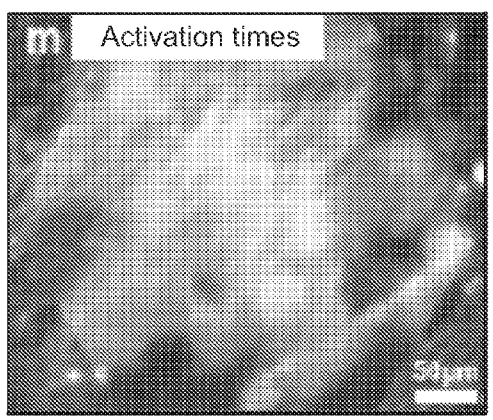
Figure 7N:
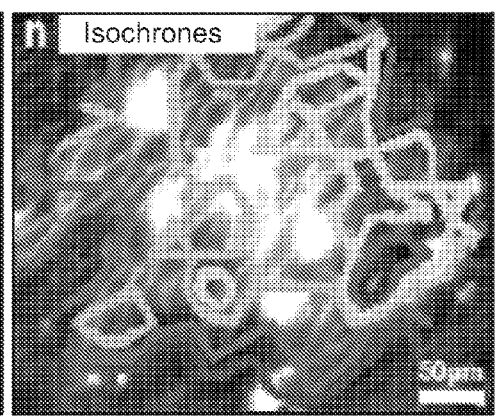
Figure 7O:
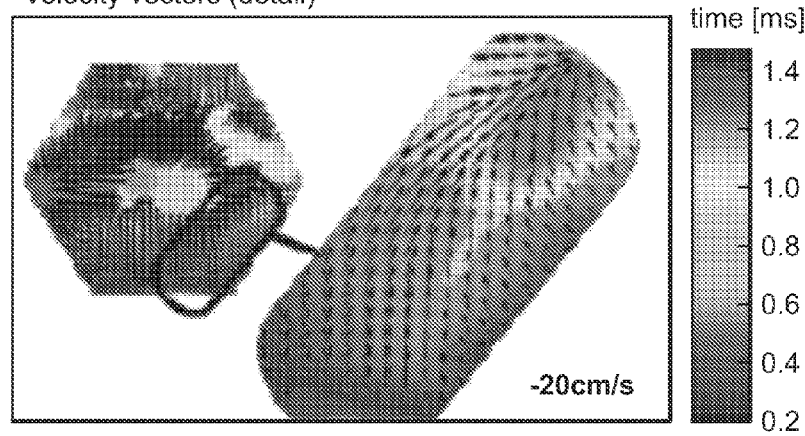

Optical Mapping of Muscle Action Potential Propagation in Jellyfish and Medusoid. Medusoids:

PMDS-coated glass cover slips with cardiomyocyte monolayers of medusoid muscle architecture were assayed in a custom-made optical mapping system (FIGS. 7i-o) by adapting previously described protocols. Briefly, the cultures were incubated for 5 minutes in 8 µM RH-237 voltage-sensitive dye ($I_{ex}/I_{em}$ in DMSO=~550/~800 nm; Molecular Probes) in Tyrode's solution, then washed with Tyrode's solution. During recording, the tissue was placed in Tyrode's solution containing 10 µM excitation-contraction uncoupler blebbistatin, thereby minimizing motion artifacts. All solutions were maintained at 35-37° C. A platinum point electrode connected to a Grass S48 stimulator (Grass technologies, West Warwick, R.I. 02893, USA) was placed ~1 mm above the culture surface (FIG. 7i) and used to apply point stimuli (2 Hz, 5-8 V, 10-ms duration). Imaging was performed using an inverted microscope (Zeiss Axiovert 200; Carl Zeiss MicroImaging, LLC Thornwood, N.Y. 10594, USA) equipped with a 40× Plan-Neofluar (1.3 NA) oil-immersion objective, a fluorescence light source (Hamamatsu L2422 100 Watt Mercury-Xenon lamp) and a filter cube appropriate for RH237 imaging (Zeiss EX BP530-585, DC FT600, EM LP615). Fluorescence shutter opening and closing was synchronized with the pacing stimulus. Membrane voltage signals were optically recorded at 5 Hz using a honeycomb of 124 independent optical fibers, each monitoring an approximately circular field of view of 25 µm in diameter (FIGS. 6j and 6k) and each connected to a discrete photodiode transimpedance amplifier. The outputs of the photodiode amplifiers were digitized by a bank of differential amplifiers and DAQ cards (National Instruments Corporation, Austin, Tex. 78759, USA). Digitized signals were processed using custom-made software implemented in MATLAB (MathWorks, Natick, Mass. 01760, USA) (FIG. 7l). Activation times, defined as the time point of maximum positive slope of the action potential, served to calculate isochronal maps of activation and velocity vector fields across the field of view monitored by the LED array (FIGS. 7m and 7o).

Jellyfish:

Optical mapping in jellyfish (FIG. 7a-7h) was performed as in medusoid coverslips except for the following differences. All procedures were carried out in artificial seawater at room temperature (KENT Marine Sea Salt, KENT Marine Sea, 5401 West Oakwood Park Drive, Franklin, Wis. 53132). Jellyfish swimming muscle proved to be insensitive to all available excitation-contraction uncoupling agents including blebbistatin, cytochalasin D, 2,3-butanedione monoxime (BDM) and dantrolene sodium. Thus, to constrain movement, an additional cover slip was placed on top of the jellyfish using vacuum grease as a spacer. The anode and cathode pole of a platinum pacing electrode were placed into excess seawater protruding from either side of the coverslips to apply electric field stimulation (5-8 V, 10 ms duration) at a rate of 1 Hz (FIG. 7a). This stimulus reliably led to muscle contraction starting near the pacemaker centers within the lobes (FIG. 73b). The optical signals contained motion artifacts due to muscle contractions; however, the difference in relative timing allowed isolation of true voltage signals (FIGS. 7 c and 7d). Subsequently, activation times, isochronal maps and velocity vector fields were calculated as above (FIGS. 7e-7h).

Histochemical Staining and Structural Analysis.

Muscle microstructure in jellyfish and medusoids was visualized by fluorescent staining of actin and sarcomeres. Medusoid-patterned myocardial tissues were cultured on PDMS-coated glass cover slips and stained for F-actin fibers and sarcomeric α-actinin as previously described. Briefly, washed samples were fixed for 15 min in 4% paraformaldehyde and 2.5% Triton X-100 in PBS at 37° C., followed by 1-h incubation with 1:200 dilutions of mouse anti-sarcomeric α-actinin monoclonal primary antibody (Sigma-Aldrich). Samples were then washed and concurrently incubated with 1:200 dilutions of DAPI (Sigma-Aldrich), phalloidin conjugated to Alexa-Fluor 488 (Invitrogen, Carlsbad, Calif. 92008, USA) and goat anti-mouse secondary antibody conjugated to tetramethylrhodamine for 1 h at room temperature. Juvenile jellyfish were anesthetized in 7.5% MgCl2 solution in artificial seawater (1:1) and fixed overnight in 4% paraformaldehyde and 2.5% Triton X-100 in PBS at 4° C. Following fixation the animals were stained overnight at 4° C. with 1:250 dilutions of phalloidin conjugated to Alexa-Fluor 488 (Invitrogen) and DAPI (Sigma-Aldrich). Following staining, jellyfish and medusoid samples were mounted to glass slides and imaged on an inverted light microscope (Model DMI 6000B, Leica Microsystems, International Headquarters, Wetzlar, Germany) in epifluorescence using a Coolsnap HQ digital camera (Roper Scientific Inc, Trenton, N.J. 08619, USA).

Figure 2A:
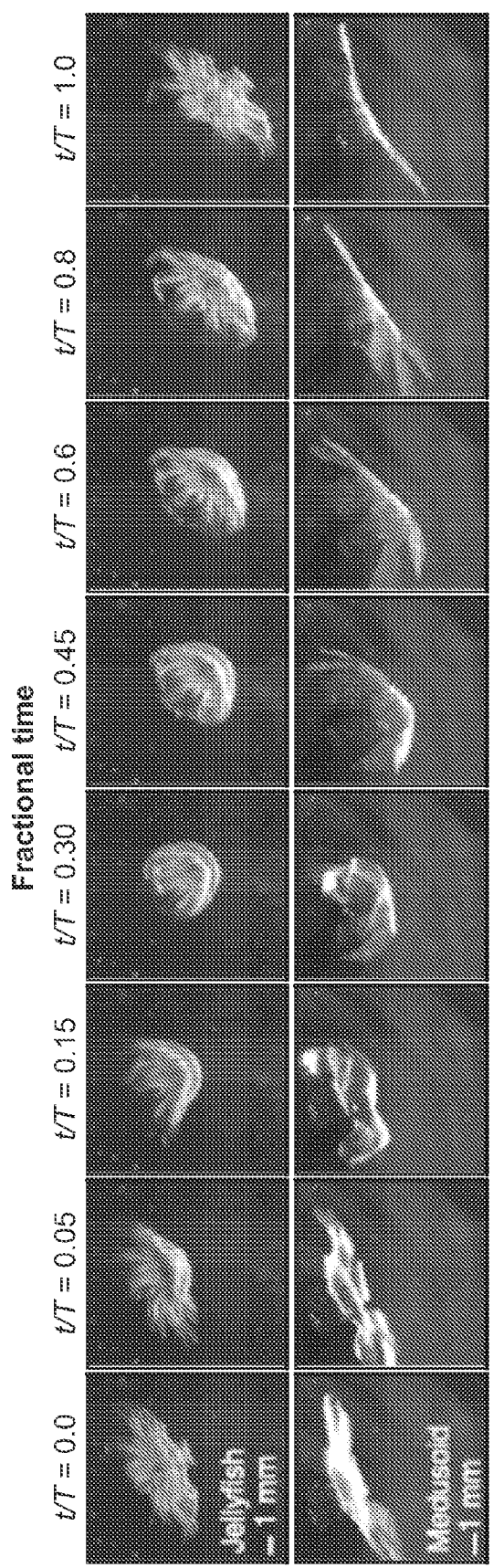
FIGS. 2A-2D depict the engineering of medusoids to exhibit jellyfish-like stroke kinetics. (a) Time lapse of stroke cycle in jellyfish (top) and medusoid paced at 1 Hz (bottom); t, time (sec) elapsed since start of stroke cycle; T, duration of stroke cycle; here: jellyfish, T=0.3 s; medusoid, T=1.0 s. (b) Average trace of angular velocity of individual bell lobes throughout stroke cycle in juvenile jellyfish and medusoids (n=9 lobes each). Inset illustrates characteristic parameters of stroke cycle (top) and velocity-time graph (bottom). $T_{power/recovery}$, duration of power/recovery stroke; $U_{power/recovery}$, velocity of power/recovery stroke; $\hat{U}_{power/recovery}$, peak velocity of power/recovery stroke; $t_{power/recovery}$, time point of peak power/recovery stroke velocity. (c,d) Box-plot representation. Bull's eyes, median; lower edge of box, 25th percentile; upper edge of box, 75th percentile; whiskers, extreme data points. (c) Relative asynchrony of lobe contraction. Asynchrony did not differ significantly in jellyfish and medusoids (P=0.7, Wilcoxon rank sum test, n=4 lobe pairs each). $\Delta t_{power}$, difference between time points of peak power stroke velocities in pair of lobes. (d) Ratio of maximal lobe velocities during power and recovery stroke did not differ significantly in jellyfish and medusoids (P=0.7, Wilcoxon rank sum test, n=9 lobes each).
Figure 2B:
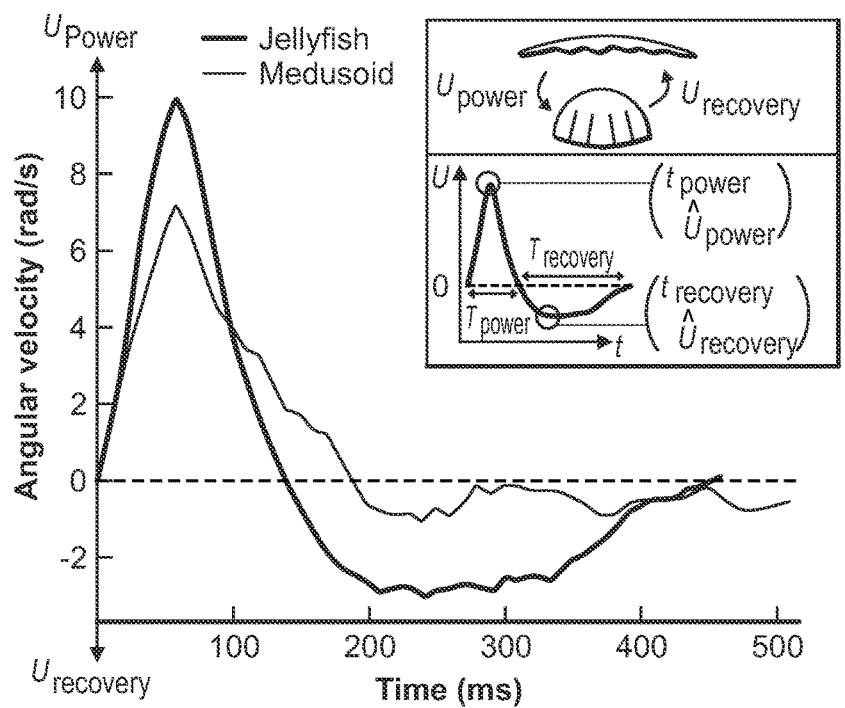

Custom-made image processing software was used to quantify actin fiber alignments. The code was adapted from biometric fingerprint algorithms (Peter Kovesi, School of Computer Science & Software Engineering, University of Western Australia) and implemented in MATLAB. Briefly, intensity images of actin fiber stains (FIG. 8a) were normalized and thresholded to create a binary mask blocking actin-free areas (FIG. 8b). From the masked image intensities, we calculated a field of orientation vectors that "flow" tangential to the edges (like velocity vectors along streamlines) and thus correspond to fiber orientation (FIG. 8c). Dominant orientation angles were visualized through the histogram of orientation vector angles (FIG. 2b and FIG. 8d). In order to quantify the degree of fiber alignment a derivation of the orientational order parameter (OOP), which is commonly used to determine the degree of order in anisotropic media such as liquid crystals and polymeric solutions and has also been used to quantify cell alignment was employed. Briefly, for each nonempty pixel i, an orientation unit vector $r_i=[r_{ix}, r_{iy}]$ that was used to form the pixel orientational tensor was constructed $$T_i = \begin{bmatrix} r_{ix}, r_{ix} & r_{ix}, r_{iy} \\ r_{iy}, r_{ix} & r_{iy}, r_{iy} \end{bmatrix}$$

Image orientational tensor T is found by averaging over all pixels, i=1 . . . n, followed by normalization. The largest eigenvalue of T corresponds to the orientational order parameter (OOP) and ranges—as T is normalized—from 0 to 1, the former indicating completely random orientation, the latter reporting perfect alignment of all vectors. OOPs calculated from fields of view of different samples can be assumed to be independent of each other and normally distributed, such that a paired t-test could be used to compare jellyfish and medusoids.

Medusoid Fabrication.

The fabrication of free-swimming medusoid constructs (FIG. 9) closely followed the process described for building muscular thin films. First, titanium or acrylic casting molds were created by milling a 100-μm high plateau with medusoid body geometry from a circular base. The casting molds were cleaned by sonicating for 20 min in 95% ethanol and air dried. Next, the molds were spin-coated for 1 min at 6,000 RPM with poly(N-isopropylacrylamide) (PIPAAm, Polysciences, Inc., Warrington, Pa. 18976, USA) at 10% in 1-butanol (w/v). Sylgard 184 (Dow Corning Corporation, Midland, Mich. 48686, USA) polydimethylsiloxane (PDMS) elastomer was mixed at a 10:1 base to curing agent ratio and allowed to cure for 3.5 h at room temperature, then spin-coated on top of the PIPAAm coated molds for 1 min at 4,500 RPM. The resulting medusoid-shaped PDMS films were ~22 μm thick. The films were cured for a minimum of 4 h at 65° C., followed by surface functionalization. First, the PDMS film surface was oxidized using UV ozone (Model No. 342, Jelight Company Inc., Irvine, Calif. 92618, USA) in order to increase hydrophilicity and facilitate protein transfer during microcontact printing. Medusoid-muscle patterned PDMS stamps cast from negatively patterned photoresist silicon wafers were inked for 2 h with human fibronectin (50 μg/mL in deionized water; Sigma-Aldrich Co. LLC Natick, Mass. 0176, USA). Freshly oxidized medusoid substrates were placed under a dissection scope for microcontact printing. The air-dried stamps were lowered onto the medusoid substrates and gently pushed down to achieve efficient fibronectin transfer. The micropatterned medusoid substrates were then placed into 6-well culture dishes equipped with custom-made height adaptor that leveled the surface to promote homogeneous cell seeding. Prior to cell seeding the samples were sterilized by 15 min exposure to the UV light of the culturing hood.

Neonatal rat ventricular cardiomyocytes were isolated from 2-day old neonatal Sprague-Dawley using published methods. All procedures were approved by the Harvard Animal Care and Use Committee. Cells were seeded at a density of 1 million cells per well of a 6-well dish. Standard culture media were used (M199 culture medium supplemented with 0.1 mM MEM nonessential amino acids, 10% heat-inactivated FBS, 10 mM HEPES, 3.5 g/L glucose, 2 mM L-glutamine, 2 mg/L vitamin B-12, and 50 U/ml penicillin). Samples were incubated under standard conditions at 37° C. and 5% $CO_2$. At 6 h post seeding 50 nM epinephrine (Sigma-Aldrich) was added to the media. At 24 h post seeding the medium was replaced to remove epinephrine and cellular debris. At 48 h post seeding the media was exchanged with maintenance media (M199 media supplemented as above but with 2% FBS). At 72 hour post seeding the media was exchanged with maintenance media once again until use at 4 day post seeding.

Medusoids were released from their titanium or acrylic molds after 4 d of culture when the cardiomyocytes had formed a confluent 2D tissue. The samples were removed from the incubator and placed into a Petri dish filled with 37° C. normal Tyrode's solution, an extracellular mammalian electrolyte at pH 7.4 suitable for in vitro contractility assay. Tyrode's solution was prepared from powdered formulation (Sigma-Aldrich, SKU T2145). The solution was allowed to cool below 35° C. so that the temperature-sensitive, sacrificial layer of PIPAAm began to dissolve, allowing for the medusoids to be peeled off from the casing molds aided by fine forceps.

Electric Field Stimulation of Muscle Contraction in Medusoids.

Figure 10:
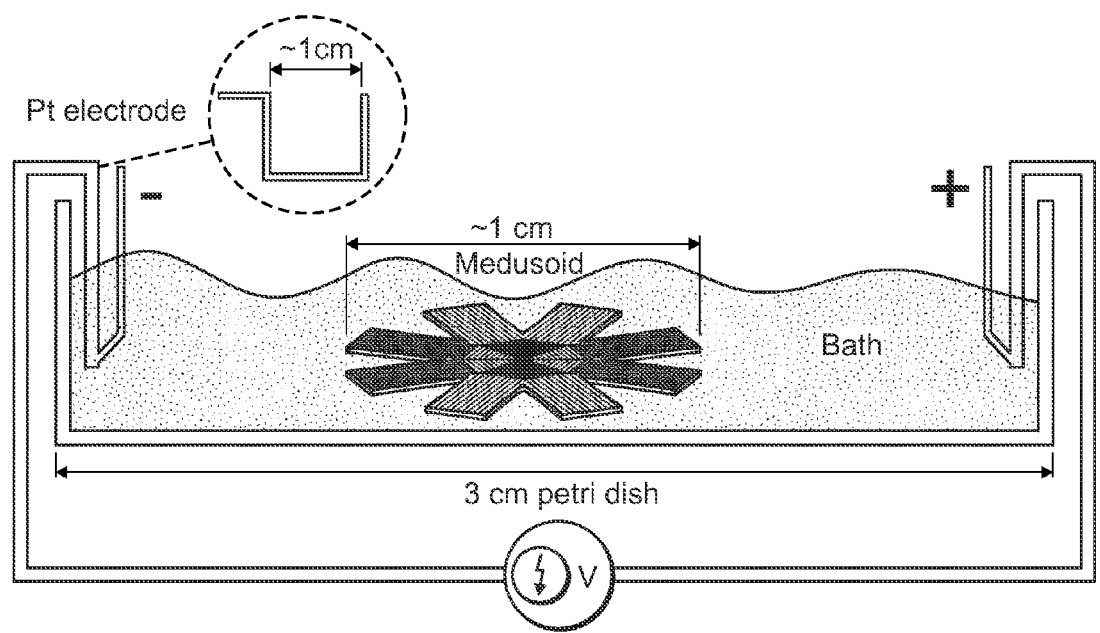
FIG. 10 depicts the experimental set-up for field stimulation of Medusoid constructs. An external field stimulator (Myopacer, IonOptix Corp.) generates monophasic square pulses (5-10 V, 10 ms duration, maximal current 65 mA) delivered to the bath (about 10 ml Tyrode's solution at 37° C.) by two U-shaped platinum electrodes flanking the construct. Pacing frequency ranged from 0.5 to 2 Hz.

Medusoid contraction was initiated and controlled via electric field stimulation. For this, the medusoid tank was equipped with two U-shaped platinum electrodes installed at opposite walls of the tank and connected to a voltage pulse generator (MyoPacer Cell Stimulator, IonOptix, Milton, Mass. 02186, USA) for electric field stimulation of the tissue constructs (FIG. 10). Monophasic square pulses at 1 Hz, 2.5 V/cm and 10-ms duration resulted in reliable capture.

Design of Medusoid Geometry and Modeling of Fluid-Solid Interactions.

Medusoid body shape was modeled after the lobed geometry of juvenile jellyfish as this design enables compression-free bell contraction. Outer body diameter and number of lobes were kept constant across all medusoid designs while varying relative lobe length and distal lobe divergence (FIG. 11a). Parameter space was further constrained by two functional objectives. First, lobe geometry was chosen to promote the formation of overlapping boundary layers along the lobe surface (FIG. 11b), effectively converting the interlobal gaps into additional paddle surface and increasing bell drag. Without boundary layer overlap, propulsion becomes inefficient as fluid leaks through the gaps (FIG. 11c). Second, lobe dimensions were constrained by considerations of mechanical stability, feasibility of fabrication and freedom of motion (FIG. 11d). In particular, lobe divergence and relative length were bounded to prevent lobes from twisting and interfering with each other during contraction.

The relation between bell geometry and drag was studied through a simple fluid-solid interaction model. Lobes were represented as n continuous arrays of elliptical cylinders perpendicular to the flow (FIG. 11e). Each array corresponded to a radial lobe position $r_i$, with i=1 ... n, and was characterized by parameters, $b_i$, lobe width; $L_i$, width of lobe plus adjacent gap; N, number of lobes; v, kinematic fluid viscosity; and $U_i$, fluid velocity which is the product of $r_i$ and angular velocity ω. These parameters in turn determined local array properties Pi, porosity; $Re_i$, Re-Reynolds number; and $A_i$, reference area (FIG. 11f):

$$P_i = (L_i - b_i) L_i^{-1} \quad (1)$$

$$Re_i = b_i U_i v^{-1} \quad (2)$$

$$A_i = (r_{i+1} - r_i) b_i N \quad (3)$$

The drag factors of circular and elliptical cylinders at Reynolds numbers relevant for medusoid lobe contraction (Re=0.1-20) have been characterized empirically as a function of Re and P. Interpolation of the published data across our parameter space of interest allowed us to estimate local drag factor $Cd_i$ for each radial lobe position (FIG. 11g). Total bell drag was calculated by summing local drag over all radial positions $$\text{Drag}_p = \sum_{i=1}^{n} \frac{1}{2} \rho Cd_i A_i U_i^2$$

where n was chosen high enough to approximate integration, subscript "p" stands for prediction, and ρ is fluid density. We validated the model by empirically determining the relative magnitude of drag factors of two sets of medusoid-shaped and medusoid-sized acrylic discs ("medusoid dummies"), varying systematically in lobe divergence within each set, and varying in relative lobe length across sets. The empirical order of drag factors within each set was compared to the order predicted by the model. Empirical drag data were obtained by measuring terminal sinking velocities of medusoid dummies in a cylindrical column containing glycerol-water solutions. Viscosity was adjusted for each run to achieve similar lobe Reynolds numbers for all tested shapes. The column was 20 cm in width and 50 cm in height, minimizing edge effects and allowing the shapes to travel at least 30 cm at terminal velocity before reaching the bottom. The dummies were released electromagnetically to ensure zero starting velocity and avoid tilting. A metal weight attached to the center of the acrylic disc served the dual purpose of responding to the electromagnetic field and lowering the center of mass to stabilize the falling trajectory. Terminal sinking velocities were determined from video recordings of the fall. We then applied equation $$Cd_e = \frac{2 \times W}{\delta U_T^2 A}$$

to calculate empirical drag factors $Cd_e$ with UT, terminal velocity, A, reference area and W, weight of the medusoid dummy (Supplementary FIG. 6h) 40. Predicted drag factors were derived by computing total drag from equation (4) with Ui=UT for all radial positions, and applying $$Cd_p = \frac{2 \times \text{Drag}_p}{\delta A U_T^2}$$

For both sets of medusoid dummies it was found that empirical and predicted orders of normalized drag factors were consistent. Importantly, this order was independent of the order of average lobe Reynolds numbers (FIG. 11i). These results, although based on rigid medusoid dummies, suggested that the model was suitable for predicting the relative performance of actual medusoid tissue constructs with different geometries. We subsequently computed total bell drag of medusoid tissue constructs as a function of relative lobe length and divergence (FIG. 11j). Flow parameters were adjusted to live tissue conditions, with cell media viscosity v=0.8×10⁻⁶ m²s⁻¹ and average muscle construct velocity ω=2.5 rad s⁻¹. In general, higher lobe divergence resulted in higher maximal drag; however, lobe divergence was limited to 1.8 due to stability and fabrication constraints. The optimal design chosen for medusoid fabrication corresponded to the geometry achieving peak drag at lobe divergence of 1.8. For performance comparisons, we also chose to fabricate a suboptimal design with much lower predicted drag at the same relative lappet length. Final optimal and suboptimal body designs promoted propulsion and sieving, respectively (FIG. 11j, left, and FIGS. 6c and 6d).

Digital Particle Image Velocimetry (DPIV).

Fluid dynamics in free-swimming jellyfish and medusoids were assessed through DPIV that allows for quantitative analysis of flow created by swimming animals in a two-dimensional plane 41. In DPW, fluid motion is determined by quantifying the displacement vectors of small seeding particles between successive video frames. The same basic DPIV set-up was used for jellyfish and medusoids (FIG. 12a). The specimens were imaged in custom-built acrylic containers filled with either artificial seawater at room temperature (for jellyfish), or with Tyrode's solution maintained at 35° C. using a custom-made heated stage (for medusoids). Additionally, the medusoid tank was equipped with two U-shaped platinum electrodes to allow for electric field stimulation. The bath was seeded with neutrally buoyant, silver-coated, hollow glass spheres with a nominal diameter of 13 μm (Potters Industries Inc., Brownwood, Tex. 76801, USA). Particle illumination in the medusoid bath and the larger jellyfish tank was achieved using a green (532 nm) 5 mW laser pointer or a 300 mW hand-held laser (Laserglow Technologies, Ontario, Canada), respectively. The laser beam was diverged into a 1 mm-thick planar sheet by a plano-concave cylindrical lens with a focal length of −4 mm (Thorlabs, Newton, N.J. 07860, USA) to illuminate a horizontal plane dissecting the vertically swimming specimens along their bell diameter (FIG. 12a). A camera was installed perpendicular to the laser sheet. In the case of the jellyfish, the motions of the particles were recorded with a Sony HDR-SR12 camcorder (1,440×1,080 pixels, 30 frames per second; Sony Electronics, San Diego, Calif. 92127, USA). In case of the medusoids, an A602f/fc Basler camera was used (656×491 pixels, 100 frames per second; Basler Vision Technologies Exton, Pa. 19341, USA; example recording: Supplementary Movie 5). The videos were processed with an in-house DPIV algorithm. The DPIV interrogation window size was 32×32 pixels with 50-70% overlap (16 to 10 pixels step size). Velocity vectors were yielded from average particle displacement within each interrogation window (FIGS. 12b and 12c). Resultant velocity and vorticity fields (FIG. 12d) were used to compare fluid transfer and vortex formation in medusoids and jellyfish (FIG. 4).

Propulsion/Feeding Performance Analysis.

Feeding performance was defined as the relative amount of fluid drawn toward the subumbrellar bell aperture (site of feeding) per recovery stroke. Briefly, in each DPIV image frame a reference line was drawn to span the stopping vortex formed during the recovery stroke (FIG. 12d), which approximates the diameter of subumbrellar bell aperture (site of feeding). The normal components of the velocity vectors across this reference line correspond to the velocity profile across the bell aperture at a given instant of time (FIG. 12e). Flow toward the bell was defined to be positive. Flow velocities were nondimensionalized by multiplying with the total duration of the recovery stroke and dividing by bell diameter. Volumetric flux across the area of the subumbrellar bell aperture was estimated by assuming that the specimens were axisymmetric and integrating the velocity profile over a circular area.

Propulsion performance was defined as relative swimming speed expressed in units of body length per stroke. Here, body length denoted the bell height at maximal contraction. Propulsion performance was calculated from brightfield video recordings of free-swimming medusoids and jellyfish.

Kinematic Analysis.

Analysis of medusoid and jellyfish lobe kinematics was performed by tracking frame-to-frame displacement of lobe tips relative to the bell using ImageJ (US National Institutes of Health) and an in-house MATLAB algorithm. Angular lobe velocity was expressed as function of time (FIG. 2a). For each lobe, relative stroke asymmetry was defined as the maximal lobe contraction velocity divided by maximal lobe relaxation velocity. Relative contraction asymmetry within each set of labeled lobes was expressed as the temporal variance in reaching maximal contraction velocity.

Statistical Methods.

Figure 2C:
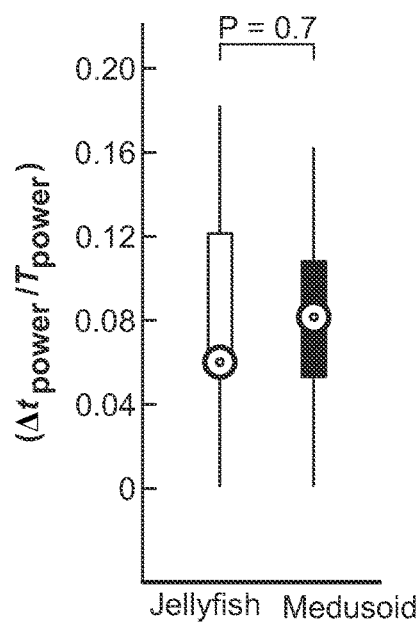
Figure 2D:
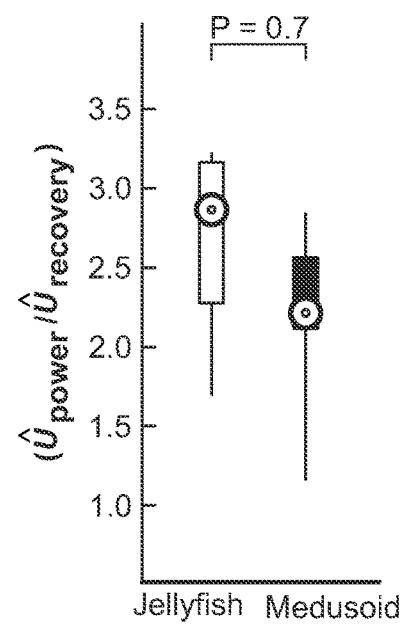
Figure 4A:
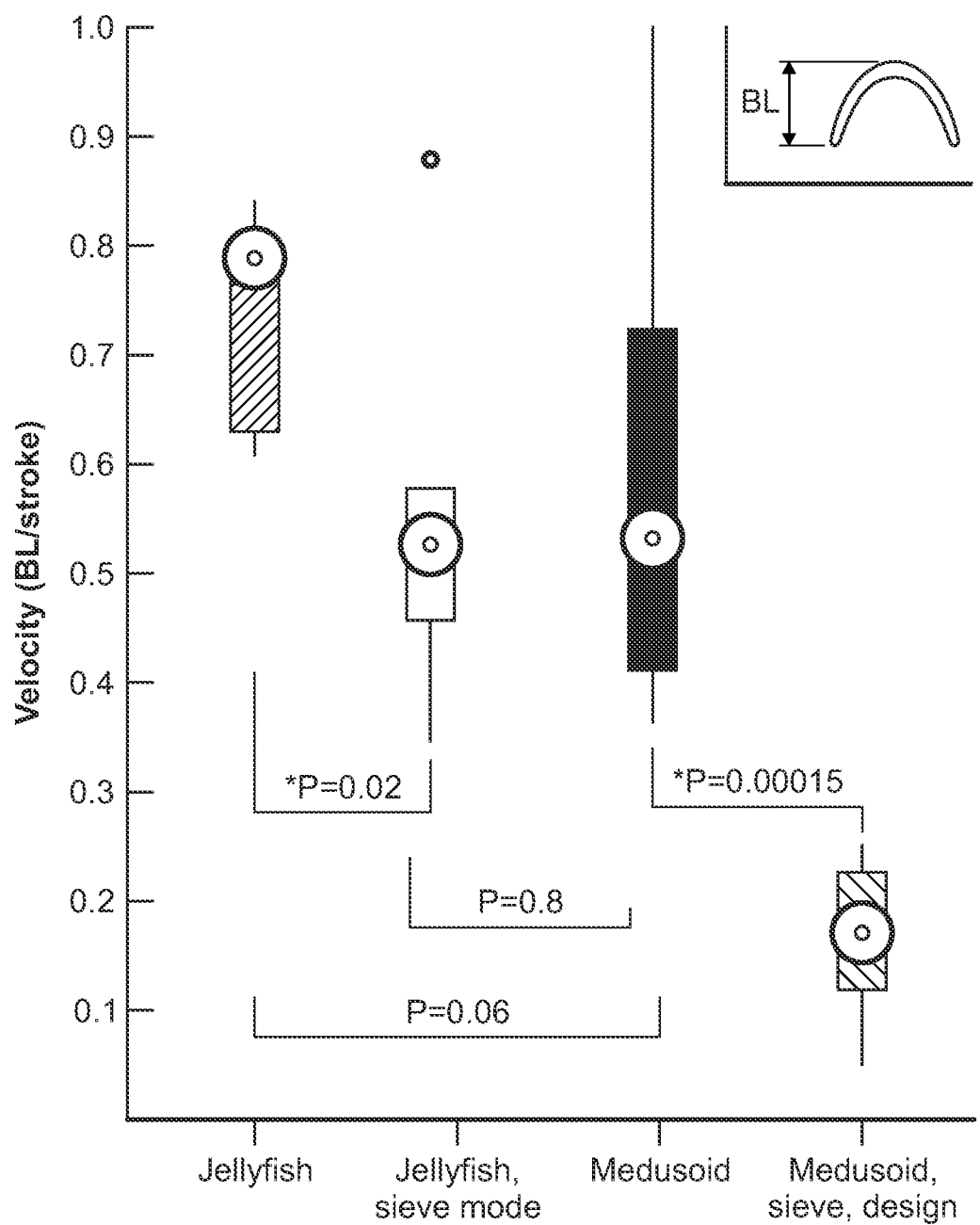
FIGS. 4A-4B depict the achievement of functional performance of jellyfish by the medusoids. (a) Box-plot representation of relative propulsion performances in BL/S. Performance in jellyfish (n=7, red) and optimally designed medusoids (n=11, black) spans similar range. Compared to optimal conditions, jellyfish in sieve conditions (n=7, blue) and sieve-designed medusoids (n=6, gray) performed significantly worse (P=0.02 and P=0.00015, respectively; Wilcoxon rank sum test). Bull's eyes, median; lower edge of box, 25th percentile; upper edge of box, 75th percentile; whiskers, extreme data points not considered outliers; circle, outlier. Asterisks denote statistically significant difference, P<0.05. (b) For each stage of the recovery stroke, flow profile (i) and volume flow rate (ii) across subumbrellar reference section reveal similar fluid transport, that is, "feeding current" in jellyfish and medusoids, and reduced performance—including flow reversal—in sieve-designed medusoids. Data shown for one representative sample each. Left: reference section at each stage of recovery stroke. Measured quantities are nondimensionalized to facilitate comparison. R, bell radius (mm); jellyfish: R=9 mm; medusoid: R=9 mm; sieve-designed medusoid: R=9 mm; r, radial distance (mm) from center. $T_{recovery}$, duration (s) of recovery stroke; jellyfish: T=0.2 s, medusoid, T=0.48 s; sieve-designed medusoid, T=0.55 s; t, time (s) elapsed since start of recovery stroke. U, flow velocity [mm/s] normal to reference section; jellyfish: $U_{max}$=9 mm/s; medusoid: $U_{max}$=2.4 mm/s; sieve-designed medusoid: $U_{max}$=1.6 mm/s. Q, volume flow rate (mm$_3$/s) passing across reference area (circle with diameter reference section); jellyfish: $Q_{max}$=100 mm$^3$/s; medusoid: $Q_{max}$=40 mm$^3$/s; sieve-designed medusoid: $Q_{max}$=15 mm3/s.

Lobe kinematics and propulsion performance data did not follow a normal (or otherwise obvious) statistical distribution, and sample sizes were relatively small (in most cases n<10). Therefore, nonparametrical methods were chosen for both data analysis and data representation (FIGS. 2c, 2d and 4a). Briefly, the data sets are presented in a so-called box-plot diagram, which gives a graphical summary of the data distribution in a nonparametric form, that is, without making assumptions about an underlying statistical distribution. The box-plot summarizes each data set in five numbers: median (bull's eye), 25th and 75th percentile (upper and lower edge of rectangle, respectively), and the smallest and the greatest observation (upper and lower end of whiskers, respectively). The Wilcoxon rank-sum test, synonymously called Mann-Whitney U test or Mann-Whitney-Wilcoxon (MWW) test, was employed for examining the sample sets pairwise for statistically significant differences in performance/kinematics. The P values are noted in the plots (FIGS. 2c, 2d and 4a). Here, the P values denote the probability of obtaining two data distributions that are at least as different as the ones that were actually observed if the two sample sets were equal in their performances/kinematics (null hypothesis). Asterisks denote a statistically significant difference, that is, $P<\alpha=0.05$, where $\alpha$ is the significance level.

Introduction

Reverse engineering of biological form and function requires hierarchical design over several orders of space and time. Recent advances in the mechanistic understanding of biosynthetic compound materials, computer-aided design approaches in molecular synthetic biology and traditional soft robotics, and increasing aptitude in generating structural and chemical microenvironments that promote cellular self-organization have enhanced the ability to recapitulate such hierarchical architecture in engineered biological systems.

Here, the capabilities have been combined in a systematic design strategy to reverse engineer a muscular pump. Described herein is the construction of a freely swimming jellyfish from chemically dissociated rat tissue and silicone polymer as a proof of concept. The constructs, termed 'medusoids', were designed with computer simulations and experiments to match key determinants of jellyfish propulsion and feeding performance by quantitatively mimicking structural design, stroke kinematics and animal-fluid interactions. The combination of the engineering design algorithm with quantitative benchmarks of physiological performance demonstrates that this strategy is broadly applicable to reverse engineering of muscular organs or simple life forms that pump to survive.

Results and Discussion

Figure 5:
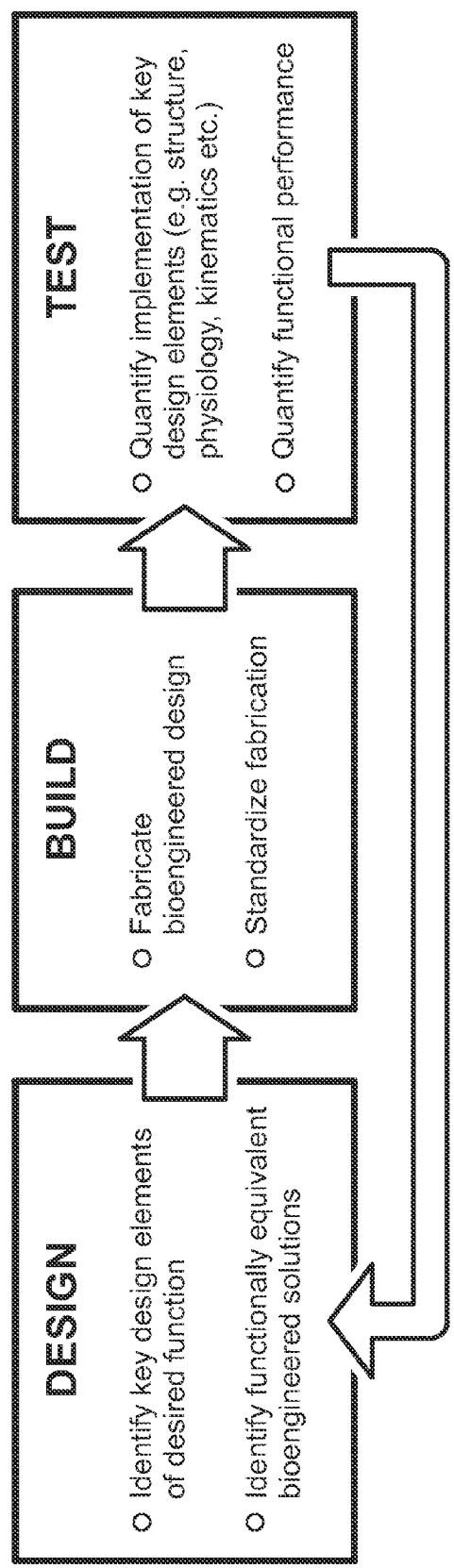
FIG. 5 depicts the engineering design algorithm for tissue-engineering functional constructs. The design algorithm consists of three phases—design, build and test. The series of steps is iterated until the engineered construct exhibits the desired functional performance. Design phase: Start by identifying quantitative benchmarks characterizing the desired function in a model system. Then, identify key design elements contributing to this function. Determine functionally equivalent bioengineered solutions from the pool of available materials. Build phase: Proceed by fabricating the bioengineered solution and standardize fabrication for repeatability. Test phase: Quantify implementation of key design elements including structural, physiological, kinematic and fluid dynamics characteristics. Finally, compare functional performance to desired behavior using quantitative benchmarks. Return to design phase if performance is unsatisfactory.

Jellyfish represent a unique test case for design-based tissue engineering of a functional device (FIG. 5) as their repetitive behavior and simple bauplan facilitate probing, and potentially emulating, structure-function relationships. Jellyfish medusae feature a radially symmetric, transparent body powered by a few, readily identifiable cell types, such as motor neurons and striated muscle, and they generate quantifiable output functions, for example, well-defined feeding and swimming currents, based on straightforward body-fluid interactions. The key factors contributing to the jellyfish stroke cycle and its functions, that is, feeding and propulsion were identified (FIG. 1a), with the goal of determining potential functional substitutes from tissue-engineering materials. First, previous studies and observations have highlighted the importance of symmetric and complete bell contraction, which the jellyfish achieves by synchronously activating its axisymmetric musculature through a system of distributed pacemakers, resulting in controlled folding of the lobed or otherwise compressible bell (FIG. 1b, top). It was reasoned that a sheet of cultured muscle tissue synchronized by an electrical field would be functionally equivalent (FIG. 1b, bottom). Second, jellyfish stroke kinematics derive from the alternating action of fast muscle contraction and slow elastic recoil of the bell's compliant gelatinous matrix (mesoglea), corresponding to the power and recovery strokes (FIG. 1c, top). For the engineered construct, a bilayer of muscle and synthetic elastomer was envisioned that would be suitable to mimic this interaction, that is, the muscle would provide the force to contract the bell, and the elastomer would act to restore the original shape (FIG. 1c, bottom). Third, previous research has highlighted the contribution of viscous, fluid boundary layers to efficient solid-fluid interactions in juvenile medusae and other aquatic organisms (FIG. 1d, top). It was concluded that the geometry of the construct should be chosen based on ambient fluid conditions so as to facilitate the formation of boundary layers that fill the gaps between neighboring lobes (FIG. 1d, bottom).

How the tissue components of juvenile specimens, so-called ephyrae, of the scyphozoan jellyfish *Aurelia aurita* generate these three key properties was then investigated in detail, and in parallel selection and assembly of functionally equivalent substitutes from synthetic and tissue-engineered materials was also investigated. In *Aurelia aurita*, bell contraction relies on a monolayer of striated muscle lining the subumbrella. Using chemical staining, the cellular architecture of the swimming muscle in *Aurelia* sp. Ephyrae was mapped, which consists of a central ring merging into eight radial branches (FIG. 6a). Jellyfish myofibrils displayed a high degree of alignment, and longitudinal continuity suggested mechanical end-to-end coupling of muscle cells. Optical mapping of membrane voltage potential revealed that, at least locally, action potentials propagate continuously within jellyfish muscle (FIG. 7), whereas global coordination of muscle activation is thought to be accomplished by a networked ensemble of pacemaker cells.

Together, these findings demonstrated that highly ordered myofibril organization paired with spatiotemporal coordination of contraction would be critical to emulating jellyfish muscle function. As it turns out, these properties are intrinsic to engineered monolayers of anisotropic rat cardiac tissue designed to mimic the laminar structure of the heart ventricles. Given a suitable micro-pattern of extracellular matrix cues, neonatal rat cardiomyocytes self-assemble into a functional syncytium with well-defined axes of force generation. Cell-to-cell electromechanical coupling promotes tissue-wide propagation of electrical impulses and spatiotemporal synchronization of contraction, which differentiates cardiomyocytes from most other contractile cell types, such as skeletal myocytes. In particular, engineered cardiac tissue constructs contract synchronously when electric field stimulation is applied, eliminating the need for internal innervation by means of neuronal cells or embedded electrodes. Medusoid body design was modeled after that of early-stage ephyrae, which do not possess a closed bell but an array of eight lobes arranged radially to a central disc (FIG. 1e). Jellyfish myofibril organization was emulated in a monolayer of patterned neonatal rat cardiomyocytes, as evidenced by morphology at different scales as well as quantification of actin-fiber alignment (FIGS. 1f, 1g and FIG. 8). Further, optical mapping of membrane voltage potential confirmed the continuous spread of electrical activity through the nerve-free cardiac tissue (FIG. 7).

Next, suitable substrates to substitute for mesoglea in stroke kinematics were identified. Jellyfish stroke kinetics result from the cooperative effects of muscle and mesoglea mechanics, the former constricting the bell during the power stroke, the latter restoring the original shape through elastic recoil during the recovery stroke. In the medusoid, a similar interaction was created by coupling a layer of anisotropic cardiomyocytes with an elastic silicone substrate of adjustable stiffness. Millimeter-scale medusoid constructs were fabricated by seeding neonatal rat cardiomyocytes onto micro-patterned, jellyfish-shaped, polydimethylsiloxane (PDMS) thin films (FIG. 9). Thus, PDMS surface modifications controlled two-dimensional tissue architecture, whereas the overall medusoid shape was equal to PDMS film dimensions. Jellyfish mesoglea, however, is a heterogeneous substrate with soft folds allowing for compression and with stiffened ribs serving as springs and pivots around which the substrate can bend into a bell. A homogeneous disc of PDMS, on the other hand, is incompressible and cannot be turned into a bell without wrinkling, buckling or cracking, all of which require considerably higher stresses than bending. As a result, a naive biomimetic approach of precisely copying the muscle architecture and circular body shape of late-stage ephyrae (FIG. 6b) led to minimal film deformation and no propulsion at all. Successful medusoid designs must therefore match muscle stress generation with substrate compliance. In the lobed design, each arm freely bends around its base such that circumferential compression is avoided and a quasi-closed bell is formed at maximal contraction. The lobe bending angle was maximized by aligning the muscle fibers to the main axis of deformation and using minimal film thickness (~20 μm) without compromising stability, exploiting the known relation between myocyte tissue architecture, PDMS film thickness and resulting curvature of contraction. In particular, anisotropic engineered cardiac tissue generates peak stresses of 10 mN/mm$^2$, which is similar to native cardiac muscle and sufficient to bend PDMS membranes of 20-μm thickness at a curvature of 1/mm, meaning that a 2-mm long lobe will be arched by more than 90 degrees. Conversely, in the bell's center, where little deformation was required, a circumferential muscle layout was implemented to facilitate electrical conduction between neighboring lobes, as action potential propagation velocity is fastest along the longitudinal axis of an anisotropic syncytium (FIG. 7).

Medusoids of this design responded to electrical field stimulation applied by two U-shaped electrodes flanking the bath (1 Hz, 2.5 V cm$^{-1}$, 10 ms pulse width; FIG. 10), with power and recovery strokes that closely resembled the stroke cycle of freely swimming jellyfish ephyrae (FIG. 2a).

Constructs were assayed for up to 1 h, after which contractility and responsiveness to pacing decreased, presumably due to tissue damage resulting from electrical and manual manipulation. Tracking lobe displacement relative to the main body revealed qualitatively similar velocity-time functions of lobe motion in medusoid constructs compared to ephyrae (FIG. 2b). In particular, the greatest lobe acceleration and velocity were reached during the power stroke, followed by more gentle recovery. Quantitative analysis confirmed a similar degree of lobe synchrony in the two systems as well as similar ratios of contraction and relaxation velocities (FIGS. 2c and 2d). These results demonstrate that mechanistic understanding of the desired function and of available materials makes it possible to design and build constructs that exhibit similar macroscopic behaviors as the model system without necessarily sharing all underlying components.

Adequate three-dimensional kinematics do not, however, guarantee efficient body-fluid interactions, which must be considered separately. In particular, although emulating the ephyral body plan facilitates compression-free deformation, this design also risks 'leaking' fluid through the gaps, and thus compromising fluid transport, unless lobe shape promotes sufficient bell drag, that is, the formation of overlapping viscous boundary layers to resist gap-crossing flows. Viscous boundary layers are fluid velocity gradients that form at the fluid-animal interface and follow the motion of the lobes, effectively extending their reach. Boundary layers of sufficient thickness overlap and close interlobate gaps to oncoming flow, thus increasing bell drag. The factors determining bell drag are lobe Reynolds number (the local ratio of inertial to viscous fluid forces) and bell porosity (gap width relative to lobe width), or, more directly, fluid viscosity, lobe kinematics and body geometry. A fluid dynamics model that determined optimal parameters of the jellyfish-like geometry for transporting isotonic Tyrode's solution at 37° C. (mammalian cell culture conditions) while adhering to structural stability and fabrication constraints was developed and empirically validated (FIG. 11). The corresponding medusoid design features wedge-shaped lobes separated by gaps (FIG. 1e and FIG. 6c) that allow for compression-free, collision-free deformation, whereas fluid leakage is resisted through formation of viscous boundary layers.

Figure 3A:
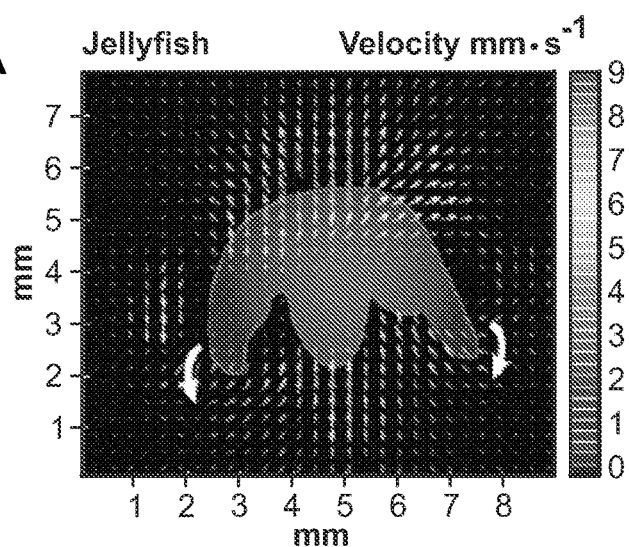
FIGS. 3A-3F depict the generation of jellyfish-like flow fields by the medusoids. (a-c) Velocity field at end of power stroke reveals similar thrust generation in a, jellyfish and b, medusoids, and reduced thrust in c, sieve-designed medusoids. White arrows, lobe motion. (d-f) Voracity field during recovery stroke reveals similar formation of stopping vortices in jellyfish (d), medusoids (e) and sieve-designed medusoid (f).Black contours, counter-rotating cross-sections of stopping vortex ring; gray arrows, lobe motion.
Figure 3B:
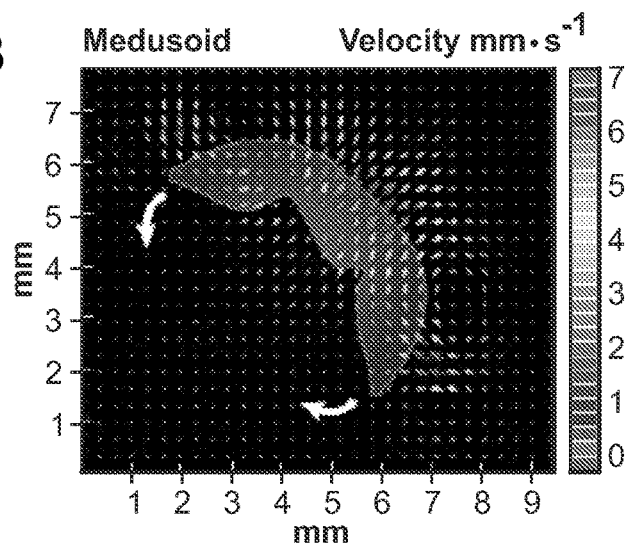
Figure 3C:
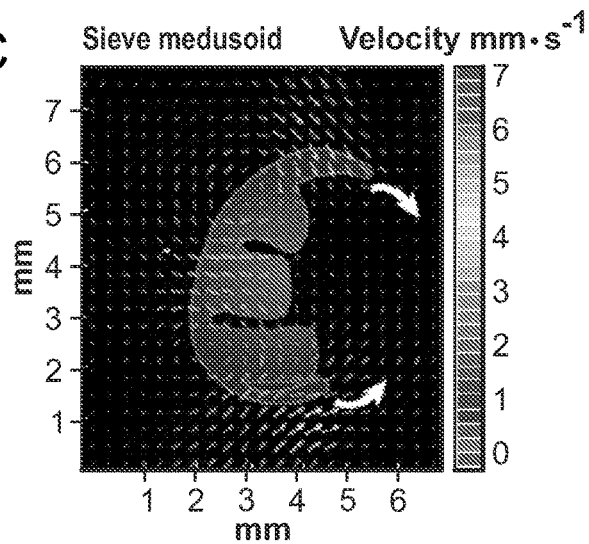
Figure 3D:
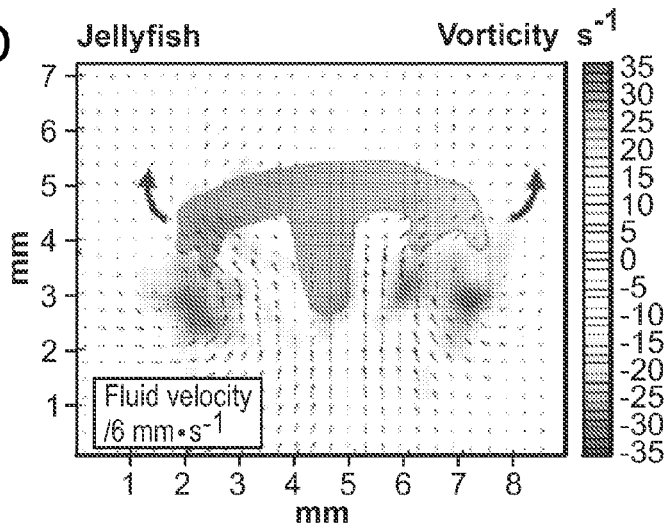
Figure 3E:
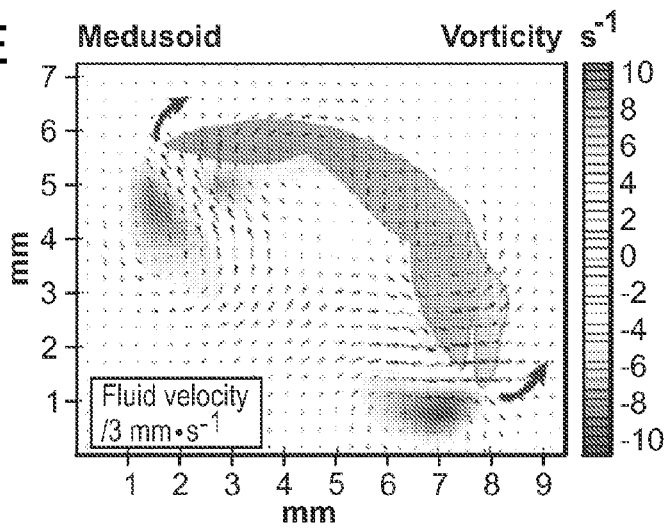
Figure 3F:
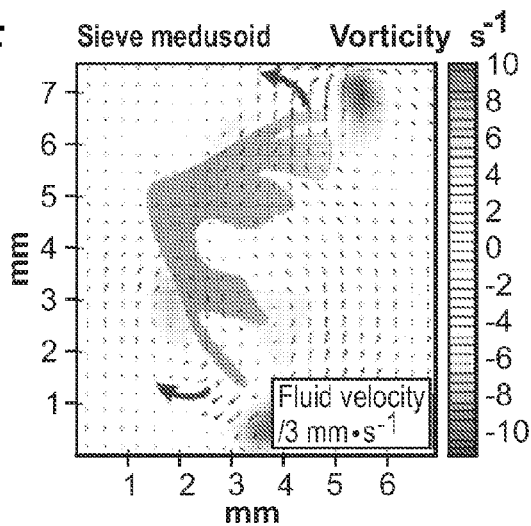
Figure 4B:
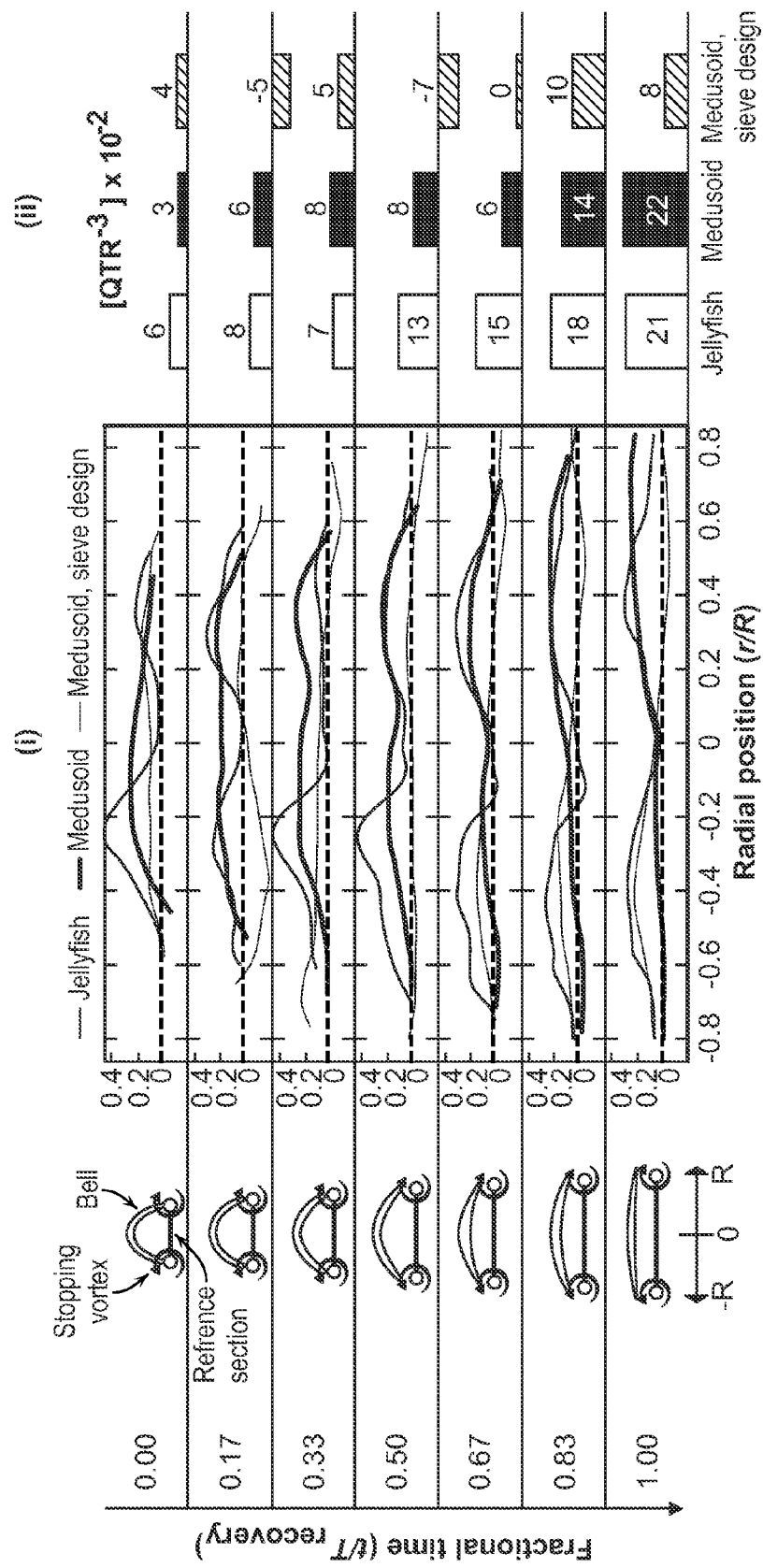

Medusoids with optimized muscle and PDMS geometry succeeded in replicating jellyfish swimming behavior and achieved similar propulsion and feeding performances. In particular, digital particle image velocimetry (DPIV) (FIG. 12) revealed qualitatively and quantitatively similar flow fields generated during bell contraction. Both medusoid and jellyfish power strokes generated fluid velocities between 6 and 10 mm s$^{-1}$, indicating similar momentum transfer (FIGS. 3a and 3b). DPIV also revealed the wake structures formed due to bell acceleration and motion reversal. The presence of a so-called stopping vortex, a ring of circulating fluid shed during the recovery stroke, suggested that jellyfish-like feeding currents, which draw fluid inside the bell, were produced by the medusoid construct (FIGS. 3d and 3e). Changes to medusoid geometry resulted in altered fluid interactions (FIGS. 3c and 3f), which will be discussed in detail below. Medusoid and jellyfish propulsion performances were expressed in units of body lengths traveled per swimming stroke (BL/S), a common metric for biological locomotion efficiency that normalizes for size differences between the specimens that are being compared. Here, body length was defined as bell height at maximal contraction (FIG. 4a, inset). Medusoid performance mostly ranged between 0.4 and 0.7 and occasionally reached values close to 1 BL/S. Upper medusoid performance thus covered the span of regular ephyral swimming efficiency, which varied between 0.6 and 0.8 BL/S (FIG. 4a). Relative feeding performance was given by nondimensionalized velocity profile and volumetric flux across the underside of the bell during the recovery stroke (FIG. 4b). These metrics were drawn from DPIV data and quantify the rate of fluid turnover at the solid-liquid interface. In ephyrae, this rate determines the efficiency of transporting prey items to the subumbrellar feeding structures, hence the term 'feeding performance'. Comparison of volumetric flux across the entire bell revealed that medusoids and ephyrae processed fluid at similar rates during each stage of the recovery stroke (FIG. 4b, ii). Total volumetric flux in the medusoid equaled 75% of ephyral flux. The corresponding velocity profile of medusoid and jellyfish confirmed positive flux, that is, flow toward the bell, of similar magnitude throughout the stroke cycle (FIG. 4b, i). Note that the pronounced 'M'-shaped velocity profile observed in the ephyrae derives from the fact that the central oral arms (not present in medusoids) are diverting the flow.

For comparison, a suboptimal layout featuring slim, straight lobes was also tested (FIG. 6d). This body plan is adopted by ephyrae exposed to relatively low water temperatures where increased kinematic viscosity and thicker boundary layers allow for greater gaps between lobes without compromising fluid transport as boundary layer overlap is maintained. Exposed to the lower viscosity conditions at warmer temperatures, this same body plan provides little resistance to the flow and effectively sieves through the fluid instead of transporting it (Supplementary FIGS. 7h-7j). Similarly, sieve-designed medusoids accelerated the fluid to no more than 50% of the velocities reached by the original design, which was optimized for 37° C. (FIGS. 3b and 3c), resulting in a 60% reduction of median propulsion performance (FIG. 4a). Further, although sieve-designed medusoids generated a stopping vortex ring during the recovery stroke (FIGS. 3e and 3f), they nonetheless exhibited an 80% reduction in total volumetric flux toward the bell compared to optimal medusoids. As the velocity profile reveals, the reduced feeding performance was due to lower flow rates as well as reversal of flow, which corresponds to expelling potential prey from the bell (FIG. 4b).

This study extends the process of designing novel biological or bio-inspired systems to the realm of pseudo-organisms. Traditional quantitative engineering approaches have been employed to build a millimeter-scale construct from living and synthetic materials that emulates typical jellyfish behaviors. It has been demonstrated herein how such devices can be designed and incorporated into synthetic organisms that mimic the biological function of an organism. As shown here for muscle-powered fluid transport, the main challenge for macroscale synthetic biology is to dissect complex behaviors into mechanistic components that have functionally equivalent, tissue-engineered solutions. The results presented herein illustrate that a biomimetic design does not always reproduce the intended function (FIG. 6b), and that complex behaviors can be generated from relatively few materials by establishing key interactions with cells that exploit their powers of self-organization.

In conclusion, jellyfish swimming, a well-defined animal behavior, has been successfully recreated in an artificial tissue construct.

At this stage, swimming behavior is limited to exactly one stereotypic mode of execution because there are no means of fine-controlling local muscle contraction to achieve, for example, turning and maneuvering. However, the future integration of multiple cell types and compound materials allows for constructs of greater autonomy that are capable of sensing the environment and employing internal decision-making circuits to choose a suitable response from a variety of behaviors.

Exemplary embodiments presented herein is applicable to the assembly of any synthetic muscular pump. With respect to the engineering of tissues or organs intended for therapeutic use in patients, these results highlight the importance of developing and applying quantitative performance specifications. With simple model systems, the design of these specification standards can be accomplished in carefully controlled conditions.

Example 2

Design and Fabrication of a Tissue Engineered Fluidic Pump

As depicted in FIGS. 13-24 biomimetic tissue engineered fluidic pumps have been designed and fabricated. This pumping system (referred to as "the pump") includes an engineered pumping muscle, one-way valves, e.g., tissue engineered valves, and component enclosures. The devices of the present invention are suitable for in vitro screening assays test drug and for in vivo application as replacement valves, ventricles, and/or as an artificial heart.

Briefly, the engineered tissue is provided by fabricating a pump-shaped or valve-shaped scaffold in order to direct the location and individual cellular position of the contracting cells. The scaffold can be synthetic or natural, permanently incorporated or dissolving, depending on the application Suitable scaffolds may be prepared using the devices and methods for the fabrication of micron, submicron, or nanometer dimension polymeric fibers, e.g., the "Rotary Jet Spinning System" or "RJS" system described in, U.S. Patent Publication No. 2012/0135448, U.S. patent application Ser. No. 13/988,088, and U.S. Provisional Application Nos. 61/764,349 and 61/837,779. The fibers may be formed as pump-shaped units, e.g., cone shaped, and, e.g., assembled into a pump housing for cell seeding.

Suitable scaffolds may also be prepared by fabricating a gel (e.g., gelatin, collagen alginate hyaluronan) into pump-shaped units by, for example, cast molding, and similarly assembled into a pump housing.

Natural, de-cellularized animal material may be cleaned, and re-seeded with cells of interest may also be used to create a scaffold for a pump. Such materials may include, but are not limited to, extracellular matrix proteins left behind during the de-cellularization process that include fibrous proteins such as collagens, fibronectin, elastin, and laminin. Other exemplary animal material left behind during the de-cellularization process also include hyaluronic acid, glycosaminoglycans, including heparin sulfate, chondroitin sulfate, and keratan sulfate. In some embodiments, whole biological tissues, such as heart, intestine, stomach and bladder, may be de-cellularized and reseeded for the tissue-engineered pump.

Muscle cells (or combinations of muscle cells and other cell types, such as nerve cells) suitable cells for seeding the scaffold include, for example, human cardiomyocytes derived from pluripotent stem cell lines that can be expanded, and differentiated onto the pump scaffold.

A conical pump with an 8 mm diameter face is capable of a stroke volume of 0.5 mL, defining the upper limit of the flow rate 30 mL/min at a basal pacing rate of 1 Hz for a single pumping unit.

FIGS. 13, 14 and 17 depict exemplary tissue-engineered pump devices of the invention.

FIG. 13 depict one embodiment, of an exemplary tissue-engineered pump. Polymeric nanofibers are helically wrapped around a conical mold to create a cone-shaped pump that provides topographical cues for anisotropic cardiac cultures. The fiber scaffold creates an anisotropic muscular tissue that can be tuned for optimal pumping efficiency. A light activated pacemaker engineered from optogenetic cardiac cells is implanted into the left ventricle mimic and is connected to the right ventricle mimic through a tubular tissue syncytium. Tissue engineered valves are situated at the entry and exit of elastomeric tubings connecting the pump housing to the fluidic connections. Dashed arrows indicate the direction of flow.

FIG. 14 depicts a CAD drawing of exemplary tissue-engineered pump devices including two pump assemblies in parallel. The figure shows that the tissue-engineered pump (the light gray cones having dark gray apical points) contract and propel liquid through a flexible one-way exflow valve (discs on right side of device). During retraction, fluid is withdrawn from the inlet port via inflow one-way valves (discs on the left side of the device). The valve housing enclosures are fitted such that the pump assemblies are interconnected to permit introduction of tissue engineered pacing nodes (e.g., an optically activated SA node) and/or electrically transmitted pacing signals (e.g., an SA node pacemaker).

FIG. 17 is a schematic of an exemplary tissue engineered muscular pump. Polymeric nanofibers are helically wrapped around a cylinder to create a tubular pump that provides topographical cues for anisotropic cardiac cultures. The nanofiber scaffold creates an anisotropic muscular tissue that can be tuned for optimal pumping efficiency. Tissue engineered valves, or synthetic elastomer check valves, are implanted at the inflow and outflow ports of elastomeric tubing. Dashed arrows indicate the direction of flow.

FIG. 15 depicts a CAD drawing of an exemplary valve assembly. A flexible material (e.g., a commercially available replacement valve, and/or a tissue-engineered valve described herein, may be used. In general, the disc shaped material deforms as fluid flows in one direction and is partially supported in the direction against flow. As backflow begins, fluid presses the flexible material against the partially supporting enclosure, sealing the port.

FIGS. 16B-16E depict the super-aligned biodegradable polycaprolactone (PCL) nanofiber scaffold fabricated by RJS for use in the exemplary tissue-engineered pump.

What is claimed:
1. A tissue-engineered pump, comprising:
a housing;
a conical member accommodated within the housing, the conical member comprising a rounded tip and a side wall cooperatively enclosing a cavity, wherein the rounded tip comprises an engineered circumferential muscle tissue, and wherein the side wall comprises an engineered anisotropic muscle tissue;
a first valve coupled to the conical member for enabling a fluid flow into the cavity of the conical member; and
a second valve coupled to the conical member for enabling a fluid flow out of the cavity of the conical member.

2. The tissue-engineered pump as claimed in claim 1, wherein the cavity, the first valve, and the second valve are configured such that contraction of the volume of the cavity pumps at least a portion of a fluid in the cavity of the conical member out of the cavity through the second valve.

3. The tissue-engineered pump as claimed in claim 1, wherein the engineered tissue is fabricated by:
forming micron, submicron or nanometer dimension polymeric fibers, the polymeric fibers configured in a conical shape; and
seeding muscle cells onto the polymeric fibers.

4. The tissue-engineered pump as claimed in claim 1, wherein the height of the conical member ranges from about 1 inch to about 6 inch.

5. The tissue-engineered pump as claimed in claim 1, wherein the outer diameter of the conical member at its widest portion ranges from about 1 inch to about 4 inch.

6. The tissue-engineered pump as claimed in claim 1, wherein the wall thickness of the conical member ranges from about 0.1 mm to about 2 mm.

7. A method for forming a tissue-engineered pump, the method comprising:
providing a housing;
providing a conical member within the housing, the conical member comprising a rounded tip and a side wall cooperatively enclosing a cavity, wherein the rounded tip comprises an engineered circumferential muscle tissue, and wherein the side wall comprises an engineered anisotropic muscle tissue;
coupling a first valve to the conical member for enabling a fluid flow into the cavity of the conical member;
coupling a second valve to the conical member for enabling a fluid flow out of the cavity of the conical member; and
coupling the conical member to an energy source for electrically stimulating a collection of cells within the engineered tissue to cause contraction of a volume of the cavity.

8. The method as claimed in claim 7, wherein the engineered tissue is fabricated by:
forming micron, submicron or nanometer dimension polymeric fibers, and configuring the polymeric fibers in a conical shape; and
seeding muscle cells onto the polymeric fibers.

9. A method for identifying a compound that modulates a muscle tissue function, the method comprising:
providing the tissue-engineered pump of claim 1 or the tissue-engineered pump produced according to the method of claim 7;
contacting the muscle tissue with a test compound; and
determining an effect of the test compound on a muscle function in the presence and absence of the test compound, wherein a modulation of the muscle function in the presence of said test compound as compared to the muscle function in the absence of said test compound indicates that said test compound modulates a muscle function, thereby identifying a compound that modulates a muscle function.

10. A method for identifying a compound useful for treating or preventing a muscle disease, the method comprising
   providing the tissue-engineered pump of claim 1 or the tissue-engineered pump produced according to the method of claim 7;
   contacting the muscle tissue with a test compound; and
   determining an effect of the test compound on a muscle function in the presence and absence of the test compound, wherein a modulation of the muscle function in the presence of said test compound as compared to the muscle function in the absence of said test compound indicates that said test compound modulates a muscle function, thereby identifying a compound useful for treating or preventing a muscle disease.

11. The tissue-engineered pump as claimed in claim 1, further comprising: an energy source for stimulating a collection of cells within the engineered tissue to cause contraction of a volume of the cavity.

12. The tissue-engineered pump of claim 11, wherein the energy source provides electrical energy to electrically stimulate the collection of cells.

13. The tissue-engineered pump of claim 11, wherein the energy source provides light to stimulate the collection of cells.

14. The tissue-engineered pump as claimed in claim 1, wherein the first and second valves are check valves.

15. The method of claim 9, wherein the muscle function is a biomechanical activity.

16. The method of claim 15, wherein the biomechanical activity is selected from the group consisting of contractility, cell stress, cell swelling, and rigidity.

17. The method of claim 16, wherein the contractility is an electrophysiological activity.

18. The tissue-engineered pump as claimed in claim 1, wherein the conical member comprises micron, submicron, or nanometer dimension polymeric fibers helically wrapped into a conical shape.

19. The tissue-engineered pump as claimed in claim 1, further comprising
   a second housing;
   a second conical member accommodated within the housing, the second conical member comprising a rounded tip and a side wall cooperatively enclosing a second cavity smaller than the cavity of the conical member, wherein the rounded tip of the second conical member comprises an engineered circumferential muscle tissue, and wherein the side wall of the second conical member comprises an engineered anisotropic muscle tissue.

* * * * *